US008466090B2

(12) United States Patent
Kleinfeld et al.

(10) Patent No.: US 8,466,090 B2
(45) Date of Patent: Jun. 18, 2013

(54) DEVELOPMENT AND USE OF FLUORESCENT PROBES OF UNBOUND ANALYTES

(75) Inventors: Alan Marc Kleinfeld, La Jolla, CA (US); Andrew Henry Huber, Encinitas, CA (US); James Patrick Kampf, San Diego, CA (US); Thomas Kwan, San Diego, CA (US); Baolong Zhu, San Diego, CA (US)

(73) Assignee: FFA Sciences LLC, San Diego, CA (US)

( * ) Notice: Subject to any disclaimer, the term of this patent is extended or adjusted under 35 U.S.C. 154(b) by 318 days.

(21) Appl. No.: 12/535,617

(22) Filed: Aug. 4, 2009

(65) Prior Publication Data

US 2009/0318299 A1 Dec. 24, 2009

Related U.S. Application Data

(62) Division of application No. 11/085,792, filed on Mar. 21, 2005, now Pat. No. 7,601,510.

(60) Provisional application No. 60/555,224, filed on Mar. 22, 2004.

(51) Int. Cl.
*C40B 20/08* (2006.01)
*C40B 50/18* (2006.01)

(52) U.S. Cl.
USPC .................. 506/6; 506/4; 436/50.1; 530/350; 536/23.1; 536/23.5

(58) Field of Classification Search
USPC .......... 506/4, 6; 436/501; 530/350; 536/23.1, 536/23.5
See application file for complete search history.

(56) References Cited

U.S. PATENT DOCUMENTS

| 4,071,413 | A | 1/1978 | Takahashi et al. |
| 4,369,250 | A | 1/1983 | Gindler |
| 4,491,631 | A | 1/1985 | Imamura et al. |
| 4,580,059 | A | 4/1986 | Wolfbeis et al. |
| 4,833,332 | A | 5/1989 | Robertson et al. |
| 5,225,329 | A | 7/1993 | Marks |
| 5,227,307 | A | 7/1993 | Bar-Or et al. |
| 5,449,607 | A | 9/1995 | Wilton |
| 5,470,714 | A | 11/1995 | Kleinfeld |
| 5,496,735 | A | 3/1996 | Schwertner |
| 5,512,429 | A | 4/1996 | Wilton |
| 5,604,105 | A | 2/1997 | Jackowski |
| 5,914,112 | A | 6/1999 | Bednar et al. |
| 5,914,245 | A | 6/1999 | Bylina et al. |
| 5,977,174 | A | 11/1999 | Bradley et al. |
| 6,210,976 | B1 | 4/2001 | Sabbadini |
| 6,264,960 | B1 | 7/2001 | Robins et al. |
| 6,344,316 | B1 | 2/2002 | Lockhart et al. |
| 6,444,432 | B1 | 9/2002 | Kleinfeld |
| 6,461,875 | B1 | 10/2002 | Bar-Or et al. |
| 6,475,743 | B1 | 11/2002 | Bar-Or et al. |
| 6,492,179 | B1 | 12/2002 | Bar-Or et al. |
| 6,563,585 | B1 | 5/2003 | Rao et al. |
| 6,727,258 | B2 | 4/2004 | Baraldi |
| 6,750,030 | B2 | 6/2004 | Kleinfeld |
| 7,202,089 | B2 | 4/2007 | Kleinfeld |
| 2002/0013003 | A1 | 1/2002 | Wagner et al. |
| 2002/0081617 | A1 | 6/2002 | Buranda et al. |
| 2002/0142347 | A1 | 10/2002 | Knudsen et al. |
| 2002/0168692 | A1 | 11/2002 | Cass |
| 2002/0182197 | A1 | 12/2002 | Black et al. |
| 2004/0019109 | A1 | 1/2004 | Owman et al. |
| 2004/0077017 | A1 | 4/2004 | Karlstrom et al. |
| 2005/0239155 | A1 | 10/2005 | Alarcon et al. |
| 2005/0244864 | A1 | 11/2005 | Kleinfeld et al. |
| 2006/0257938 | A1 | 11/2006 | Kleinfeld et al. |
| 2009/0312522 | A1* | 12/2009 | Tendler et al. ................. 530/333 |
| 2010/0062948 | A1* | 3/2010 | Kleinfeld et al. ................. 506/9 |

FOREIGN PATENT DOCUMENTS

| EP | 1 043 587 B1 | 6/2003 |
| WO | WO 91/09310 | 6/1991 |
| WO | WO 93/08276 | 4/1993 |
| WO | WO 94/06014 | 3/1994 |
| WO | WO 98/57171 | 12/1998 |
| WO | WO 00/20840 | 4/2000 |
| WO | WO 00/47734 | 8/2000 |
| WO | WO 00/74728 | 12/2000 |
| WO | WO 02/089656 | 11/2002 |
| WO | WO 03/093438 | 11/2003 |
| WO | WO 2005/093103 | 10/2005 |

OTHER PUBLICATIONS

Janssen et al., Biochemical Journal. vol. 311(1): 49-57; 1995.*
Di Pietro et al., Biochimica et Biophysica Acta . vol. 1478:186-200; 2000.*
Davies, et al. "Perioperative Variability of Binding of Lidocaine, Quinidine, and Propranolol After Cardiac Operations," *Journal of Thoracic and Cardiovascular Surgery*, vol. 96, No. 4, pp. 634-641, Oct. 1998.
Ford, et al. "Use of Serum Markers of Myocardial Injury for the Early Diagnosis of Acute Myocardial Infarction," *ACC Current Journal Review*, vol. 5, No. 3, pp. 86-89, May/Jun. 1996.
Kleinfeld, et al. "Increases in Serum Unbound Free Fatty Acid Levels Following Coronary Angioplasty," *American Journal of Cardiology*, vol. 78, No. 12, pp. 1350-1354, Dec. 15, 1996.
Glatz, et al. "Fatty-Acid-Binding Protein as a Plasma Marker for the Estimation of Myocardial Infarct Size in Humans," *BR Heart J*, vol. 71, pp. 135-140, 1994.

(Continued)

*Primary Examiner* — T. D. Wessendorf
(74) *Attorney, Agent, or Firm* — Knobbe, Martens, Olson & Bear LLP

(57) ABSTRACT

A method for high throughput screening of probes is described. These probes are useful for characterization and measurement of unbound metabolites in a fluid sample, particularly characterization and measurement of levels of unbound free fatty acids. By practice of the disclosed invention, a profile of unbound metabolites can be determined for an individual which can be used to determine the individual's relative risk for disease such as stroke, cardiac disease and cancer.

6 Claims, 5 Drawing Sheets

OTHER PUBLICATIONS

Patel, et al. "Serum Levels of Unbound Free Fatty Acids I: Normative Data in Term Newborn Infants," *Journal of American College of Nutrition*, vol. 16, No. 1, pp. 81-84, 1997.

Peuhkurinen, et al. "Changes in Myocardial Energy Metabolism in Elective Coronary Angioplasty," *Cardiovascular Research*, vol. 25, pp. 158-163, 1991.

Richieri, et al. "Equilibrium Constants for the Binding of Fatty Acids with Fatty Acid-Binding Proteins from Adipocyte, Intestine, Heart, and Liver Measured with the Fluorescent Probe ADIFAB," *The Journal of Biological Chemistry*, vol. 269, No. 39, pp. 23918-23930, Sep. 30, 1994.

Richieri, et al. "Thermodynamic and Kinetic Properties of Fatty Acid Interactions with Rat Liver Fatty Acid-Binding Protein," *The Journal of Biological Chemistry*, vol. 271, No. 49, pp. 31068-31074, Dec. 6, 1996.

Richieri, et al. "Unbound Free Fatty Acid Levels in Human Serum," *Journal of Lipid Research*, vol. 36, No. 2, pp. 229-240, Feb. 1995.

Richieri, et al. "A Fluorescently Labeled Intestinal Fatty Acid Binding Protein. Interactions with Fatty Acids and its Use in Monitoring Free Fatty Acids," *The Journal of Biological Chemistry*, vol. 267, No. 33, pp. 23495-23501, Nov. 25, 1992.

Ruben, et al. "Serum Levels of Unbound Free Fatty Acids II: The Effect of Intralipid Administration in Premature Infants," *Journal of the American College of Nutrition*, vol. 16, No. 1, pp. 85-87, 1997.

Samanta, et al. "Possible Physiological Role of Myocardial Fatty Acid Binding Protein in Phospholipid Biosynthesis," *Journal of Lipid Mediators*, vol. 1, pp. 243-255, 1989.

Samanta, et a. "Free Radical Scavenging by Myocardial Fatty Add Binding Protein," *Free Radical Research Communications*, vol. 7, No. 2, pp. 73-82, 1989.

She, et al. "The Substrate Specificities of Four Different Lysophospholipases as Determined by a Novel Fluorescence Assay," *Biochem J.*, vol. 298, pp. 23-29, 1994.

Victor, et al. "Myocardial Tissue Free Fatty Acids," *Journal of Molecular and Cellular Cardiology*, vol. 16, No. 8, pp. 709-721, Aug. 1984.

*Textbook of Cardiovascular Medicine*, Eric J. Topol, Editor; Lippincott-Raven Publishers, Philadelphia, PA, 1998. Chapter 16, Harvey D. White, "Unstable Angina—Ischemic Syndromes." pp. 365-393.

Brown, et al., "Fatty Acids and the Inhibition of Mitogen-Induced Lymphocyte Transformation by Leukemic Serum," *The Journal of Immunology*. vol. 131, No. 2, pp. 1011-1016, Aug. 1983.

Butko, et al. "Acidic Phospholipids Strikingly Potentiate Sterol Carrier Protein 2 Mediated Intermembrane Sterol Transfer," *Biochemistry*. vol. 29, pp. 4070-4077, 1990.

Bansal, et al. "Stroke During Pregnancy and Puerperium in Young Females Below the Age of 40 Years as a Result of Cerebral Venous/Venous Sinus Thrombosis," *Japanese Heart Journal*, vol. 21, No. 2, pp. 171-182, Mar. 1980.

Ageeva, et al. "Structural and Functional Characteristics of Red Cell Membranes in Patients with Ischemic Stroke and Dyscirculatory Encephalopathy," *Zhurnal Nevrologii I Psikhiatrii Imeni SS Korsakova*, vol. 94, No. 1, pp. 6-8, 1994. English Abstract.

Imre, et al. "Increased Proportion of Docosahexanoic Acid and High Lipid Peroxidation Capacity in Erythrocytes of Stroke Patients," *Stroke*, vol. 25, No. 12, pp. 2416-2420, 1994.

N. Bazán, et al. "Membrane Lipids in the Pathogenesis of Brain Edema: Phospholipids and Arachidonic Acid, the Earliest Membrane Components Changed at the Onset of Ischemia," *Advances in Neurology*, vol. 28: *Brain Edema*, Raven Press, New York, 1980, pp. 197-205.

N. Bazán, et al. "Effects of Ischemia and Electroconvulsive Shock on Free Fatty Acid Pool in the Brain," *Biochimica et Biophysica Acta*, 218, 1970, pp. 1-10.

M. Ikeda, et al. "Polyphosphoinositides as a Probably Source of Brain Free Fatty Acids Accumulated at the Onset of Ischemia," *Journal of Neurochemistry*, Raven Press, New York, 1986, pp. 123-132.

V. Kurien, "Serum-Free-Fatty-Acids After Acute Myocardial Infarction and Cerebral Vascular Occlusion," *The Lancet*, Jul. 16, 1966, pp. 122-127.

G. Richieri, et al., "Interactions of Long-Chain Fatty Acids and Albumin: Determination of Free Fatty Acid Levels Using the Fluorescent Probe ADIFAB," *Biochemistry*, vol. 32, 1993, pp. 7574-7580.

G. Richieri, et al. "Kinetics of Fatty Acid Interactions with Fatty Acid Binding Proteins from Adipocyte, Heart, and Intestine," *The Journal of Biological Chemistry*, vol. 271, No. 19, May 10, 1996, pp. 11291-11300.

B. Weinberger, et al. "Effects of Perinatal Hypoxia on Serum Unbound Free Fatty Acids and Lung Inflammatory Mediators," *Biology of the Neonate*, vol. 79, 2001, pp. 61-66.

Pelser, et al. "Fatty Acid-Binding Proteins as Plasma Markers of Tissue Injury," *Clinica Chimica Acta*, vol. 352, pp. 15-35, 2005.

Li, et al. "High Throughput Screening Systems for Identification of Fatty Acid Uptake Inhibitors," *FASEB Journal*, vol. 20, No. 4, Part 1, Mar. 2006.

Richieri, et al. "Fatty Acid Binding Proteins from Different Tissues Show Distinct Patterns of Fatty Acid Interactions," *Biochemistry*, vol. 39, No. 24, 7197-7204, 2000.

Richieri, et al. "The Measurement of Free Fatty Acid Concentration with the Fluorescent Probe ADIFAB: A Practical Guide for the Use of the ADIFAB Probe," *Molecular and Cellular Biochemistry*, vol. 192, pp. 87-94, 1999.

Kampf, et al. "Fatty Acid Transport in Adipocytes Monitored by Imaging Intracellular Free Fatty Acid Levels," *The Journal of Biological Chemistry*, vol. 279, No. 34, pp. 35775-35780, Aug. 20, 2004.

Ikeda, et al. "Polyphosphoinositides as a Probable Source of Brain Free Fatty Acids, Accumulated at the Onset of Ischemia," *Journal of Neurochemistry*, vol. 47, No. 1, pp. 123-132, 1986.

Banaszak, et al. "Lipid-Binding Proteins: A Family of Fatty Acid and Retinoid Transport Proteins," *Advances in Protein Chemistry*, vol. 45, pp. 90-151, 1994.

van Zoelen, et al. "An Exact General Analysis of Ligand Binding Displacement and Saturation Curves," *Biochemistry*, vol. 32, pp. 6275-6280, 1993.

Veerkamp, et al. "Structural and Functional Features of Different Types of Cytoplasmic Fatty Acid-Binding Proteins," *Biochimica et Biophysica Acta*, vol. 1081, pp. 1-24, 1991.

Sacchettini, et al. "The Structure of Crystalline *Escherichia coli*-Derived Rat Intestinal Fatty Acid-Binding Protein at 2.5-Å Resolution," *The Journal of Biological Chemistry*, Vo. 263, No. 12, pp. 5815-5819, Apr. 25, 1988.

Evans, et al. "The Chemical Modification of Cysteine-69 of Rat Liver Fatty Acid-Binding Protein (FABP): A Fluorescence Approach to FABP Structure and Function," *Molecular and Cellular Biochemistry*, vol. 98, Nos. 1-2, pp. 135-140, Oct. 1990.

Lowe, et al. "Expression of Rat Intestinal Fatty Acid-Binding Protein in *Escherichia coli*," *The Journal of Biological Chemistry*, vol. 262, No. 12, pp. 5931-5937, Apr. 25, 1987.

Kohashi, et al. "Fluorescence Reaction of Biliruibin with Zinc Ion in Dimethyl Sulfoxide and its Application ot Assay of Total Bilirubin in Serum," *Analytica Chimica Acta*, vol. 365, No. 1-3, pp. 177-182, Jun. 5, 1998.

Haunerland, et al. "Fatty Acid-Binding Proteins—Insights from Genetic Manipulations," *Progress in Lipid Research*, vol. 43, pp. 328-349, 2004.

Bernlohr, et al. "Intracellular Lipid-Binding Proteins and Their Genes," *Annu. Rev. Nutr.*, vol. 17, pp. 277-303, 1997.

Lucke, et al. "New Insights into Intracellular Lipid Binding Proteins: The Role of Buried Water," *Protein Science*, vol. 11, pp. 2382-2392, 2002.

Lamia, et al. *Journal of Molecular Biology*, vol. 329, pp. 381-388, published online May 13, 2003.

Richieri, et al. *Journal of Biological Chemistry*, vol. 272, No. 27, pp. 16737-16740, 1997.

Definition of "Absolute Value"; Merriam-Webster Online Dictionary; downloaded from Merriam-webster.com; downloaded on Mar. 25, 2008.

Chattopadhyay, et al. "Measurement of Microsecond Dynamic Motion in the Intestinal Fatty Acid Binding Protein by Using Fluorescence Correlation Spectroscopy," *Proceedings of the National Academy of Sciences of the United States of America*, vol. 99, No. 22, pp. 14171-14176, Oct. 29, 2002.

Donato, et al. "A Fluorescence-based Method for Analyzing Retinoic Acid in Biological Samples," *Analytical Biochemistry*, vol. 357, No. 2, pp. 249-256, Oct. 15, 2006.

Supplementary European Search Report issued Dec. 20, 2010 to European patent application No. 09 70 1867.

Apple, et al. "Biomarker Discovery and Profiling, Unbound Free Fatty Acid Concentrations Are Increased in Cardiac Ischemia" *Clinical Proteomics Journal*, vol. 1, pp. 41-44, 2004.

Kleinfeld, et al. "Free Fatty Acid Release from Human Breast Cancer Tissue Inhibits Cytotoxic T-lymphocyte-mediated Killing," *Journal of Lipid Research*, vol. 46, pp. 1983-1990, 2005.

Yuvienco, et al. "Umbilical Cord Unbound Free Fatty Acid Concentration and Low Apgar Score," *American Journal of Perinatology*, vol. 22, No. 8, pp. 429-436, 2005.

Huber, et al. "Fatty Acid-specific Fluorescent Probes and Their Use in Resolving Mixtures of Unbound Free Fatty Acids in Equilibrium with Albumin," *Biochemistry*, vol. 45, pp. 14263-14274, 2006.

Cantor, et al. "B-type Natriuretic Peptide and Serum Unbound Free Fatty Acid Levels after Contemporary Percutaneous Coronary Intervention," *The Journal of Invasive Cardiology*, vol. 20, No. 4, Apr. 2008.

Almaguel, et al. "Activation and Reversal of Lipotoxicity in PC12 and Rat Cortical Cells Following Exposure to Palmitic Acid," *Journal of Neurosci Res.*, vol. 87, pp. 1207-2018, 2009.

Tuei, et al. "Effects of Human Serum Albumin Complexed with Free Fatty Acids on Cell Viability and Insulin Secretion in the Hamster Pancreatic β-cell Line HIT-T15," *Life Sciences*, vol. 88, pp. 810-818, 2011.

Bhardwaj, et al. "A Multicenter Comparison of Established and Emerging Cardiac Biomarkers for the Diagnostic Evaluation of Chest Pain in the Emergency Department," *American Heart Journal*, vol. 162, No. 2, pp. 276-282, 2011.

Jacobsen, et al. "Determination of Unbound Bilirubin in the Serum of Newborns," *Clinical Chemistry*, vol. 20, No. 7, pp. 783-789, 1974.

Odell, "Studies in Kernicturus. I. The Protein Binding of Bilirubin," *Journal of Clinical Investigation*, vol. 38, pp. 823-833, 1959.

Wennberg "Measuring Free Bilirubin: The Clinical Perspective," *Clinical Chemistry*, vol. 58, No. 5, pp. 811-813, 2012.

* cited by examiner

DEVELOPMENT AND USE OF FLUORESCENT PROBES OF UNBOUND ANALYTES

RELATED APPLICATIONS

This application is a divisional of U.S. application Ser. No. 11/085,792, filed Mar. 21, 2005, now U.S. Pat. No. 7,601,510, which claims priority to provisional Application No. 60/555,224, filed Mar. 22, 2004. Both applications are incorporated herein by reference in their entirety.

BACKGROUND OF THE INVENTION

1. Field of the Invention

The field of the invention relates to high throughput screening methods to provide specific probes that measure levels of unbound analytes, including unbound free fatty acids and other unbound metabolites. Also disclosed are probes obtained with the high throughput screening methods and the use of a combination of probes to determine an unbound free fatty acid profile or more generally an unbound metabolite profile for an individual.

2. Description of the Related Art

For purposes of the present disclosure, fatty acids are non esterified carboxylated alkyl chains of 1-30 carbons atoms which may exist as neutral (e.g. protonated, sodium or potassium salt) or ionic species, depending upon the pH and conditions of the aqueous media. Free fatty acids (FFA) are equivalent to fatty acids and both terms refer to the totality of FFA including those in aqueous solution as monomers plus those that are not in solution (for example bound to other macromolecules (proteins, membranes), cells or part of an aggregate of FFA (micelles, soaps and other more complex aggregates). FFA present as monomers in aqueous solution (either charged or neutral) are referred to as unbound free fatty acids (FFAu). For the purposes of the present disclosure, probes are fluorescently labeled proteins that upon binding an analyte, such as a FFAu, reveal a measurable change in fluorescence.

For purposes of the present disclosure, metabolites are physiologically important molecules whose molecular weight is approximately 2000 Da or less. These include molecules that occur naturally in the course of human or animal physiology or pathophysiology, and drug molecules and their metabolic products and nutrient molecules and their metabolic products. Similar to FFA and depending upon their solubility, a fraction of each metabolite is present as monomers in aqueous solution (either charged or neutral). We refer to this fraction as the unbound metabolite. For the purposes of the present disclosure, probes are fluorescently labeled proteins that reveal a measurable change in fluorescence upon binding to unbound metabolite.

For the purposes of the present disclosure, the term "lipid" is taken to have its usual and customary meaning and defines a chemical compound which is most soluble in an organic solvent but has some level of solubility in the aqueous phase (the fraction that is unbound). Accordingly, a "lipid-binding protein" includes any protein capable of binding a lipid as lipid is defined herein.

Levels of unbound molecules, such as for example lipids, hormones and metabolic products, can provide information diagnostic of health and disease when measured in appropriate human or animal fluids. It is increasingly apparent that determination of the unbound (a.k.a 'aqueous phase' or 'free') concentration of such molecules provides critical information about physiologic homeostasis. Many metabolites are hydrophobic molecules with low aqueous solubility and unbound concentrations that are much lower than their "total" concentration, where the bulk of the "total" may be bound to proteins or cells.

Intracellular lipid binding proteins (iLBP) are a family of low-molecular weight single chain polypeptides. There are four recognized subfamilies. Subfamily I contains proteins specific for vitamin A derivatives such as retinoic acid and retinol. Subfamily II contains proteins with specificities for bile acids, eiconsanoids, and heme. Subfamily III contains intestinal type fatty acid binding proteins (FABPs) and Subfamily IV contains all other types of fatty acid binding protein (Haunerland, et al. (2004) Progress in Lipid Research vol. 43: 328-349). The entire family is characterized by a common 3-dimensional fold. Ligand binding properties of the different subfamilies overlap considerably. The wild type proteins of subfamilies I (Richieri et al (2000) Biochemistry 39:7197-7204) and II both bind fatty acids and those of subfamily II bind fatty acids as well as their native ligands. Moreover, single amino acid substitutions are able to interconvert the ligand binding properties of proteins of subfamilies I and II (Jakoby et al (1993) Biochemistry 32:872-878).

U.S. Pat. No. 5,470,714 and U.S. Pat. No. 6,444,432, which are incorporated herein by reference, describe probes for the determination of unbound free fatty acids (FFAu). These probes were constructed using either native or mutant forms of proteins from the iLBP family. As discussed above, this family includes FABPs (Banaszak et al (1994) Adv. Protein Chem. 45:89-151; Bemlohr et al (1997) Ann. Rev. Nutrition, 17: 277-303). FABPs are intracellular proteins of approximately 15 kDa molecular weight and have a binding site that binds 1 or 2 FFA. Unfortunately, there is currently no way to determine the concentrations of different FFAu in mixtures of FFAu. Similarly, there are no general methods for determining the unbound concentrations of other important metabolites such as, for example other lipids, hormones, and drugs. This is largely due to the low concentration at which these components are present and their often poor solubility properties in aqueous solutions.

Unfortunately, despite the availability of protein structures and co-complex structures with ligands of interest, existing state of the art of molecular theory is not sufficient to design probes with the desired specificity and sensitivity de novo. Thus, extensive experimentation is typically required to find protein probes that not only bind with the desired specificity, but also produce a measurable signal indicative of ligand binding. Improving specificity and signaling through a completely random mutational strategy is not practical even for a small protein such as an FABP because a) there are $20^{131}$ possible mutants for a 131 residue FABP, and b) testing even a single probe using established state of the art methods requires extensive time (at least 2 weeks/probe) for purification, reaction chemistry and probe fluorescence response characterization.

Even if a more modest library of mutants is generated through random mutagenesis in specific regions of the protein, a method is needed to rapidly generate and screen the thousands of resulting mutant probes. Each mutant needs to be produced, and chemically reacted with a fluorescent group, in sufficient quantity to enable the measurement of its sensitivity and selectivity for many different ligands. It is also critical that the probes be as free as possible of contaminating proteins, unreacted fluorophore, and any other compounds that might interfere with sensitive fluorescence measurements. The development of a rapid, automated method for measuring and comparing probe responses to ligand is also critical. Embodiments of the invention described here satisfy these needs by disclosing "high throughput" methods for the rapid a) generation of large numbers of probes and the b) screening and characterization of these probes. An important aspect of this invention is that it allows the previous necessary and very time consuming step of characterization of ligand binding to the protein to be omitted; only the probe itself is characterized. This is important not only for the avoidance of the protein characterization step but also because the properties of the probe are often not predictable from the ligand-protein binding characteristics. For example, different proteins can have very similar binding affinities but the fluorescence response of their derivative probes can be quite different.

SUMMARY OF THE INVENTION

Embodiments of the invention are directed to high throughput methods for generating and screening of probes. Embodiments of the method may include one or more of the following steps:

generating polynucleotides encoding a protein library which includes an assortment of proteins which are mutations of a template protein capable of binding to a molecule of interest participating in a binding reaction;

expressing the proteins;

purifying the proteins by binding to a solid matrix;

associating the matrix bound proteins with fluorophores to produce probes;

retrieving the probes from the solid matrix; and screening the probes in a fluorometer in the presence and absence of the molecule.

In preferred embodiments, the template protein is non-enzymatic and the molecule is an unbound metabolite. Preferably, the template protein is an intracellular Lipid Binding Protein (iLBP). In some highly preferred embodiments, the template protein is a Fatty Acid Binding Protein (FABP).

Preferably, the template protein includes a cleavable or noncleavable affinity tag. In some preferred embodiments, the template protein includes a poly-histidine affinity tag and the solid matrix includes an immobilized metal chelate. In alternate preferred embodiments, the solid matrix includes an antibody specific for an epitope that lies outside the molecule binding region of the template protein.

In preferred embodiments, the fluorophore preferentially reacts with cysteine and lysine amino acid sidechains. More preferably, the fluorophore is acrylodan.

In preferred embodiments, the unbound metabolite is an unbound free fatty acid. More preferably, the free fatty acid is complexed with a carrier macromolecule which provides clamping of a level of unbound free fatty acid. Yet more preferably, the carrier macromolecule is albumin. Embodiments of the invention are also directed to probes produced by the high throughput screening methods described above.

Some preferred embodiments include comparing a ratio of fluorescence intensities of the probe at a first wavelength with that of the probe at a second wavelength in the presence and absence of the molecule.

In some preferred embodiments, probes with desirable characteristics are identified with the following steps:

determining a value for R by the following formula:

$$R = F_{\lambda 1}/F_{\lambda 2}$$

wherein $F_{\lambda 1}$ is a measured fluorescence intensity (intensity of a sample with probe present minus intensity of the sample without probe present) at a first emission wavelength, $F_{\lambda 2}$ is a measured fluorescence intensity (intensity of a sample with probe present minus intensity of the sample without probe present) at a second emission wavelength;

measuring the difference between R in the presence and absence of the molecule by the formula $$\Delta R = R_{+molecule} - R_0$$

wherein $R_{+molecule}$ is the ratio value for the measurement done in the presence of the molecule and $R_0$ is the ratio value for the measurement done in the absence of the molecule; and comparing $\Delta R$ for the probe to $\Delta R$reference for a standard.

Preferably, the standard is the template protein used to generate mutations for the high throughput screening. In some preferred embodiments, the standard is ADIFAB or ADIFAB2.

In some preferred embodiments, $\Delta R/\Delta R$reference is >0.1 and the molecule is a fatty acid. In alternate preferred embodiments, the $\Delta R/\Delta R$reference is <0.1 for unbound fatty acids but is >0.1 for an unbound metabolite that is not a fatty acid.

Embodiments of the invention are directed to methods for high throughput generating and screening of probes which may include one or more of the following steps:

generating a library of polynucleotides encoding affinity-tagged FABP muteins from a template FABP;

expressing the FABP muteins and tags;

purifying the FABP muteins by binding the tags to a solid matrix;

associating the FABP muteins with fluorophores to produce probes;

reformatting the probes in an array;

adding a sample which includes an unbound metabolite to be tested;

scanning the probes in a fluorometer in the presence and absence of the unbound metabolite to be tested; and comparing fluorescence of the probes in the presence and absence of the unbound metabolite.

In some preferred embodiments, the unbound metabolite is an unbound free fatty acid.

In preferred embodiments, associating the FABP muteins with the fluorophores is performed while the FABP muteins are bound to the solid matrix. In preferred embodiments, the fluorophore preferentially reacts with cysteine and lysine amino acid sidechains. More preferably, the fluorophore is acrylodan.

In some alternate embodiments, the following steps may be performed:

washing the bound FABP muteins;

removing the FABP muteins from the solid matrix; and reacting the unbound FABP muteins with fluorophores to produce probes.

In preferred embodiments, the high throughput screening methods may include comparing a fluorescence index, which may include changes in intensity, polarization and/or lifetime of the probe in the presence and absence of the unbound metabolite to be tested. Comparing the fluorescence index may also include comparing the fluorescence index of the probe at a first wavelength with that of the probe at a second wavelength in the presence and absence of the unbound FFA to be tested.

In preferred embodiments, the sample also includes a carrier macromolecule, whereby the carrier macromolecule complexes with the unbound metabolite to provide clamping. More preferably, the carrier macromolecule is albumin, lipid binding proteins, lipid vesicles or methyl-beta-cyclodextrin.

Embodiments of the invention are directed to probes produced by the high throughput screening methods described above. Preferred embodiments of the invention are directed to one or more probes which are those listed in Tables 3-7.

Embodiments of the invention are directed to methods to determine the concentration of unbound bilirubin in body fluids of a mammal which may include withdrawing a body fluid from the mammal; contacting the body fluid with a probe which is L2P14F7, L5P16H4, L1P1C12, L1P12E8 or L1P14D6; and determining the level of unbound bilirubin by measuring binding to the probe and comparing to a standard.

Embodiments of the invention are directed to methods for identifying individuals at high risk for disease which includes measuring unbound free fatty acids in the individual by using at least one probe selected from the probes listed in Tables 3-7 and comparing the unbound free fatty acid level in the individual to a level of unbound free fatty acid in a control population.

Embodiments of the invention are directed to methods of determining a profile of unbound metabolites in body fluids for an individual which includes measuring the concentrations of unbound metabolites with a combination of any of the probes described above. In preferred embodiments, the body fluid is whole blood, blood plasma, blood serum, urine, CSF, saliva, gastric juices, interstitial fluid, synovial fluid or lymph. In preferred embodiments, the unbound metabolite is an unbound free fatty acid.

Embodiments of the invention are directed to methods of determining the state of health or disease from an individual's unbound metabolite profile and may include determining an unbound metabolite profile for the individual; and determining that the profile is significantly different than an average profile of patients without the disease. In some preferred embodiments, the unbound metabolite is an unbound fatty acid.

Embodiments of the invention are directed to fluorescently labeled proteins based upon SEQ ID NO. 2 which include at least one additional mutation at a position(s) selected from positions 11, 14, 17, 18, 21, 23, 31, 34, 36, 38, 40, 47, 49, 51, 53, 55, 60, 62, 68, 70, 72, 73, 74, 78, 80, 82, 89, 91, 93, 102, 104, 106, 113, 115, 117, 119, and 126.

Embodiments of the invention are directed to fluorescently labeled mutants of a parent FABP shown as SEQ ID NO: 4. These fluorescently labeled mutant may have an altered spectral property when associated with an unbound free fatty acid when compared to the parent FABP shown as SEQ ID NO: 4. In preferred embodiments, the mutation includes a substitution.

Embodiments of the invention are directed to fluorescently labeled FABPs which include a mutation at position 72 of SEQ ID NO: 2 and at least one additional mutation at a position which is 11, 14, 17, 18, 21, 23, 31, 34, 36, 38, 40, 47, 49, 51, 53, 55, 60, 62, 68, 70, 73, 74, 78, 80, 82, 89, 91, 93, 102, 104, 106, 113, 115, 117, 119, or 126 and which has a value of $\Delta R/\Delta R_{ADIFAB2}$ with an unbound free fatty acid which is more than 0.1.

Embodiments of the invention are directed to functional engineered fluorescent proteins whose amino acid sequence includes an amino acid sequence of rat intestinal FABP with at least one amino acid substitution at a position which is 11, 14, 17, 18, 21, 23, 31, 34, 36, 38, 40, 47, 49, 51, 53, 55, 60, 62, 68, 70, 72, 73, 74, 78, 80, 82, 89, 91, 93, 102, 104, 106, 113, 115, 117, 119, or 126.

Embodiments of the invention are directed to polynucleotides which include a nucleotide sequence encoding a functional engineered protein which is (a) a protein that includes an amino acid sequence of rat intestinal FABP with at least one amino acid substitution at a position which is 11, 14, 17, 18, 21, 23, 31, 34, 36, 38, 40, 47, 49, 51, 53, 55, 60, 62, 68, 70, 72, 73, 74, 78, 80, 82, 89, 91, 93, 102, 104, 106, 113, 115, 117, 119, or 126 of SEQ ID NO: 4; or (b) a fluorescently labeled FABP with at least one mutation which has a value of $\Delta R/\Delta R_{ADIFAB2}$ with an unbound free fatty acid which is more than 0.1.

Embodiments of the invention are directed to expression vectors which include at least one expression control sequence operatively linked to a polynucleotide as described above. Embodiments of the invention are directed to recombinant host cells which include the expression vector described above. In some preferred embodiments, the recombinant host cell may be a prokaryotic cell. In alternate preferred embodiments, the recombinant host cell may be a eukaryotic cell.

Embodiments of the invention are directed to iLBPs capable of binding an unbound metabolite and having a value of $\Delta R/\Delta R_{ADIFAB2}$ with an unbound metabolite which is more than 0.1. In preferred embodiments the iLBP is an unbound fatty acid, an unbound bile acid or an unbound retinoic acid.

Embodiments of the invention are directed to an expression vector which includes a polynucleotide encoding an iLBP operably linked to at least one expression control sequence. Additional embodiments of the invention are directed to recombinant host cells which include expression vectors encoding an iLBP.

Embodiments of the invention are directed to methods of selecting probes which are capable of transport into a cell which may include the steps of adding a transport agent to a probe; assaying for transport of the probe into the cell; and selecting for probes that are internalized in the cell. In some preferred embodiments, the probe is specific for an unbound free fatty acid. In some preferred embodiments, the transport agent is a cationic lipid or peptide. In some preferred embodiments, the surface charge of the probe has been altered relative to the template protein.

Embodiments of the invention are directed to methods of drug discovery which include preparing an array of drugs to be tested, adding a probe, and assaying for binding between the drugs and the probe.

Embodiments of the invention are directed to methods of monitoring a drug therapy in a diseased patient over a treatment period which may include (a) withdrawing a body fluid from the patient; (b) measuring the binding of an unbound metabolite indicative of the disease to determine a level of the unbound metabolite in the body fluid with a probe; and (c) repeating steps (a) and (b) to measure the level of the unbound metabolite and thereby monitor the drug therapy through the treatment period.

Embodiments of the invention are directed to methods of measuring an amount of an unbound drug in a mammal which may include withdrawing a body fluid from the mammal; and measuring the binding of the drug or its metabolite to a probe thereby determining the amount of the unbound drug.

Embodiments of the invention are directed to methods for screening for an efficacy of a drug in a mammal which may include (a) determining a metabolic profile for the mammal; (b) administering a drug to be screened to the mammal; (c) repeating step (a); and (d) comparing the metabolic profile of step (a) with the metabolic profile of step (c) to determine the efficacy of the screened drug.

Embodiments of the invention are directed to methods of monitoring an effect of a nutrient in a mammal which may include the steps of (a) determining a metabolic profile for the mammal; (b) administering a nutrient to be monitored; (c) repeating step (a); and (d) comparing the metabolic profile of step (a) with the metabolic profile of step (c) to determine the effect of the nutrient.

Embodiments of the invention are directed to methods of classifying individuals which may include the steps of obtaining a metabolic profile for each individual to be classified; and grouping individuals based upon the metabolic profiles using principle cluster analysis.

Further aspects, features and advantages of this invention will become apparent from the detailed description of the preferred embodiments that follow.

DETAILED DESCRIPTION OF THE PREFERRED EMBODIMENT

Figure 1:
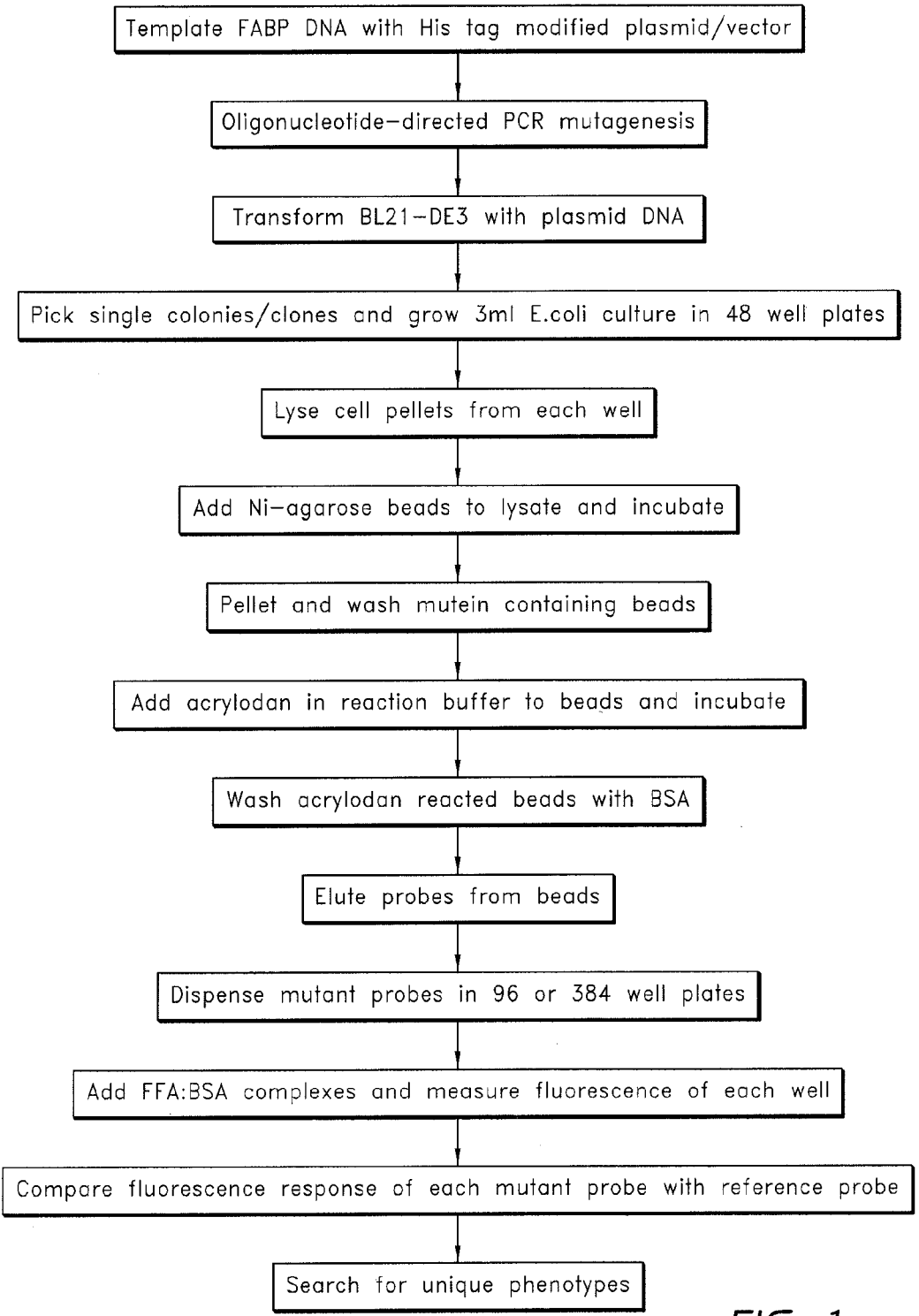
FIG. 1 shows a flow chart outlining a preferred embodiment of a method of probe production.

While the described embodiment represents the preferred embodiment of the present invention, it is to be understood that those skilled in the art can modify the process without departing from the spirit of the invention. Preferred embodiments of the present invention relate to the development of fluorescent molecules ("probes") that can be used to determine the concentration of unbound metabolites. More particularly, the invention relates to 1) high throughput methods to discover such probes, 2) the use of such probes for clinical medicine, drug development and basic science, 3) examples of the development of probes for the determination of the unbound concentration of specific free fatty acids, 4) the use of such probes to provide a profile of unbound metabolites for monitoring the states of health and disease for early diagnosis of human disease and for monitoring the effect of therapeutic intervention on the course of a condition or disease. Other uses include drug screening and monitoring the effect of a nutrient. It is noteworthy that for each probe described, there is cross reactivity between the various categories of metabolites. For example, a probe may bind strongly to retinoic acid but, still have some binding affinity for fatty acids. The probes according to embodiments of the invention find utility in identification and quantification of a wide range of metabolites.

Probes are proteins that have been 'labeled' through the covalent addition of a fluorescent molecule (fluorophore) to a specific site on the protein and that bind metabolites. Probes have the characteristic that their fluorescence changes in a measurable way when they bind metabolites. Different probes can be generated by mutating the starting (template) protein and labeling the mutated proteins (muteins) with a fluorophore. The ability of each such probe to respond to a particular metabolite (or analyte) can then be assessed by measuring the change in fluorescence upon addition of defined concentrations of the unbound metabolite.

Generating the Library

A library of proteins representing potential probes may be created by any means known in the art. In a preferred embodiment, a protein that is capable of binding one or more unbound metabolites may be used as a template for mutagenesis. In some preferred embodiments, the protein capable of binding one or more unbound metabolites includes serum albumins, acyl CoA binding proteins, phospholipid or glycolipid binding proteins, retinol/retinoic acid binding proteins, bile salt binding proteins, an antibody or a Fatty Acid Binding Protein (FABP). The protein may bind fatty acids, other metabolites or both fatty acids and other metabolites. Besides free fatty acids, possible metabolites include but are not limited to molecules such as drugs, drug metabolites, hormones, prostaglandins, leukotrienes, sphingosine, sphingolipids, phospholipids, glycolipids, cholesterol and cholesterol derivatives and other steroids, lipid-soluble vitamins, bile salts, enzyme cofactors, retinoids such as retinoic acid and retinal, heme and heme metabolites, amino acids, peptides, carbohydrates and multivalent ions.

In more preferred embodiments, an FABP gene, wild-type or mutant, is used as the initial template or starting point for mutagenesis. A collection of mutant FABP clones is generated from the template. In preferred embodiments, mutation involves one or more amino acid substitutions in the binding cavity or the helical cap of the FABP. In a preferred embodiment, a mutant Rat Intestinal Fatty Acid Binding Protein (rI-FABP), which has 131 amino acid residues, was used as the starting point for the mutagenesis.

In more preferred embodiments, sites that alter ligand binding are predominantly ones that are within the binding cavity or on the alpha helices that form the protein "cap" of the FABP. Sites that do not alter ligand binding are predominantly ones that are on the surface of the protein. In some embodiments, a library may be constructed by choosing among the sites that alter ligand binding and then applying random mutagenesis to those sites. Some single site mutants in the stated "cavity" or "cap" may not produce soluble protein or may fail to significantly affect binding. However, the same mutant, when combined with other mutations, may cause significant and favorable changes in ligand binding specificity. Such sites can also be selected experimentally as candidates for multi-site mutagenesis or library construction Any number of mutagenesis methods may be used to generate a collection or "library" of mutants, said mutagenesis methods include but are not limited to error-prone PCR, site-directed mutagenesis using defined or degenerate oligonucleotides, splicing by overlap extension (SOE), gene shuffling, or the use of mutator host strains. In preferred embodiments, an oligo-directed method of PCR-based mutagenesis was used to generate a collection or "library" of mutants. However, as far as the screening is concerned, it doesn't matter whether the library is composed of known, specific site-directed mutants or an "unknown" random assortment of mutants. Both types of libraries are screened with the same efficiency.

In preferred embodiments, oligos specifying desired mutations prime an enzymatic copying of the vector containing the template gene. The oligo, and therefore the desired mutation(s), is incorporated into the new copy of the gene. The sites mutated in the multi-site mutagenesis libraries of the preferred embodiments are those that were found to alter ligand-binding properties in a library of single point mutants.

Mutant genes are introduced into an organism capable of producing soluble protein from the mutant gene. Any type of organism can be used as long as soluble protein can be harvested from the lysed cells or the cell growth medium. For example, bacteria are used for protein expression in the preferred embodiment, but one skilled in the art could also express the protein in yeast, insect or other eukaryotic cells.

Producing the Probes

Protein purification is accomplished by incubating lysate from each clone with a solid support to which the protein is specifically bound with high affinity. There are two ways to make the protein associate with a solid support: a) the protein can be changed to increase its affinity for a solid support or b) the support can be modified to increase its affinity for the protein. The latter can be accomplished, for example, by immobilizing antibodies on the solid support, said antibodies having a high binding-affinity for the protein of interest.

Alternatively the protein may be "tagged" so that it binds to the column material with high affinity. This includes but is not limited to tagging with biotin, Flag-epitope or c-myc epitope or HA-tag, glutathione-S-transferase (GST), maltose binding protein (MBP), a chitin binding domain (CBD), Thioredoxin, β-Galactosidase, VSV-Glycoprotein, calmodulin binding protein, or a metal affinity tag such as a 6× His tag. Preferably, the fusion partner does not change the FABP fatty acid binding properties. The specific association of the affinity tag with the solid support material enables single step purification of the protein of interest from the lysate, which contains thousands of other contaminating proteins and other substances. The affinity tag(s) may be fused at either the NH2- or COOH-termini or at both termini simultaneously. In a preferred embodiment, a 6× Histidine tag was fused to either the FABP $NH_2$- or COOH-termini or at both termini simultaneously without significantly changing the protein's fatty acid binding properties. These fusion proteins can be reversibly immobilized on a solid support for protein purification, delipidation and probe production.

Before now, muteins with potentially interesting binding properties were purified with the protein in the mobile, aqueous phase. Protein purification and delipidation required passing the mutein through various types of 'standard' purification matrices (i.e. size exclusion chromatography, ion exchange chromatography, hydrophobic interaction chromatography (HIC)). The resulting purified and delipidated protein then underwent a buffer exchange process to place it in the fluorophore reaction buffer. After the labeling reaction, the labeled protein was subjected to several HIC chromatography steps to remove unreacted fluorophore. The probe production process, with its intrinsic protein handling losses, and the subsequent assay procedure required the production of milligram quantities (>5 mg) of each mutein. Protein production typically required at least one week per mutein per person and the labeling process required an additional week. Because synthesis of the labeled probe required a significant additional investment of time and money, muteins were only reacted with fluorophore if the binding properties of the unlabeled protein looked promising.

In the new process described here, the muteins are affinity purified and left on the affinity purification matrix, essentially making the protein part of the solid phase. Chemical functionalities required for delipidation, labeling, and removal of unreacted label are passed over the protein/solid phase. This is the opposite of the current state of the art process. This new approach enables one person, with minimal automation, to produce approximately 800 labeled muteins in approximately 6 hours. Since we are assaying the probe directly, rather than an unlabeled protein indirectly, the signal is much stronger and very small quantities of probe are required (<8 μg).

By this method a large number of muteins may be constructed, purified, fluorescently labeled and the probes screened for ligand binding in a high throughput format. In a preferred embodiment, the cell growth, cell lysis, protein purification, fluorescent labeling, and probe purification is done in multiwell plates. Preferably, the plates have from 1 to 1536 wells and each well has a volume of between 0.002 ml to 10 ml. By this method, probes may be generated which have different fluorescent responses to different fatty acids or other metabolites as compared to the response of the template. For example, the probe variants may each have different fluorescence spectra and/or different fluorescence intensity at a given emission wavelength when bound to a particular fatty acid as compared to the parent template.

In preferred embodiments, the protein variants are labeled with acrylodan while still bound to the solid support. However other fluorescent labels may also be used such as but not limited to danzyl aziridine, 4-[N-[(2-iodoacetoxy)ethyl]-N-methylamino]-7-nitrobenz-2-oxa-1,3-diazole ester (IANBDE), and 4-[N-[(2-iodoacetoxy)ethyl]-N-methylamino-7-nitrobenz-2-oxa-1,3-diazole (IANBDA). Other protein probes that bind unbound metabolites such as unbound FFA and that change their fluorescence upon binding may also be used including, but not limited to, albumin. Albumin with a fluorescent label such as 7-hydroxycoumarin or anthraniloyl changes its fluorescence upon binding FFA (Demant, E, Anal. Biochem. (1999) 267:366-372, Massey, J. B., et al Biophys. J. (1996) 72:1732-1743). Any fluorescent label may be used in the practice of the invention as long as a measurable difference may be detected upon binding of a free fatty acid or other analytes.

In a preferred embodiment, the template FABP is recombinant rat intestinal fatty acid binding protein (rI-FABP). Derivatization with acrylodan is performed using known methods substantially as previously described (U.S. Pat. No. 5,470,714 & Richieri, G. V, et al., J. Biol. Chem., (1992) 276: 23495-23501), and the resulting probe (ADIFAB) is commercially available (FFA Sciences LLC, San Diego, Calif.). A different fluorescence is exhibited by ADIFAB when FFA is bound and the concentration of FFAu can be determined from the change in fluorescence. The wavelength emitted by the fluorescently-labeled FABP depends upon the label and protein used. In an alternate preferred embodiment, the template protein is rI-FABP that has Ala substituted for Leu at position 72 (rI-FABP-L72A) with the resulting probe named ADIFAB2. The binding affinities of ADIFAB2 have been found to be about 10-fold greater than ADIFAB. ADIFAB2 also has an altered spectral response, making it especially useful for measurements of FFAu in blood samples (Apple et al, Clinical Proteomics, (2004) 1:41-44, U.S. patent application Ser. No. 10/670,958). The wavelengths at the maximum intensities emitted by these fluorescently-labeled I-FABP's in the absence of FFA is about 420 to 480 nm. The emission wavelengths at the maximum intensities emitted by these fluorescently-labeled I-FABP's with FFA bound is about 495 to 580 nm. Experiments typically involve measuring the fluorescence response within both emission maxima or at wavelengths for which the effect of interfering molecules such as hemoglobin can be eliminated as described in (U.S. application Ser. No. 10/670,958 and PCT/US2004/030521) and the calculation of the ratio 'R' of the two fluorescence intensities. The baseline value for this ratio, measured in the absence of analyte, is designated R0.

Probes produced according to some embodiments of the invention have altered specificity for different FFAu or different unbound metabolites relative to the ADIFAB and ADIFAB2 probes made from the preferred templates-. Altered specificity refers to an alteration in the fluorescence change that occurs when the probe is exposed to different unbound metabolites or different molecular species of FFAu (for example different chain lengths and/or different numbers of double bond and/or different rotational isomers about a given double bond and/or different locations of double bonds.) For example, ADIFAB2 might reveal, when exposed to a particular FFAu1 at a concentration of [FFAu1], a change (ΔR1) in the value of the ratio R relative to R0. Exposing ADIFAB2 to n such FFAu would reveal a set of responses, $\{\Delta Ri\}=\Delta R1, \Delta R2, \ldots \Delta Rn$. A probe with altered specificities would possess a different set of responses to the same FFAu and concentrations; $\{\Delta Ri'\}=\Delta R1', \Delta R2', \ldots \Delta Rn'$. With sufficient numbers of different probes possessing different responses it would be possible by measuring the response of each probe to a sample containing mixtures of different FFAu and/or different unbound metabolites, to determine the concentration of each different FFAu and/or different unbound metabolites. Because different states of health and disease might alter the distribution of different FFAu and/or different unbound metabolites in a variety of body fluids including but not limited to whole blood, blood plasma, blood serum, urine, CSF, saliva, gastric juices, interstitial fluid, synoidal fluid or lymph, it can be expected that such a determination would provide valuable information about health status. In addition, such measurements would provide valuable tools for basic research and drug discovery.

Screening the Probes

In some embodiments, aliquots of the probes prepared as described above are placed in multi-well plates, suitable for fluorescence measurements. Defined amounts of ligands are added to each well and a fluorescence signal from the wells containing probe and ligand are compared to wells containing only the probe. The values obtained are compared with those of a 'reference' probe. The ligands may be fatty acids or other unbound metabolites. Preferably, the number of wells in the multiwell plate is between 1 and 1536. Preferably, at least some of the reagents are added to the plates using robotic liquid handling systems. Preferably, the fluorescence signal is measured from each well with a fluorescence plate reader to determine if the signals of each probe are significantly different than those of the parent probe.

The intensity ratio ("R" value) for a given probe is determined. The ratio is calculated using the following formula:

$$R=F_{\lambda 1}/F_{\lambda 2}$$

wherein, $F_{\lambda 1}$ is the measured fluorescence intensities (intensity of sample with probe present minus intensity of sample without probe present) at wavelength 1 and $F_{\lambda 2}$ is the measured fluorescence intensities (intensity of sample with probe present minus intensity of sample without probe present) at wavelength 2. Then, for a given probe, $\Delta R$, the difference in R value between the measurement in the presence of the analyte and in the absence of the analyte, is calculated as follows:

$$\Delta R=R_{+analyte}-R_0$$

The $\Delta R$ value for a given probe is then compared to a reference probe, for example, ADIFAB or ADIFAB2, by $\Delta R/\Delta R_{reference}$. This value is an indication of how dissimilar the new probe (derived by mutation of the template) is to the reference. By this method, probes with new and useful characteristics may be identified. Measurements of fluorescence intensities are obtained using standard techniques.

Preferably, the fluorescence intensities at two or more wavelengths are measured in each well and the intensity ratios at all combinations of the two or more wavelengths are evaluated to determine if the ratios of each probe are significantly different than those of the reference probe. By this method, probes may be identified that have different specificities in their fluorescence response to different ligands as compared to the reference probe. In preferred embodiments, the ligands are unbound free fatty acids. Other methods for comparing changes in fluorescence with and without analyte can also be used.

In some embodiments of the invention, the probes are screened for their ability to be transported into a cell. The cell may be procaryotic or eukarotic. Preferably, the cell is a mammalian cell.

Cell transport may be facilitated by the use of a transport agent, such as a cationic lipid or cationic polymer or peptides. Such cationic lipid transport agents are well known and include, for example, Lipofectamine 2000® (Invitrogen) and peptides include Chariot™ (Active Motif®).

In preferred embodiments, the transport agent is mixed with the probe and the complex is incubated with cells which have been cultured on a suitable media. After incubation for a suitable period of time, the cells are washed and the ability of the probe to be transported into the cell may be determined by observation under a fluorescence microscope.

In some embodiments, the surface charge of the probe may be altered relative to the template protein to improve the transfection efficiency.

Using the Probes

A collection of probes with distinct signaling properties can be used to determine the concentrations of different unbound metabolites in a mixture, for example the concentrations of different unbound free fatty acids in a mixture. Thus, an unbound metabolite and/or an unbound free fatty acid profile can be determined for an individual. The most complete profile for fatty acids is the enumeration of the concentrations of each of the unbound free fatty acids in a mixture. This type of profile will require at least n different probes for n fatty acids. Less detailed, but very informative profiles, such as the enumeration of the fractions of different fatty acid classes, can be determined with fewer distinct probes (n probes for n classes). Classes of unbound free fatty acids include saturated, unsaturated, monounsaturated, polyunsaturated, short chain, medium chain, long chain and very long chain. In a preferred embodiment, the concentration of each type of unbound FFA in a mixture is determined. In another preferred embodiment, the fraction of unbound FFA that are unsaturated is determined. In another preferred embodiment, the fraction of FFAu that are monounsaturated is determined. In another preferred embodiment, the fraction of FFAu that are polyunsaturated is determined. In another preferred embodiment, the fraction of FFAu that are saturated is determined. In another preferred embodiment, the fraction of FFAu that are short chain (4-8 Carbon length) is determined. In another preferred embodiment, the fraction of FFAu that are medium chain (10-14 Carbon length) is determined. In another preferred embodiment, the fraction of FFAu that are long chain (16+ Carbon length) is determined. In another preferred embodiment, the fraction of FFAu that are very long chain (20+ Carbon length) is determined. Such determinations are used to generate, for any individual, a profile of unbound FFA that is useful in the diagnosis of disease and the determination of risk factors for disease. Such diseases include but are not limited to cardiac disease, stroke, neurological diseases such as dementia and Alzheimer's disease, diabetes, inflammatory diseases and certain cancers.

DNA and protein sequences for Fatty Acid Binding Proteins (FABPs) are shown in the sequence listing. SEQ ID NO: 1 shows the cDNA sequence for the wild-type rat intestinal Fatty Acid Binding Protein (rIFABP). The rat fatty acid binding protein is post-translationally modified in the rat, with the modifications including the removal of the N-terminal methionine and the acetylation of the "new" N-terminal residue Ala. Protein sequences are numbered starting with the first residue of the mature protein. Thus, Ala is residue 1 in the corresponding protein shown as SEQ ID NO: 2.

SEQ ID NO: 3 shows a preferred template rI-FABP-L72A DNA sequence according to the invention. SEQ ID NO: 4 shows the corresponding protein sequence. In this preferred embodiment, the protein has a substitution of alanine at position 72. Other preferred species which are derived from the protein shown as SEQ ID NO: 4 the probes listed in Tables 3, 4, 5, 6, 7 and 8.

In preferred embodiments of the invention, the sample used for the determination of unbound FFA is a fluid sample derived from a human, an animal or a plant. Preferably, the fluid is whole blood, blood plasma, blood serum, urine, CSF, saliva, gastric juices, interstitial fluid or lymph. In some embodiments, unbound metabolites such as unbound FFA are extracted from tissue samples by means known in the art. In other embodiments determination of unbound metabolites such as unbound FFA is performed within the cytoplasm of a cell by microinjecting or otherwise transfecting the probe into the cell. Unbound metabolites include but are not limited to unbound FFA, drugs, drug metabolites, hormones, prostaglandins, leukotrienes, sphingosine, sphingolipids, phospholipids, glycolipids, cholesterol and cholesterol derivatives and other steroids, lipid-soluble vitamins bile salts, enzyme cofactors, retinoids such as retinoic acid and retinal, heme and heme metabolites, amino acids, peptides, carbohydrates and multivalent ions. As discussed above, classes of unbound free fatty acids include saturated, unsaturated, monounsaturated, polyunsaturated, short chain, medium chain and long chain.

A normal range for a given unbound metabolite is determined from a healthy population and deviations from this normal range may indicate disease. For example, elevated levels of unbound FFA are indicative of cardiac disease. In some embodiments, a metabolic profile is determined for an individual using more than one probe to determine levels of more than one unbound metabolite. Metabolic profiles from a normal, healthy population will be determined. Deviations from a normal metabolic profile are indicative of disease, nutrient deficiency, exposure to toxins or carcinogens and the like.

In some embodiments, probes produced as described above are used to determine the effect of a drug on a known metabolic profile. The metabolic profile is determined for a test population which may be a normal or non-normal population such as a diseased population. For example, a metabolic profile may be determined for a diseased test population. The diseased test population could then be treated with a drug for a predetermined period of time. The metabolic profile is then redetermined for the test population after drug treatment to observe the effect of the drug on the metabolic profile. In some cases, a change in the metabolic profile may be undesirable, for example, if testing a drug for toxicity and/or unwanted side effects. In other embodiments, a change in metabolic profile may indicate the effectiveness of the drug tested.

In some embodiments, a drug therapy in a diseased patient is monitored using one or more probes prepared according to the invention. For example, a body fluid may be withdrawn from the patient. Binding of an unbound metabolite indicative of a disease may be tested using at least one probe produced as described herein. An abnormal level of one or more unbound metabolites is an indicator of a disease state. For example, elevated free fatty acids are risk factors and indicators of cardiovascular disease; deficiencies in vitamins B6 and folic acid have also been associated with cardiovascular disease and cancer. Levels of the unbound form of these metabolites may be measured or monitored according to the invention using probes generated as described herein.

In some embodiments, the metabolic profile may be used to determine the effect of specific nutrients on an individual. A metabolic profile may be used to indicate a nutrient deficiency.

In some embodiments, a metabolic profile may be used to classify individuals into different categories having different susceptibilities to different drugs and/or nutrients. In preferred embodiments, principal component analysis may be used to cluster unbound metabolite profiles into defined groups.

EXAMPLE 1

Specific point mutations were made at thirty-five sites within the rI-FABP-L72A fatty acid binding pocket, with up to 19 different amino acid residues substituted for the native amino acid at each site. Each mutein contained one substitution. Sites that appeared to produce interesting modifications were used as the starting point for further mutagenesis studies (See Example 2). Mutagenesis was carried out as follows.

The rI-FABP-L72A open reading frame (ORF) was cloned into a modified pET-11d plasmid/vector (Novagen) at a site that resulted in the fusion of a 6-His affinity tag to the protein COOH-terminus. This template DNA was propagated in *E. coli* strain XL10-Gold (Stratagene). Purification of the template followed standard protocols (Sambrook et al., 1989). The template genes used in other screening examples also encode COOH-terminal 6-His fusions. We have found that the affinity tag can be fused to the $NH_2$-terminus, the COOH-terminus or both termini of the rI-FABP protein without significantly changing the FFA binding characteristics of the protein.

Mutant proteins were generated using an oligonucleotide-directed method of PCR-based mutagenesis. Oligonucleotides (oligos) of our design were purchased from QIAGEN. Oligonucleotide primers incorporating the desired mutation(s) were designed with an average length of 33 bases, with 15 bases on each side of the codon for the amino acid to be mutated. The calculated melting temperatures for oligo-template dimers ranged from 60 to 75° C. Mutagenesis reactions for single point mutations utilized single oligos. Reactions to generate multiple possible substitutions at one or multiple sites utilized approximately equimolar amounts of multiple oligos.

Mutagenic oligos were phosphorylated at their 5' ends with T4 polynucleotide kinase (New England Biolabs, NEB) to allow for ligation during the mutagenesis reaction. Phosphorylation was carried out in a 50 μL reaction mixture containing the following reagents:
 1. 300 pmol of oligonucleotide
 2. 1 mM ATP
 3. 1× T4 polynucleotide kinase reaction buffer (NEB)
    i. 70 mM Tris-HCl (pH 7.6)
    ii. 10 mM $MgCl_2$
    iii. 5 mM dithiothreitol
 4. 10 units of T4 polynucleotide kinase.

The reaction mixture was incubated at 37° C. for 30 min. followed by 20 min. incubation at 65° C. to deactivate the T4 polynucleotide kinase.

Mutant, single-stranded, closed-circle copies of the template protein orf in the pET-11d vector were synthesized in 50 μL PCR reactions containing the following reagents:
 1. 100 ng of vector containing rIFABP template gene.
 2. 10 pmoles 5' of each phosphorylated mutagenic primer.
 3. 5 units of thermostable DNA polymerase.
 4. 20 units of thermostable ligase.
 5. 10 nmoles of each dNTP (dATP, dCTP, dGTP, dTTP).

6. 0.5× thermostable DNA polymerase buffer
   a. 10 mM Tris-HCl, pH8.0
   b. 5 mM KCl
   c. 5 mM (NH$_4$)SO$_4$
   d. 1 mM MgSO$_4$
   e. 0.5% Triton X-100
   f. 50 µg/ml BSA
7. 0.5× thermostable ligase buffer
   a. 10 mM Tris-HCl, pH 7.6
   b. 12.5 mM potassium acetate
   c. 5 mM magnesium acetate
   d. 5 mM DTT
   e. 0.5 mM NAD
   f. 0.05% Triton X-100.

The PCR reactions utilized the following thermal cycler program:
1. 45° C. for 15 minutes (to allow ligase to repair any nicks in DNA template).
2. 95° C. for 2 minutes (activate polymerase and denature template strands).
3. The following sequence is repeated 30 times:
   a. 95° C. 30 seconds (denaturation)
   b. 55° C. for 45 seconds (anneal mutagenic primers to DNA template)
   c. 68° C. for 14 minutes (DNA synthesis and ligation)
   d. 45° C. for 5 minutes (extended time for ligase to close any gaps).
4. 72° C. for 20 minutes (extend all newly synthesized DNA to full length)
5. 45° C. for 15 minutes (allow ligase to close any gaps)

Upon completion of PCR mutagenesis, the reaction mixture was treated with the restriction enzyme DpnI in an attempt to destroy the methylated wild-type template DNA strands. The reaction mixture was subsequently used to transform *E. coli* strain XL10-Gold (Stratagene). For site-specific mutants, clones (colonies) were picked and the presence of the mutation was verified by sequencing or by PCR with oligos designed to hybridize effectively with only the wild-type sequence. For libraries of clones with randomized multiple mutations, all of the XL-10 Gold colonies resulting from transformation with the mutagenesis reaction were utilized. Plasmid DNA was isolated from individual clones (site-specific mutagenesis) or a mixture of clones (multi-mutant libraries) and transformed into the *E. coli* strain BL21-DE3 (Novagen). Synthesis of the mutant protein was induced in 3 ml Luria broth (LB) cultures of single colonies by adding isopropyl-beta-D-thiogalactopyranoside (IPTG) to a final concentration of 0.4 mM. These cultures were grown and harvested in 48 position 5 ml rectangular well plates (Innovative Microplates). Induction periods ranged from 2 to 12 hours at 37° C. Cells were harvested by centrifugation and the cell pellets stored in the plates at −80° C.

Cell pellets from induced cultures were lysed to release the protein. The 48-well plates were removed from −80° C. storage and the cell pellets thawed by floating the plates in a room temperature water bath. A 400 µl aliquot of lysis buffer was added to each well to disperse and lyse the cells. Lysis buffer has the following composition:
1. 50 mM Tris-HCl, pH 8.0
2. 250 mM NaCl
3. 5 mM MgSO$_4$
4. 5 mM KCl
5. 0.5 ml/ml lysozyme
6. 10 µg/ml Dnase I
7. 10 µM essentially fatty acid free BSA (Sigma, A6003)

Plates were then subjected to two cycles of freezing and thawing, with freezing occurring in liquid nitrogen and thawing in the room-temperature water bath. Lysates were clarified by centrifugation and the supernatants transferred to 96 position 2.2 ml rectangular well plates (ABgene).

Affinity Purification and Delipidation of the FABP Muteins

Approximately 120 µl of 25% (v/v) Ni-agarose (Sigma His-Select HC, P-6611) suspension was added to each well and the plates sealed with 96-position cap sealing mats (Abgene). Plates were incubated at 4° C. for 30 minutes with end-over-end mixing. Beads were pelleted by centrifugation and the supernatants removed by aspiration. The FABP muteins are selectively retained by the Ni-agarose, resulting in a single step purification of the desired proteins.

Each bed of Ni-agarose beads was washed once with Wash Buffer I, which has the following components:
1. 50 mM Tris, pH 8.0
2. 200 mM NaCl
3. 15 uM essentially fatty acid free bovine serum albumin (BSA)
4. 10 mM imidazole.

The bovine serum albumin component of the buffer delipidates the FABPs. A failure to fully delipidate the muteins typically results in poor labeling efficiency with the fluorophore. The wash process involved adding 1.5 ml of Wash Buffer I to each bead bed, making sure the beads were well dispersed, sealing the plate with a cap mat, gently shaking the plate, pelleting the Ni-agarose by centrifugation, and removing the supernatant by aspiration.

Each bed of Ni-agarose beads was then washed three times with 1.5 ml aliquots of Bis-Tris-Propane (BTP) Buffer to remove any residual BSA and to place the protein in the proper buffer for the fluorophore labeling reaction. The BTP Buffer is pre-heated to 37° C. because the subsequent reaction with fluorophore is carried out at 37° C. Bis-Tris-Propane Buffer has the following composition:
1. 10 mM Bis-Tris-Propane, pH 9.3
2. 100 mM NaCl.

Each wash step with BTP Buffer has the same buffer addition, mixing, centrifugation and aspiration steps as described above for washing with Wash Buffer I. The protein was then ready for reaction with the fluorophore.

Reaction of FABP Muteins with the Fluorophore

A 470 µl aliquot of pre-warmed Bis-Tris-Propane Buffer was added to each bead bed (~30 µl). A 5 µl aliquot of 20 mM acrylodan stock (20 mM in dimethylformamide) was then added to each sample, the plate sealed with a cap mat, and the plate was shaken to rapidly mix the contents. Plates were gently mixed end-over-end in a 37° C. incubator for 60 minutes. Post-incubation plates were centrifuged to pellet the agarose beads and the supernatants discarded through aspiration. Residual unreacted acrylodan was largely removed by washing each bead bed with a 1.5 ml aliquot of Wash Buffer II:
1. 50 mM Tris, pH 8.0
2. 200 mM NaCl
3. 15 µM essentially fatty acid free BSA.

The BSA component of Wash Buffer II binds to acrylodan. Residual BSA and acrylodan were removed by washing each bead bed with three 1.5 ml aliquots of Wash Buffer III:
1. 10 mM Tris, pH 8.0
2. 200 mM NaCl Labeled mutein probes were released from the Ni-agarose beads by adding 300 µl of Elution Buffer to each bead bed and gently mixing end-over-end for 20 minutes at room temperature. Elution Buffer had the following composition:
1. 0.85×HEPES buffer
2. 75 mM EDTA The probe concentration for each mutein supernatant in the plate was estimated with the Bradford protein assay (Bio-Rad).

Mutant probes were screened in 96-well plates by fluorescence response to five fatty acids: arachidonate, linolenate, linoleate, oleate, and palmitate. Each fatty acid was prepared as a complex with BSA by slow addition of 50 mM stocks of fatty acid sodium salts at pH 11 to 600 µM BSA in HEPES buffer. During the formation of complexes, 15 µL aliquots were periodically measured with the reference probe, ADIFAB2, to determine the ΔR value upon excitation at 375 nm and fluorescence emission at 550 and 457 nm using a Fluorolog-3 spectrofluorometer (Jobin Yvon) (Richieri et al, Molecular and Cellular Biochemistry (1999), 192:87-94 & Richieri et al, J. Biol. Chem. (1996), 271:31068-31074). Complexes were prepared such that the final ΔR was approximately 0.4 which correspond to [FFAu] ranging from 100 to 1000 nM depending on FFA type. These complexes buffer or clamp the FFAu levels at fixed values and therefore ensure the accurate comparison of different probes with the same FFAu concentrations. In contrast, addition of FFAu alone (i.e. uncomplexed FFA) introduces considerable uncertainty in comparing different probes because the FFAu level will be affected by binding to the dispensing device, the walls of the multi-well plates and to the probe itself. Thus, the terms "buffer" and "clamp" as used in this particular context herein are taken to mean the ability of a carrier macromolecule to complex with an unbound metabolite so that the unbound metabolite is presented accurately for measurement purposes and is prevented from non-specific binding such as binding to laboratory apparatus.

Plates were prepared and read in two stages. First, complexes and fatty acid free BSA were diluted to 6 µM BSA in HEPES and added to the 96-well plate at 300 µL per well. A MultiProbe II HT (Perkin Elmer) (an automated liquid handling system) was used to facilitate plate preparation for high throughput screening, but any automated or manual pipetting system will suffice. The background fluorescence was then measured at the same wavelengths as used for ADIFAB2 using a Fluorolog-3 spectrofluorometer with an external Micromax 384 fluorescence plate reader (Jobin Yvon). In the second stage, 30 µL aliquots of the mutant probes were added to multiple wells of the plate, one for each fatty acid and one with fatty acid free BSA only, and the fluorescence intensity at each wavelength was again measured on the plate reader. After subtraction of the background fluorescence, the fluorescence ratio of each well was calculated.

The fluorescence response was quantitatively compared to ADIFAB2 to search for changes in magnitude and fatty acid profile; for example the response to one fatty acid relative to another. For each probe the ratio differences (ΔR) between wells with each fatty acid compared to a corresponding well with fatty acid free BSA were recorded. The relative response compared to ADIFAB2 was calculated by dividing ΔR for each fatty acid by that for ADIFAB2 (ΔR/ΔRAD2). Probes that show large (ΔR/ΔRAD2) and different (ΔR/ΔRAD2) for different fatty acids were chosen for larger scale production and calibration. The methods described above can be used to screen other fatty acids and/or other unbound metabolites using other plate readers. We have attained equivalent results, for example, using the Gemini EM dedicated fluorescence plate reader (Molecular Devices).

EXAMPLE 2

Four amino acid positions Y14, L38, L72, and Y117 of the L72A mutant of rI-FABP shown as SEQ ID NO: 4 were chosen for simultaneous, random mutagenesis. At each position, the native amino acid was potentially replaced with one of 8 other non-native amino acids. This meant that there were nine possible outcomes at each position:G, A, V, I, L, M, F, Y or W. The mutagenesis reaction for this library was carried out essentially as described in EXAMPLE 1. In this case, oligos for changing each of the four positions to the 8 different non-native amino acids (i.e. 32 oligos of equimolar amounts) were added to the mutagenesis reaction simultaneously. *E. coli* strain XL-10 Gold was transformed using the mutagenesis reaction and all of the resulting colonies pooled for the isolation of plasmid (Sambrook et al., 1989). The isolated plasmid mixture represented the DNA form of the library. An aliquot of library DNA was used to transform the *E. coli* expression strain BL21-(DE3). Mutant proteins were expressed, purified and labeled as described in Example 1. Over 3000 BL21(DE3) clones were picked and screened from this library. Similarly, a second library containing G, A, V, I, L, M, F, Y and W amino acid substitutions at positions M18, G31, F55, A73 of the L72A mutant of rI-FABP were constructed and approximately 3000 mutant clones screened.

Screening was conducted by evaluating ΔR/ΔRreference as described in paragraphs 0053-0055 and Example 1 for the following fatty acids: palmitate, palmitoleate, stearate, oleate, linoleate, linolenate and arachidonate, where the reference was to ADIFAB2. The screening rate was increased by use of 384 well plates. In this case the total well volume was reduced to 100 µL and the volume of probe used per well was 10 µL. Because the identity of each mutant probe was unknown in this example, the probes of interest were organized according to phenotype. Typically, phenotypic clusters could be generated by grouping unknown probes that gave Ro and ΔR/ΔRAD2 values within 10 to 20% of each other. Example phenotypes from the 3000 clones screened from the second library are shown in Table 1. The clone ID specifies the second library and well position of each clone. The fluorescence ratio for zero FFAu concentration (Ro) is shown in the second column. The remaining 7 columns are the ratios of the fluorescence response (R-Ro) for each probe relative to ADIFAB2 for arachidonate, linolenate, linoleate, oleate, palmitate, palmitoleate and stearate. The phenotypes of these probes reveal, relative to ADIFAB2, one with a large response to POA but smaller ones for OA and SA (L2P21H1), one with a response only for AA and SA (L2P12G9), one with greater response for all 7 FFA (L2P21C1), one with a distinct preference for PA (L2P14F12) and one with little or no response to any of the 7 FFA. It is apparent that such a table with thousands of mutein probe results can be searched for any desired phenotype using an appropriate method of query.

TABLE 1

Example clones from screening of second library

| | | ΔR/ΔR$_{AD2}$ | | | | | | |
|---|---|---|---|---|---|---|---|---|
| CLONE ID | Ro | AA | LNA | LA | OA | PA | POA | SA |
| L2P21 H1 | 0.30 | 1.02 | 1.80 | 1.20 | 0.55 | 1.21 | 2.49 | 0.39 |
| L2P12 G9 | 0.45 | 0.54 | 0.01 | −0.07 | 0.07 | 0.03 | −0.01 | 0.48 |
| L2P21 C1 | 0.39 | 3.27 | 3.73 | 4.04 | 3.20 | 2.54 | 3.52 | 2.02 |
| L2P14 F12 | 0.42 | 0.47 | 0.72 | 0.54 | 0.41 | 1.09 | 0.66 | 0.29 |
| L2P3 C7 | 0.10 | 0.03 | 0.04 | 0.04 | 0.02 | 0.03 | 0.05 | 0.02 |

A strategy was also developed to improve upon "hits" from our primary screening. We have observed that some mutations, when present, create a bias towards distinct phenotypes of mutein probes. While one cannot expect the effects of independently assayed mutations to be simply additive when combined, the signaling or binding characteristics of some mutations are carried through when present in new mutant combinations. This makes it possible to arrive at the desired probe properties through iterations of screening, with the most desirable mutations observed in one library incorporated into the template for the next library. For example, a given library might produce several clones with a desired binding property such as low response to a given FFA or high dynamic range. Sequencing these 'interesting' clones enables one to identify whether a specific mutation is favoring the desired phenotype. If so, the mutation is incorporated into the template for the next round of mutagenesis and the new library is essentially a search for additional phenotypic improvements through synergy with substitutions at other amino acid positions.

For each probe considered to have a useful phenotype, the sequence is determined, milligram quantities of the probe are prepared and the probe is calibrated. Calibration of a new probe involves quantification of the fluorescence response to varying levels of fatty acids from zero to probe saturation. Spectra of probes were analyzed for true ratio behavior. Binding affinities (e.g. dissociation constant, Kd) and fluorescence parameters were quantified by measuring the fluorescence ratio upon straight titration with fatty acids and titration with fatty acid complexes with known unbound concentrations as determined with ADIFAB (see Richieri et al, Molecular and Cellular Biochemistry (1999), 192:87-94). Using calibration constants, the probe behavior was compared to the initial screen to check for desired properties.

EXAMPLE 3

Two probes, ADIFAB2 (AD2) and L72V R106Q R126Q (VQQ), were used to determined the concentrations of arachidonic (AA) and palmitic (PA) acids in a prepared mixture of these fatty acids complexed with BSA. Probe VQQ has the unique property that it does not respond to palmitic acid. Four complexes were made as outlined in Example 1: (1) AA:BSA with 50 nM free AA, (2) AA:BSA with 200 nM free AA, (3) PA:BSA with 50 nM free PA, and (4) PA:BSA with 200 nM free PA. These complexes were mixed in ratios ranging from 1:1.5 to 10:1 PA:AA by volume and measured using ADIFAB2 and VQQ. Measurements were done using an SLM 8100 spectrofluorometer (SLM-Aminco) in polystyrene cuvettes. Approximately 15 µL aliquots of each complex mixture was added to 1.5 mL of HEPES buffer, and about 0.5 µM of each probe was used. The ratio was measured for each probe and the total unbound FFA concentration and fractional concentrations of arachidonic and palmitic acids were determined using the following equations.

$$FFA_{AA}\left(\frac{R_{m1AA} - R_1}{Q_{1AA}Kd_{1AA}}\right) = R_1 - R_{01}$$

$$FFA_{AA}\left(\frac{R_{m2AA} - R_2}{Q_{2AA}Kd_{2AA}}\right) + FFA_{AA}\left(\frac{R_{m2PA} - R_2}{Q_{2PA}Kd_{2PA}}\right) = R_2 - R_{02}$$

$$FFA_{AA} + FFA_{PA} = FFA_t$$

where the subscripts 1 and 2 refer to probes VQQ and AD2, respectively, and the constants Q, Kd, and Rm were determined via probe calibration as discussed in example 2. $R_0$ is the ratio in the absence of FFA.

Figure 2:
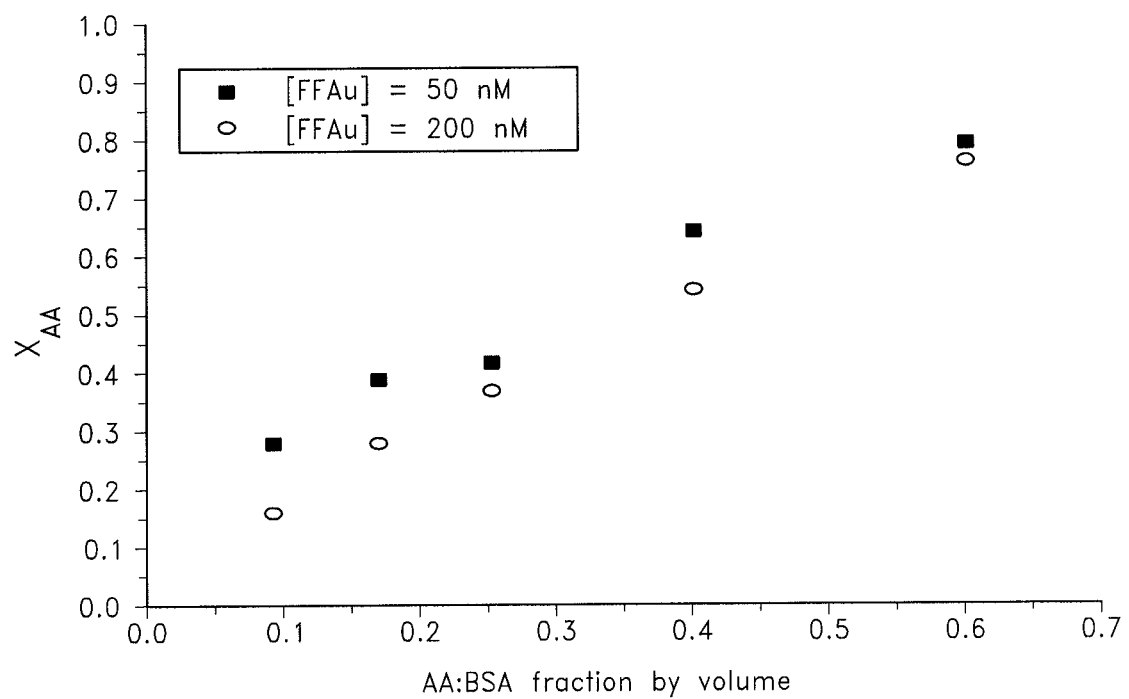
FIG. 2 shows the fraction of total FFAu that is arachidonic acid as a function of the ratio of arachidonic acid to BSA.

The solution to the above equations yields $FFA_{AA}$, $FFA_{PA}$, and $FFA_t$. The fractional concentration of AA and PA are given by $X_{AA} = FFA_{AA}/FFA_t$ and $X_{PA} = FFA_{PA}/FFA_t$. The results from these measurements are displayed in FIG. 2. Complexes with [FFAu]=50 nM and 200 nM are shown. For both cases XAA increases linearly with an increase in the volume fraction of AA:BSA complex relative to the PA:BSA complex.

EXAMPLE 4

Using multiple probes the concentrations of different fatty acid classes in a sample were determined. Specifically, blood plasma and serum samples were measured with three different probes with different fatty acid response profiles, each probe generating its own fluorescence ratio. The three probes were ADIFAB2, Y117A L72A, and D74F L72A (each of these represents a mutant protein labeled with acrylodan). The fluorescence ratio with and without sample was measured for each probe, and the relative concentration of saturated (Xs) and unsaturated (Xu) FFA as well as the total unbound FFA (FFAt) concentration in blood plasma and serum samples were determined by simultaneously solving a set of equations (linear in the fraction of each fatty acid class and total fatty acid concentration) based on the calibration of each probe for different fatty acids. For this analysis, saturated fatty acids include stearic and palmitic acids and unsaturated fatty acids include arachidonic, linolenic, linoleic, and oleic acids.

The set of equations used to determine the FFA concentrations can be expressed in matrix form as shown below.

$$\begin{bmatrix} \frac{R_{ms1} - R_1}{Q_{s1}K_{ds1}} & \frac{R_{mu1} - R_1}{Q_{u1}K_{du1}} & 0 \\ \frac{R_{ms2} - R_2}{Q_{s2}K_{ds2}} & \frac{R_{mu2} - R_2}{Q_{u2}K_{du2}} & 0 \\ \frac{R_{ms3} - R_3}{Q_{s3}K_{ds3}} & \frac{R_{mu3} - R_3}{Q_{u3}K_{du3}} & 0 \\ 1 & 1 & -1 \end{bmatrix} \begin{bmatrix} FFA_s \\ FFA_u \\ FFA_t \end{bmatrix} = \begin{bmatrix} R_1 - R_{01} \\ R_2 - R_{02} \\ R_3 - R_{03} \\ 0 \end{bmatrix}$$

where the subscripts 1, 2, and 3 refer to probes ADIFAB2, Y117A L72A, and D74F L72A, respectively, and the subscripts s, u, and t refer to the saturated, unsaturated, and total fatty acids. The values for the constants Rm, Kd, and Q were determined via probe calibration as discussed in example 2, and $R_0$ is the ratio in the absence of FFA. This matrix was solved to obtain FFAs, FFAu, and FFAt using a least squares method. The fraction of saturated and unsaturated FFA are given by Xs=FFAs/FFAt and Xu=FFAu/FFAt.

Measurements of blood plasma from 12 healthy human donors were conducted with the three probes ADIFAB2, Y117A L72A, and D74F L72A. Measurements were made using a hand-held fluorometer designed for use with these probes (U.S. patent application Ser. No. 10/670,958 which is incorporated herein by reference). Approximately 2 µL of plasma was added to 200 µL of HEPES buffer in a small glass cuvette, and about 1.5 µM of each probe was used, Results (Table 2) indicate that the FFAt (the total unbound concentration) for these individuals determined with the three probes is in excellent agreement with the values reported previously for healthy individuals using ADIFAB2 (Apple et al (2004) Clinical Proteomics, 1:41-44). Furthermore the measured Xs values are consistent with values predicted from albumin binding affinities and the distribution of total FFA for healthy individuals (Richieri and Kleinfeld (1995) J. Lipid Res. 36: 229-240). One skilled in the art can extend this method to determine whether states of disease result in different distributions of unbound free fatty acids.

TABLE 2

Healthy Donors

| ID | Xs | FFAt (nM) |
|---|---|---|
| N01 | 0.18 | 1.9 |
| N02 | 0.16 | 1.3 |
| N03 | 0.22 | 1.4 |
| N04 | 0.31 | 2.7 |
| N05 | 0.24 | 1.4 |
| N06 | 0.13 | 2.2 |
| N07 | 0.36 | 2.2 |
| N08 | 0.22 | 0.8 |
| N09 | 0.23 | 0.7 |
| N10 | 0.20 | 1.0 |
| N11 | 0.16 | 1.2 |
| N12 | 0.20 | 1.0 |
| average | 0.22 | 1.48 |
| stdev | 0.06 | 0.63 |

EXAMPLE 5

Additional probes were produced according to the methods disclosed in Examples 1 and 2. Screening was performed according to Example 2. The results are shown in the attached Tables 3-7. As can be seen from the attached Tables 3-7, it is not necessary to have a mutation at position 72 in order to generate a useful probe. Useful probes are generated by a variety of single and multiple mutations. Generally a value of DR/DR>0.1 indicates a potentially useful probe. Embodiments of the invention are directed to probes with a value of DR/DR>0.1, more preferably, >0.2, yet more preferably, >0.3, yet more preferably, >0.4, yet more preferably, >0.5, yet more preferably, >0.6, yet more preferably, >0.7, yet more preferably, >0.8, yet more preferably, >0.9, yet more preferably, >1.0, yet more preferably, >2.0, yet more preferably, >3.0.

Useful probes are also generated by screening for probes in which the value of DR/DR is <0.1. The clones for these "non-responder" probes may be used to generate non-responder libraries. These non-responder libraries are then screened for their ability to produce probes which bind to metabolites which are not fatty acids. An Example of this type of screen is shown below in Example 6.

TABLE 3

List of responsive clones excluding L72A and WT IFABP

| Clone | AvgOfRo | DR/DR AA | DR/DR LNA | DR/DR LA | DR/DR OA | DR/DR PA |
|---|---|---|---|---|---|---|
| 102A, 72A | 0.24 | 0.45 | 0.44 | 0.35 | 0.52 | 0.20 |
| 102A1, 72A | 0.17 | 0.50 | 0.50 | 0.54 | 0.52 | 0.20 |
| 102C, 72A | 0.24 | 0.14 | 0.12 | 0.12 | 0.11 | 0.09 |
| 102D, 72A | 0.41 | 0.52 | 0.61 | 0.63 | 0.59 | 0.28 |
| 102E, 72A | 0.41 | 0.56 | 0.89 | 0.65 | 0.60 | 0.30 |
| 102F, 72A | 0.25 | 0.95 | 0.53 | 0.73 | 0.64 | 0.43 |
| 102G, 72A | 0.38 | 0.63 | 0.38 | 0.78 | 0.65 | 0.36 |
| 102H, 72A | 0.37 | 0.52 | 0.63 | 0.65 | 0.66 | 0.37 |
| 102H1, 72A | 0.50 | 1.30 | 1.22 | 1.08 | 0.85 | 0.56 |
| 102I, 72A | 0.22 | 1.46 | 1.76 | 1.90 | 1.93 | 1.17 |
| 102K, 72A | 0.39 | 0.47 | 0.51 | 0.55 | 0.48 | 0.23 |
| 102L, 72A | 0.22 | 1.25 | 1.41 | 1.40 | 1.40 | 0.97 |
| 102M1, 72A | 0.16 | 1.12 | 1.15 | 1.17 | 1.21 | 1.01 |
| 102M2, 72A | 0.17 | 0.78 | 0.75 | 0.72 | 0.72 | 0.47 |
| 102M3, 72A | 0.15 | 0.83 | 0.75 | 0.73 | 0.73 | 0.52 |
| 102N, 72A | 0.32 | 0.64 | 0.71 | 0.67 | 0.69 | −1.09 |
| 102P, 72A | 0.34 | 0.50 | 0.56 | 0.54 | 0.49 | 0.39 |
| 102Q, 72A | 0.34 | 0.62 | 0.71 | 0.66 | 0.60 | 0.30 |
| 102R, 72A | 0.33 | 0.51 | 0.57 | 0.60 | 0.56 | 0.25 |
| 102S, 72A | 0.24 | 0.39 | 0.43 | 0.45 | 0.43 | 0.18 |
| 102T, 72A | 0.14 | 0.21 | 0.24 | 0.26 | 0.26 | 0.12 |
| 102V, 72A | 0.18 | 0.46 | 0.51 | 0.67 | 0.57 | 0.35 |
| 102W1, 72A | 0.73 | 0.30 | 0.32 | 0.31 | 0.30 | 0.19 |
| 102W2, 72A | 0.67 | 0.47 | 0.48 | 0.47 | 0.46 | 0.28 |
| 102W3, 72A | 0.70 | 0.44 | 0.45 | 0.45 | 0.40 | 0.25 |
| 102Y, 72A | 0.72 | 0.72 | 0.73 | 0.82 | 0.86 | 0.39 |
| 104D1, 72A | 0.65 | 0.48 | 0.67 | 0.71 | 0.64 | 0.34 |
| 104F1, 72A | 0.35 | 0.66 | 0.42 | 0.47 | 0.45 | 0.27 |
| 104F3, 72A | 0.34 | 0.71 | 0.45 | 0.50 | 0.47 | 0.25 |
| 104G2, 72A | 0.25 | 0.52 | 0.95 | 0.95 | 0.93 | 0.70 |
| 104I1, 72A | 0.16 | 0.28 | 0.30 | 0.30 | 0.31 | 0.23 |
| 104L1, 72A | 0.12 | 0.38 | 0.42 | 0.39 | 0.48 | 0.31 |
| 104M1, 72A | 0.16 | 0.67 | 0.72 | 0.69 | 0.73 | 0.61 |
| 104N1, 72A | 0.40 | 1.14 | 1.06 | 0.67 | 0.71 | 0.52 |
| 104Q1, 72A | 0.43 | 0.24 | 0.15 | 0.13 | 0.14 | 0.14 |
| 104R, 72A | 0.40 | 1.18 | 0.96 | 0.93 | 0.88 | 0.52 |
| 104R1, 72A | 0.47 | 1.14 | 1.13 | 1.22 | 1.20 | 1.00 |
| 104S2, 72A | 0.24 | 1.64 | 1.54 | 1.71 | 1.66 | 1.57 |
| 104T1, 72A | 0.22 | 1.01 | 1.07 | 1.16 | 1.10 | 0.99 |
| 104V1, 72A | 0.16 | 0.63 | 0.73 | 0.73 | 0.76 | 0.63 |
| 104Y1, 72A | 0.88 | 0.36 | 0.28 | 0.26 | 0.24 | 0.14 |
| 106A1, 72A | 0.25 | 0.39 | 0.52 | 0.51 | 0.60 | 0.16 |
| 106C2, 72A | 0.24 | 0.17 | 0.22 | 0.20 | 0.22 | 0.09 |
| 106D3, 72A | 0.30 | 0.66 | 0.77 | 0.80 | 0.64 | 0.26 |
| 106F1, 72A | 0.31 | 0.75 | 0.71 | 0.78 | 0.78 | 0.38 |
| 106G1, 72A | 0.25 | 0.37 | 0.44 | 0.48 | 0.51 | 0.17 |
| 106H2, 72A | 0.31 | 0.75 | 0.73 | 0.78 | 0.82 | 0.33 |
| 106I3, 72A | 0.30 | 0.59 | 0.71 | 0.68 | 0.72 | 0.29 |
| 106L3, 72A | 0.28 | 0.84 | 0.84 | 0.87 | 0.87 | 0.43 |
| 106M1, 72A | 0.26 | 0.68 | 0.62 | 0.62 | 0.65 | 0.28 |
| 106N1, 72A | 0.24 | 0.38 | 0.44 | 0.45 | 0.50 | 0.15 |
| 106Q, 72A | 0.24 | 0.37 | 0.38 | 0.36 | 0.39 | 0.18 |
| 106S2, 72A | 0.26 | 0.32 | 0.40 | 0.36 | 0.48 | 0.15 |
| 106T2, 72A | 0.26 | 0.43 | 0.58 | 0.47 | 0.53 | 0.23 |
| 106V1, 72A | 0.30 | 0.61 | 0.82 | 0.82 | 0.84 | 0.32 |
| 106W, 72A | 0.24 | 1.11 | 1.03 | 1.04 | 0.99 | 0.41 |
| 106Y1, 72A | 0.17 | 0.57 | 0.60 | 0.61 | 0.60 | 0.27 |
| 113M, 72A | 0.18 | 1.33 | 1.38 | 1.46 | 1.42 | 1.19 |
| 115A1, 72A | 0.16 | 1.17 | 1.26 | 1.22 | 1.20 | 1.11 |
| 115D1, 72A | 0.16 | 1.17 | 1.20 | 1.19 | 1.21 | 1.14 |
| 115E1, 72A | 0.22 | 0.12 | 0.10 | 0.15 | 0.10 | 0.08 |
| 115F1, 72A | 0.23 | 1.36 | 1.49 | 1.46 | 1.41 | 0.77 |
| 115G1, 72A | 0.17 | 1.33 | 1.37 | 1.36 | 1.37 | 1.21 |
| 115H1, 72A | 0.15 | 0.89 | 0.70 | 0.74 | 0.68 | 0.51 |
| 115I3, 72A | 0.24 | 0.87 | 0.80 | 0.81 | 0.88 | 0.84 |
| 115K3, 72A | 0.16 | 1.26 | 1.32 | 1.23 | 1.25 | 1.18 |
| 115L3, 72A | 0.17 | 1.26 | 1.29 | 1.24 | 1.25 | 1.15 |
| 115M2, 72A | 0.21 | 1.45 | 1.46 | 1.51 | 1.52 | 1.32 |
| 115N2, 72A | 0.16 | 0.92 | 0.73 | 0.78 | 0.71 | 0.56 |
| 115P1, 72A | 0.27 | −0.17 | 1.35 | 1.37 | 1.26 | 0.70 |
| 115R1, 72A | 0.40 | 1.40 | 1.43 | 1.45 | 1.36 | 0.70 |
| 115S1, 72A | 0.39 | 1.55 | 1.51 | 1.51 | 1.41 | 0.77 |
| 115T3, 72A | 0.21 | 0.57 | 0.54 | 0.45 | 0.46 | 0.49 |
| 115V2, 72A | 0.28 | 0.84 | 0.93 | 0.87 | 0.91 | 0.85 |
| 115W1, 72A | 0.37 | 1.48 | 1.40 | 1.49 | 1.35 | 0.81 |
| 115Y1, 72A | 0.40 | 1.42 | 1.27 | 1.38 | 1.23 | 0.73 |
| 117A, 72A | 0.28 | 1.27 | 0.62 | 1.01 | 0.93 | 0.32 |
| 117C, 72A | 0.25 | −0.17 | −0.13 | −0.19 | −0.24 | −0.12 |

TABLE 3-continued

List of responsive clones excluding L72A and WT IFABP

| Clone | AvgOfRo | DR/DR AA | DR/DR LNA | DR/DR LA | DR/DR OA | DR/DR PA |
|---|---|---|---|---|---|---|
| 117D, 72A | 0.36 | 0.41 | 0.44 | 0.44 | 0.35 | 0.17 |
| 117E, 72A | 0.20 | 0.65 | 0.64 | 0.76 | 0.65 | 0.40 |
| 117F, 72A | 0.19 | 1.33 | 1.38 | 1.36 | 1.37 | 1.20 |
| 117G, 72A | 0.36 | 0.88 | 0.85 | 0.92 | 0.84 | 0.39 |
| 117H, 72A | 0.31 | 0.90 | 0.94 | 1.06 | 1.01 | 0.63 |
| 117I, 72A | 0.14 | 0.68 | 0.68 | 0.80 | 0.67 | 0.41 |
| 117K, 72A | 0.19 | 0.34 | 0.37 | 0.43 | 0.04 | 0.22 |
| 117L, 72A | 0.11 | 0.38 | 0.39 | 0.43 | 0.35 | 0.29 |
| 117M, 72A | 0.18 | 1.27 | 1.36 | 1.31 | 1.32 | 1.14 |
| 117N, 72A | 0.18 | 1.33 | 1.37 | 1.35 | 1.40 | 1.19 |
| 117P, 72A | 0.41 | 0.80 | 0.83 | 0.86 | 0.73 | 0.38 |
| 117Q, 72A | 0.37 | 1.21 | 1.24 | 1.37 | 1.13 | 0.63 |
| 117R, 72A | 0.41 | 0.64 | 0.70 | 0.70 | 0.61 | 0.31 |
| 117S, 72A | 0.36 | 1.35 | 1.07 | 1.42 | 1.19 | 0.55 |
| 117T, 72A | 0.20 | 0.79 | 0.77 | 0.92 | 0.81 | 0.57 |
| 117V, 72A | 0.16 | 0.82 | 0.81 | 0.94 | 0.81 | 0.49 |
| 117W, 72A | 0.29 | 0.55 | 0.46 | 0.45 | 0.39 | 0.34 |
| 117Y, 72A | 0.18 | 1.35 | 1.40 | 1.44 | 1.36 | 1.14 |
| 119A, 72A | 0.31 | 0.70 | 0.65 | 0.61 | 0.63 | 0.30 |
| 119C, 72A | 0.68 | 1.06 | 1.00 | 1.02 | 0.97 | 0.35 |
| 119F, 72A | 0.20 | 0.93 | 0.93 | 0.90 | 0.94 | 0.69 |
| 119G, 72A | 0.25 | 0.83 | 0.81 | 0.77 | 0.78 | 0.46 |
| 119H, 72A | 0.33 | 0.71 | 0.67 | 0.63 | 0.59 | 0.32 |
| 119I, 72A | 0.33 | 1.01 | 1.06 | 1.10 | 1.08 | 0.69 |
| 119K, 72A | 0.31 | 0.78 | 0.78 | 0.85 | 0.87 | 0.58 |
| 119Q, 72A | 0.52 | 0.60 | 0.62 | 0.58 | 0.60 | 0.35 |
| 119S, 72A | 0.31 | 0.78 | 0.73 | 0.46 | 0.71 | 0.37 |
| 119T, 72A | 0.25 | 1.22 | 1.21 | 1.22 | 1.26 | 0.79 |
| 119V, 72A | 0.33 | 0.99 | 1.00 | 1.01 | 1.02 | 0.57 |
| 11A1, L72A | 0.20 | 0.60 | 0.67 | 0.73 | 0.64 | 0.56 |
| 11C, 72A | 0.45 | 0.52 | 0.64 | 0.70 | 0.70 | 0.80 |
| 11C2, L72A | 0.49 | 0.51 | 0.67 | 0.67 | 0.66 | 0.55 |
| 11D1, L72A | 0.21 | 0.82 | 0.86 | 0.91 | 0.92 | 0.83 |
| 11E2, L72A | 0.24 | 0.54 | 0.52 | 0.62 | 0.55 | 0.54 |
| 11F1, L72A | 0.32 | 0.42 | 0.29 | 0.28 | 0.20 | 0.18 |
| 11G, 72A | 0.14 | 0.63 | 0.67 | 0.70 | 0.62 | 0.61 |
| 11G1, 72A | 0.17 | 0.81 | 0.81 | 0.92 | 0.85 | 0.78 |
| 11G1, L72A | 0.14 | 0.55 | 0.59 | 0.70 | 0.60 | 0.53 |
| 11H1, 72A | 0.21 | 0.58 | 0.59 | 0.55 | 0.48 | 0.56 |
| 11H1, L72A | 0.18 | 0.48 | 0.50 | 0.47 | 0.39 | 0.48 |
| 11I1, L72A | 0.38 | 0.58 | 0.51 | 0.55 | 0.39 | 1.19 |
| 11L1, L72A | 0.39 | 0.47 | 0.35 | 0.30 | 0.15 | 0.27 |
| 11M2, 72A | 0.33 | 0.65 | 0.59 | 0.55 | 0.42 | 0.57 |
| 11M2, L72A | 0.32 | 0.70 | 0.65 | 0.58 | 0.46 | 0.54 |
| 11Q1, 72A | 0.26 | 1.53 | 1.58 | 1.72 | 1.72 | 1.45 |
| 11Q1, L72A | 0.21 | 1.33 | 1.43 | 1.37 | 1.32 | 1.19 |
| 11S5, 72A | 0.15 | 0.41 | 0.39 | 0.44 | 0.37 | 0.47 |
| 11S5, L72A | 0.12 | 0.33 | 0.37 | 0.36 | 0.29 | 0.35 |
| 11T1, 72A | 0.18 | 0.51 | 0.47 | 0.51 | 0.41 | 1.95 |
| 11T1, L72A | 0.17 | 0.49 | 0.47 | 0.45 | 0.35 | 0.35 |
| 11V2, 72A | 0.36 | 0.93 | 0.76 | 0.83 | 0.55 | 0.73 |
| 11W1, 72A | 0.26 | 0.43 | 0.36 | 0.34 | 0.23 | 0.20 |
| 11W1, L72A | 0.29 | 0.43 | 0.39 | 0.40 | 0.22 | 0.15 |
| 11Y1, 72A | 0.31 | 0.52 | 0.31 | 0.33 | 0.16 | 0.30 |
| 11Y1, L72A | 0.33 | 0.49 | 0.33 | 0.32 | 0.16 | 0.25 |
| 126A, 72A | 0.19 | 1.27 | 1.36 | 1.32 | 1.38 | 1.22 |
| 126D, 72A | 0.38 | 0.44 | 0.56 | 0.59 | 0.64 | 0.37 |
| 126E, 72A | 0.33 | 0.25 | 0.32 | 0.34 | 0.30 | 0.21 |
| 126F, 72A | 0.38 | 0.52 | 0.53 | 0.51 | 0.43 | 0.34 |
| 126H, 72A | 0.31 | 0.20 | 0.46 | 0.46 | 0.43 | 0.32 |
| 126I, 72A | 0.30 | 0.45 | 0.43 | 0.43 | 0.34 | 0.38 |
| 126L, 72A | 0.34 | 0.66 | 0.66 | 0.64 | 0.55 | 0.38 |
| 126M, 72A | 0.32 | 0.32 | 0.28 | 0.31 | 0.24 | 0.29 |
| 126V, 72A | 0.28 | 0.42 | 0.42 | 0.45 | 0.33 | 0.34 |
| 14A, 72A | 0.44 | 0.53 | 0.56 | 0.56 | 0.36 | 0.24 |
| 14D, 72A | 0.44 | 0.46 | 0.51 | 0.53 | 0.34 | 0.28 |
| 14E, 72A | 0.41 | 0.51 | 0.61 | 0.56 | 0.41 | 0.44 |
| 14F, 72A | 0.22 | 0.83 | 0.88 | 0.88 | 0.72 | 0.60 |
| 14G, 72A | 0.44 | 0.43 | 0.46 | 0.42 | 0.24 | 0.19 |
| 14H, 72A | 0.35 | 0.37 | 0.42 | 0.45 | 0.25 | 0.17 |
| 14I, 72A | 0.39 | 0.57 | 0.90 | 0.79 | 0.57 | 0.59 |
| 14K, 72A | 0.36 | 1.08 | 0.92 | 1.06 | 0.84 | 0.47 |
| 14L, 72A | 0.31 | 0.89 | 0.93 | 0.87 | 0.44 | 3.07 |
| 14M, 72A | 0.33 | 0.62 | 0.68 | 0.68 | 0.41 | 0.45 |
| 14N, 72A | 0.45 | 0.42 | 0.53 | 0.49 | 0.35 | 0.32 |
| 14P, 72A | 0.46 | 0.55 | 0.64 | 0.64 | 0.58 | 0.30 |
| 14Q, 72A | 0.40 | 0.50 | 0.52 | 0.48 | 0.29 | 0.33 |
| 14R, 72A | 0.41 | 0.49 | 0.51 | 0.56 | 0.26 | 0.26 |
| 14S, 72A | 0.46 | 0.46 | 0.53 | 0.53 | 0.33 | 0.27 |
| 14T, 72A | 0.46 | 0.64 | 1.15 | 0.76 | 0.56 | 0.36 |
| 14V, 72A | 0.32 | 0.76 | 0.87 | 0.84 | 0.51 | 0.43 |
| 14W, 72A | 0.11 | 0.30 | 0.31 | 0.33 | 0.26 | 0.23 |
| 14Y, 72A | 0.17 | 1.29 | 1.29 | 1.23 | 2.22 | 1.07 |
| wt 17A, 72A | 0.28 | 0.53 | 0.97 | 0.56 | 0.38 | 0.24 |
| 17C, 72A | 0.36 | 0.15 | 0.26 | 0.25 | 0.31 | 0.10 |
| 17D, 72A | 0.40 | 0.28 | 0.34 | 0.31 | 0.26 | 0.16 |
| 17E, 72A | 0.27 | 0.80 | 0.88 | 0.90 | 0.84 | 0.53 |
| 17F, 72A | 0.19 | 1.37 | 1.38 | 1.35 | 1.42 | 1.14 |
| 17G, 72A | 0.39 | 0.48 | 0.62 | 0.58 | 0.52 | 0.28 |
| 17H, 72A | 0.36 | 0.52 | 0.50 | 0.48 | 0.40 | 0.22 |
| 17I, 72A | 0.26 | 0.64 | 0.54 | 0.50 | 0.62 | 0.28 |
| 17K, 72A | 0.41 | 0.28 | 0.29 | 0.33 | 0.31 | 0.13 |
| 17L, 72A | 0.25 | 0.52 | 0.45 | 0.42 | 0.46 | 0.28 |
| 17M, 72A | 0.30 | 0.59 | 0.53 | 0.49 | 0.49 | 0.28 |
| 17N, 72A | 0.34 | 0.47 | 0.51 | 0.50 | 0.49 | 0.22 |
| 17P, 72A | 0.45 | 0.51 | 0.63 | 0.60 | 0.55 | 0.24 |
| 17Q, 72A | 0.25 | 0.62 | 0.59 | 0.59 | 0.55 | 0.29 |
| 17R, 72A | 0.36 | 0.43 | 0.48 | 0.52 | 0.45 | 0.22 |
| 17S, 72A | 0.35 | 0.50 | 0.61 | 0.56 | 0.47 | 0.25 |
| 17T, 72A | 0.32 | 0.50 | 0.51 | 0.51 | 0.49 | 0.25 |
| 17V, 72A | 0.30 | 0.64 | 0.59 | 0.55 | 0.56 | 0.31 |
| 17W, 72A | 0.18 | 1.42 | 1.61 | 1.42 | 1.24 | 1.07 |
| 17Y, 72A | 0.65 | 0.73 | 0.81 | 0.71 | 0.73 | 0.50 |
| 18Q, 72A | 0.22 | 0.09 | 0.13 | 0.11 | 0.08 | 0.09 |
| 21W, 72A | 0.60 | 3.70 | 2.40 | 2.43 | 3.02 | 1.45 |
| 23F2, 72A | 0.22 | 0.22 | 0.17 | 0.19 | 0.20 | 0.12 |
| 23H1, 72A | 0.20 | 0.16 | 0.17 | 0.13 | 0.11 | 0.13 |
| 23K1, 72A | 0.45 | 0.13 | 0.13 | 0.14 | 0.13 | 0.08 |
| 23L3, 72A | 0.23 | 1.17 | 1.03 | 1.04 | 1.06 | 0.93 |
| 23N1, 72A | 0.22 | 0.12 | 0.13 | 0.13 | 0.12 | 0.10 |
| 23P1, 72A | 0.32 | 1.25 | 1.38 | 1.36 | 1.24 | 0.64 |
| 23R3, 72A | 0.20 | 0.14 | 0.14 | 0.14 | 0.12 | 0.10 |
| 23T1, 72A | 0.16 | 0.22 | 0.21 | 0.33 | 0.19 | 0.24 |
| 23V2, 72A | 0.17 | 1.46 | 1.35 | 1.73 | 1.56 | 1.48 |
| 23W1, 72A | 0.45 | 0.62 | 0.96 | 0.79 | 0.45 | 0.49 |
| 23Y1, 72A | 0.26 | 0.49 | 0.44 | 0.44 | 0.41 | 0.28 |
| 31C1, 72A | 0.30 | 0.32 | 0.36 | 0.36 | 0.30 | 0.23 |
| 31D2, 72A | 0.31 | 0.20 | 0.14 | 0.16 | 0.13 | 0.06 |
| 31E3, 72A | 0.35 | 0.55 | 0.82 | 0.74 | 0.50 | 0.38 |
| 31F2, 72A | 0.43 | 1.41 | 1.62 | 1.76 | 1.43 | 1.21 |
| 31I1, 72A | 0.68 | 0.30 | 0.41 | 0.17 | −0.21 | 0.09 |
| 31K2, 72A | 0.26 | 0.85 | 0.90 | 0.91 | 0.97 | 0.42 |
| 31M2, 72A | 0.81 | 0.52 | 0.57 | 0.41 | 1.08 | 0.46 |
| 31N2, 72A | 0.36 | 0.88 | 1.06 | 1.04 | 0.91 | 0.50 |
| 31P1, 72A | 0.27 | 0.25 | 0.27 | 0.30 | 0.22 | 0.23 |
| 31Q3, 72A | 0.38 | 1.02 | 1.49 | 1.47 | 1.31 | 1.04 |
| 31R1, 72A | 0.18 | 0.25 | 0.44 | 0.40 | 0.23 | 0.34 |
| 31T2, 72A | 0.37 | 0.65 | 0.91 | 0.75 | 0.53 | 0.41 |
| 31V2, 72A | 0.61 | 0.40 | 0.78 | 0.38 | 0.08 | 0.21 |
| 31W2, 72A | 0.46 | 0.99 | 1.03 | 1.15 | 0.87 | 0.62 |
| 31Y1, 72A | 0.48 | 1.78 | 1.61 | 1.75 | 1.55 | 1.10 |
| 31Y2, 72A | 0.69 | 0.37 | 0.80 | 0.36 | 0.01 | 0.17 |
| 34A, 72A | 0.35 | 0.58 | 0.57 | 0.57 | 0.49 | 0.33 |
| 34C, 72A | 0.44 | 0.34 | 0.33 | 0.59 | 0.30 | 0.18 |
| 34E, 72A | 0.32 | 0.62 | 0.57 | 0.60 | 0.49 | 0.48 |
| 34G, 72A | 0.51 | 0.54 | 0.29 | 0.33 | 0.13 | 0.18 |
| 34H, 72A | 0.37 | 0.65 | 0.72 | 0.74 | 0.52 | 0.38 |
| 34K, 72A | 0.48 | 0.43 | 1.33 | 0.61 | 0.41 | 0.26 |
| 34N, 72A | 0.16 | 1.19 | 1.18 | 1.16 | 1.16 | 1.11 |
| 34P, 72A | 0.42 | 0.46 | 0.76 | 0.66 | 0.46 | 0.35 |
| 34Q, 72A | 0.37 | 0.52 | 0.48 | 0.56 | 0.44 | 0.36 |
| 34R, 72A | 0.52 | 0.41 | 0.47 | 0.61 | 0.44 | 0.30 |
| 34S, 72A | 0.36 | 0.58 | 0.59 | 0.65 | 0.58 | 0.43 |
| 34T, 72A | 0.34 | 0.61 | 0.67 | 0.64 | 0.53 | 0.40 |

TABLE 3-continued

List of responsive clones excluding L72A and WT IFABP

| Clone | AvgOfRo | DR/DR AA | DR/DR LNA | DR/DR LA | DR/DR OA | DR/DR PA |
|---|---|---|---|---|---|---|
| 34V, 72A | 0.17 | 1.22 | 1.21 | 1.15 | 1.19 | 1.11 |
| 34W, 72A | 0.24 | 1.31 | 1.37 | 1.34 | 1.38 | 0.93 |
| 34Y, 72A | 0.18 | 1.22 | 1.22 | 1.24 | 1.19 | 1.06 |
| 36A, 72A | 0.27 | 0.53 | 0.50 | 0.51 | 0.46 | 0.46 |
| 36C3, 72A | 0.38 | −0.22 | −0.30 | −0.36 | −0.40 | −0.21 |
| 36D1, 72A | 0.42 | 0.20 | 0.21 | 0.27 | 0.20 | 0.18 |
| 36E2, 72A | 0.31 | 0.24 | 0.23 | 0.25 | 0.20 | 0.19 |
| 36F1, 72A | 0.25 | 0.66 | 0.66 | 0.67 | 0.55 | 0.52 |
| 36G2, 72A | 0.36 | 1.00 | 1.16 | 1.17 | 0.97 | 0.55 |
| 36H1, 72A | 0.34 | 0.76 | 0.86 | 0.81 | 0.77 | 0.40 |
| 36I1, 72A | 0.29 | 1.01 | 1.13 | 1.11 | 0.95 | 0.80 |
| 36K, 72A | 0.43 | 0.38 | 0.42 | 0.38 | 0.41 | 0.16 |
| 36L, 72A wt | 0.16 | 1.25 | 1.00 | 1.21 | 1.25 | 1.13 |
| 36M, 72A | 0.20 | 1.23 | 1.08 | 1.10 | 1.12 | 0.97 |
| 36N, 72A | 0.35 | 0.47 | 0.42 | 0.47 | 0.38 | 0.39 |
| 36P, 72A | 0.44 | 0.32 | 0.36 | −7.45 | 0.14 | 0.31 |
| 36Q, 72A | 0.30 | 1.20 | 1.28 | 1.26 | 1.12 | 0.81 |
| 36R, 72A | 0.30 | 1.04 | 1.17 | 1.17 | 1.14 | 0.70 |
| 36S, 72A | 0.31 | 0.49 | 0.50 | 0.50 | 0.43 | 0.42 |
| 36Y, 72A | 0.24 | 0.68 | 0.68 | 0.75 | 0.66 | 0.60 |
| 38A2, 72A | 0.32 | 1.23 | 1.30 | 1.31 | 1.26 | 0.68 |
| 38E1, 72A | 0.24 | 0.57 | 0.29 | 0.59 | 0.54 | 0.31 |
| 38F1, 72A | 0.19 | 0.91 | 0.96 | 0.95 | 0.97 | 0.85 |
| 38G1, 72A | 0.34 | 1.03 | 1.07 | 1.10 | 1.03 | 0.56 |
| 38H1, 72A | 0.27 | 1.24 | 1.19 | 1.25 | 1.16 | 0.74 |
| 38I3, 72A | 0.19 | 1.18 | 1.21 | 1.22 | 1.21 | 1.12 |
| 38K1, 72A | 0.26 | 0.83 | 0.86 | 0.90 | 0.76 | 0.48 |
| 38N1, 72A | 0.50 | 1.08 | 1.14 | 1.12 | 0.97 | 0.65 |
| 38Q1, 72A | 0.26 | 1.87 | 1.87 | 1.90 | 1.75 | 1.30 |
| 38S1, 72A | 0.32 | 1.28 | 1.37 | 1.37 | 1.28 | 0.71 |
| 38T3, 72A | 0.30 | 1.60 | 1.64 | 1.58 | 1.55 | 1.02 |
| 38V2, 72A | 0.21 | 1.65 | 1.67 | 1.70 | 1.75 | 1.50 |
| 38W1, 72A | 0.23 | 1.35 | 1.34 | 2.41 | 1.58 | 1.55 |
| 38Y1, 72A | 0.21 | 2.08 | 1.88 | 1.82 | 1.72 | 1.52 |
| 40F2, L72A | 0.20 | 0.89 | 0.99 | 0.90 | 0.90 | 0.80 |
| 40M1, L72A | 0.20 | 0.99 | 1.02 | 1.09 | 0.99 | 0.69 |
| 40V1, L72A | 0.21 | 1.20 | 1.28 | 1.24 | 1.21 | 0.91 |
| 40Y3, L72A | 0.22 | 0.89 | 0.49 | 0.50 | 0.48 | 0.29 |
| 47A1, L72A | 0.29 | 0.54 | 0.57 | 0.58 | 0.59 | 0.30 |
| 47C3, L72A | 0.24 | 0.32 | 0.35 | 0.37 | 0.35 | 0.23 |
| 47E3, L72A | 0.18 | 1.25 | 1.26 | 1.23 | 1.25 | 1.06 |
| 47G1, L72A | 0.34 | 0.51 | 0.63 | 0.66 | 0.59 | 0.32 |
| 47H1, L72A | 0.22 | 0.63 | 0.70 | 0.74 | 0.67 | 0.43 |
| 47I2, L72A | 0.19 | 1.19 | 1.19 | 1.22 | 1.15 | 0.92 |
| 47L2, L72A | 0.22 | 1.15 | 1.20 | 1.21 | 1.20 | 0.90 |
| 47M, 72A | 0.23 | 1.14 | 1.13 | 1.18 | 1.17 | 0.97 |
| 47M2, L72A | 0.18 | 1.00 | 0.97 | 0.99 | 0.95 | 0.83 |
| 47P1, L72A | 0.36 | 0.54 | 0.61 | 0.59 | 0.57 | 0.26 |
| 47Q3, L72A | 0.16 | 0.72 | 0.73 | 0.78 | 0.75 | 0.46 |
| 47R3, L72A | 0.33 | 0.56 | 0.61 | 0.64 | 0.62 | 0.30 |
| 47S1, L72A | 0.31 | 0.61 | 0.69 | 0.66 | 0.64 | 0.34 |
| 47T1, L72A | 0.24 | 0.68 | 0.74 | 0.77 | 0.74 | 0.46 |
| 47V3, L72A | 0.19 | 1.00 | 1.01 | 1.04 | 1.01 | 0.78 |
| 47W1, L72A | 0.17 | 1.18 | 1.14 | 1.18 | 1.22 | 1.07 |
| 47Y2, L72A | 0.19 | 1.37 | 1.40 | 1.40 | 1.42 | 1.17 |
| 49A1, 72A | 0.45 | 1.72 | 1.68 | 1.72 | 1.60 | 0.79 |
| 49C1, 72A | 0.29 | −0.13 | −0.18 | −0.21 | −0.20 | −0.18 |
| 49D1, 72A | 0.23 | 0.31 | 0.30 | 0.32 | 0.32 | 0.16 |
| 49F1, 72A | 0.39 | 1.18 | 1.18 | 1.14 | 1.14 | 0.75 |
| 49G1, 72A | 0.43 | 1.26 | 1.25 | 1.29 | 1.15 | 0.64 |
| 49H1, 72A | 0.44 | 1.47 | 1.54 | 1.58 | 1.39 | 0.75 |
| 49I1, 72A | 0.36 | 1.80 | 1.82 | 1.84 | 1.80 | 1.16 |
| 49K1, 72A | 0.43 | 1.64 | 1.68 | 1.71 | 1.51 | 0.80 |
| 49L1, 72A | 0.37 | 1.76 | 1.77 | 1.81 | 1.67 | 1.00 |
| 49M1, 72A | 0.35 | 1.36 | 1.37 | 1.37 | 1.30 | 0.94 |
| 49N1, 72A | 0.35 | 1.26 | 1.18 | 1.10 | 1.11 | 0.74 |
| 49P1, 72A | 0.40 | 1.57 | 1.53 | 1.59 | 1.40 | 0.76 |
| 49Q, 72A | 0.23 | 0.62 | 0.55 | 0.58 | 0.56 | 0.43 |
| 49Q1, 72A | 0.39 | 0.92 | 1.23 | 1.25 | 1.20 | 0.69 |
| 49R1, 72A | 0.42 | 1.68 | 1.70 | 1.75 | 1.56 | 0.78 |
| 49S1, 72A | 0.40 | 1.27 | 1.34 | 1.29 | 1.18 | 0.66 |
| 49T1, 72A | 0.28 | 0.66 | 0.64 | 0.67 | 0.67 | 0.43 |
| 49W1, 72A | 0.31 | 0.58 | 0.58 | 0.58 | 0.56 | 0.35 |
| 49Y1, 72A | 0.43 | 1.39 | 1.44 | 1.51 | 1.34 | 0.70 |
| 51A1, 72A | 0.41 | 1.38 | 1.49 | 1.48 | 1.28 | 0.70 |
| 51C3, 72A | 0.42 | 1.44 | 1.47 | 1.55 | 1.35 | 0.69 |
| 51D1, 72A | 0.42 | 1.34 | 1.39 | 1.38 | 1.28 | 0.68 |
| 51F1, 72A | 0.43 | 1.64 | 1.60 | 1.70 | 1.47 | 0.76 |
| 51G1, 72A | 0.41 | 1.64 | 1.76 | 1.71 | 1.57 | 0.78 |
| 51H1, 72A | 0.35 | 1.52 | 1.58 | 1.64 | 0.58 | 0.81 |
| 51I1, 72A | 0.39 | 1.50 | 1.62 | 1.55 | 1.41 | 0.72 |
| 51K1, 72A | 0.37 | 1.00 | 1.02 | −0.01 | 1.01 | 0.56 |
| 51L3, 72A | 0.39 | 1.64 | 1.66 | 1.65 | 1.45 | 0.76 |
| 51N1, 72A | 0.38 | 1.38 | 1.39 | 1.46 | 1.26 | 0.73 |
| 51P3, 72A | 0.38 | 1.42 | 1.48 | 1.42 | 1.21 | 0.72 |
| 51Q1, 72A | 0.40 | 1.56 | 1.65 | 1.63 | 1.43 | 0.73 |
| 51R1, 72A | 0.40 | 1.50 | 1.56 | 1.56 | 1.35 | 0.73 |
| 51S1, 72A | 0.38 | 1.64 | 1.66 | 1.78 | 1.61 | 0.80 |
| 51T3, 72A | 0.40 | 1.60 | 1.60 | 1.65 | 1.44 | 0.71 |
| 51V3, 72A | 0.40 | 1.52 | 1.53 | 1.64 | 1.43 | 0.73 |
| 51W2, 72A | 0.39 | 1.69 | 1.70 | 1.77 | 1.55 | 0.80 |
| 51Y1, 72A | 0.38 | 1.38 | 1.44 | 1.50 | 1.38 | 0.72 |
| 55A1, 72A | 0.18 | 0.33 | 0.36 | 0.34 | 0.30 | 0.28 |
| 55D1, 72A | 0.18 | 0.11 | 0.12 | 0.12 | 0.10 | 0.10 |
| 55E, 72A | 0.25 | 0.21 | 0.21 | 0.21 | 0.21 | 0.17 |
| 55G1, 72A | 0.20 | 0.19 | 0.23 | 0.22 | 0.19 | 0.18 |
| 55H2, 72A | 0.18 | 0.36 | 0.32 | 0.38 | 0.27 | 0.26 |
| 55I1, 72A | 0.18 | 1.08 | 0.89 | 0.83 | 0.90 | 0.77 |
| 55K1, 72A | 0.30 | 0.32 | 0.35 | 0.34 | 0.30 | 0.27 |
| 55L1, 72A | 0.16 | 0.86 | 0.72 | 0.71 | 0.82 | 0.63 |
| 55M1, 72A | 0.36 | 1.40 | 1.42 | 0.97 | 1.41 | 0.84 |
| 55N1, 72A | 0.20 | 0.34 | 0.30 | 0.29 | 0.27 | 0.22 |
| 55P1, 72A | 0.33 | 1.01 | 0.96 | 1.05 | 0.93 | 0.54 |
| 55Q1, 72A | 0.23 | 0.60 | 0.49 | 0.47 | 0.54 | 0.43 |
| 55R1, 72A | 0.24 | 0.40 | 0.37 | 0.41 | 0.39 | 0.30 |
| 55S1, 72A | 0.20 | 0.48 | 0.43 | 0.42 | 0.41 | 0.41 |
| 55T1, 72A | 0.17 | 1.26 | 1.27 | 1.25 | 1.28 | 1.12 |
| 55W2, 72A | 0.23 | 0.77 | 0.82 | 0.79 | 0.70 | 0.63 |
| 55Y3, 72A | 0.12 | 0.47 | 0.34 | 0.32 | 0.33 | 0.25 |
| 60A, 72A | 0.23 | 0.79 | 0.94 | 0.98 | 0.94 | 0.74 |
| 60C, 72A | 0.17 | 1.30 | 1.36 | 1.33 | 1.34 | 1.04 |
| 60F, 72A | 0.25 | 1.79 | 1.76 | 1.68 | 1.90 | 1.53 |
| 60G, 72A | 0.23 | 0.29 | 0.24 | 0.25 | 0.24 | 0.19 |
| 60H, 72A | 0.29 | 0.17 | 0.18 | 0.17 | 0.17 | 0.12 |
| 60I, 72A | 0.20 | 1.54 | 1.63 | 1.73 | 1.72 | 1.52 |
| 60K, 72A | 0.41 | 0.46 | 0.57 | 0.62 | 0.60 | 0.35 |
| 60L, 72A | 0.24 | 1.08 | 1.26 | 1.29 | 1.27 | 1.10 |
| 60M, 72A | 0.29 | 0.77 | 0.93 | 1.01 | 0.91 | 0.76 |
| 60N, 72A | 0.21 | 1.24 | 1.59 | 1.57 | 1.54 | 1.30 |
| 60P, 72A | 0.40 | 0.62 | 0.77 | 0.81 | 0.81 | 0.37 |
| 60Q, 72A | 0.27 | 0.36 | 0.42 | 0.41 | 0.41 | 0.35 |
| 60R, 72A | 0.27 | 0.14 | 0.14 | 0.12 | 0.13 | 0.08 |
| 60S, 72A | 0.26 | 0.56 | 0.71 | 0.72 | 0.67 | 0.59 |
| 60T, 72A | 0.22 | 1.72 | 1.73 | 1.73 | 1.76 | 1.49 |
| 60W, 72A | 0.18 | 0.67 | 0.74 | 0.84 | 0.76 | 0.59 |
| 62A, 72A | 0.27 | 1.07 | 1.08 | 0.96 | 0.86 | 0.57 |
| 62C, 72A | 0.19 | 1.30 | 1.31 | 1.31 | 1.29 | 1.18 |
| 62D, 72A | 0.23 | 1.49 | 1.58 | 1.60 | 1.57 | 1.39 |
| 62E, 72A | 0.21 | 1.48 | 1.52 | 1.49 | 1.52 | 1.40 |
| 62G, 72A | 0.22 | 1.43 | 1.44 | 1.44 | 1.46 | 1.26 |
| 62H, 72A | 0.20 | 1.42 | 1.44 | 1.40 | 1.40 | 1.24 |
| 62I, 72A | 0.19 | 1.40 | 1.38 | 1.36 | 1.37 | 1.27 |
| 62N, 72A | 0.20 | 1.40 | 1.40 | 1.34 | 1.37 | 1.29 |
| 62T, 72A | 0.24 | 0.99 | 0.96 | 1.02 | 1.00 | 0.65 |
| 68A, 72A | 0.23 | 0.23 | 0.19 | 0.18 | 0.19 | 0.13 |
| 68C, 72A | 0.58 | 0.18 | 0.25 | 0.12 | 0.29 | 0.13 |
| 68D, 72A | 0.38 | 1.24 | 1.23 | 1.23 | 1.13 | 0.52 |
| 68E, 72A | 0.36 | 0.89 | 0.92 | 0.96 | 0.91 | 0.53 |
| 68G, 72A | 0.23 | 0.24 | 0.18 | 0.17 | 0.21 | 0.12 |
| 68I, 72A | 0.22 | 0.42 | 0.36 | 0.37 | 0.39 | 0.35 |
| 68L, 72A | 0.21 | 0.66 | 0.52 | 0.53 | 0.55 | 0.52 |
| 68M, 72A | 0.19 | 0.52 | 0.35 | 0.34 | 0.35 | 0.33 |
| 68N, 72A | 0.33 | 0.67 | 0.60 | 0.67 | 0.63 | 0.35 |

TABLE 3-continued

List of responsive clones excluding L72A and WT IFABP

| Clone | AvgOfRo | DR/DR AA | DR/DR LNA | DR/DR LA | DR/DR OA | DR/DR PA |
|---|---|---|---|---|---|---|
| 68Q, 72A | 0.30 | 0.47 | 0.38 | 0.43 | 0.45 | 0.28 |
| 68S, 72A | 0.21 | 0.20 | 0.14 | 0.14 | 0.14 | 0.10 |
| 68T, 72A | 0.18 | 0.18 | 0.12 | 0.11 | 0.13 | 0.10 |
| 68V, 72A | 0.20 | 0.29 | 0.22 | 0.23 | 0.25 | 0.19 |
| 68Y, 72A | 0.17 | 0.42 | 0.41 | 0.36 | 0.46 | 0.35 |
| 70C, 72A | 0.43 | 0.23 | 0.24 | 0.27 | 0.24 | 0.14 |
| 70M, 72A | 0.27 | 0.34 | 0.53 | 0.39 | 0.42 | 0.26 |
| 72C | 0.30 | 0.14 | 0.17 | 0.25 | 0.20 | 0.12 |
| 72D | 0.47 | 0.27 | 0.41 | 0.37 | 0.28 | 0.24 |
| 72E | 0.57 | 0.27 | 0.36 | 0.38 | 0.34 | 0.19 |
| 72F | 0.52 | 0.40 | 0.59 | 0.61 | 0.57 | 0.46 |
| 72G | 0.28 | 0.62 | 0.48 | 0.48 | 0.52 | 0.26 |
| 72K | 0.40 | 0.26 | 0.31 | 0.26 | 0.19 | 0.13 |
| 72M | 0.38 | 1.31 | 1.35 | 1.46 | 1.49 | 1.32 |
| 72N | 0.31 | 0.65 | 0.70 | 0.77 | 0.83 | 0.44 |
| 72Q | 0.66 | 0.77 | 0.73 | 0.76 | 0.78 | 0.99 |
| 72R | 0.69 | 0.45 | 0.49 | 0.51 | 0.45 | 0.26 |
| 72S | 0.21 | 0.65 | 0.71 | 0.73 | 0.62 | 0.68 |
| 72V | 0.09 | 0.18 | 0.15 | 0.21 | 0.20 | 0.16 |
| 72Y | 0.39 | 0.35 | 0.59 | 0.64 | 0.56 | 0.41 |
| 73E, 72A | 0.23 | 0.15 | 0.14 | 0.19 | 0.14 | 0.13 |
| 73F, 72A | 0.33 | 1.21 | 1.86 | 1.23 | 0.73 | 1.13 |
| 73G, 72A | 0.22 | 0.46 | 0.53 | 0.56 | 0.52 | 0.41 |
| 73H, 72A | 0.11 | 0.15 | 0.25 | 0.18 | 0.13 | 0.16 |
| 73K, 72A | 0.24 | 0.30 | 0.28 | 0.29 | 0.28 | 0.15 |
| 73L, 72A | 0.29 | 0.73 | 0.34 | 0.33 | 0.38 | 0.25 |
| 73N, 72A | 0.21 | 0.48 | 0.47 | 0.43 | 0.41 | 0.39 |
| 73P, 72A | 0.15 | 0.42 | 0.41 | 0.30 | 0.30 | 0.26 |
| 73Q, 72A | 0.27 | 1.36 | 1.31 | 1.39 | 1.28 | 1.19 |
| 73R, 72A | 0.27 | 0.40 | 0.33 | 0.36 | 0.27 | 0.20 |
| 73S, 72A | 0.20 | 1.01 | 1.08 | 1.05 | 0.96 | 0.99 |
| 73T, 72A | 0.16 | 0.87 | 0.77 | 0.77 | 0.78 | 0.62 |
| 73V, 72A | 0.30 | 0.98 | 0.50 | 0.40 | 0.60 | 0.48 |
| 73W, 72A | 0.39 | 1.77 | 1.93 | 1.89 | 1.66 | 1.05 |
| 74A, 72A | 0.20 | 1.42 | 1.42 | 1.34 | 1.34 | 1.27 |
| 74C, 72A | 0.45 | 0.83 | 0.74 | 0.71 | 0.56 | 0.29 |
| 74F, 72A | 0.25 | 1.02 | 1.36 | 1.19 | 1.10 | 1.23 |
| 74L, 72A | 0.17 | 0.22 | 0.40 | 0.30 | 0.19 | 0.36 |
| 74N, 72A | 0.16 | 1.62 | 1.57 | 1.44 | 1.52 | 1.38 |
| 74Q, 72A | 0.29 | 0.81 | 0.86 | 0.87 | 0.74 | 0.43 |
| 74T, 72A | 0.27 | 0.76 | 0.78 | 0.82 | 0.70 | 0.37 |
| 78A3, 72A | 0.25 | 0.48 | 0.50 | 0.44 | 0.41 | 0.25 |
| 78C2, 72A | 0.35 | 0.15 | 0.20 | 0.20 | 0.19 | 0.09 |
| 78F1, 72A | 0.35 | 2.04 | 2.05 | 2.00 | 1.83 | 0.91 |
| 78H1, 72A | 0.39 | 1.23 | 1.26 | 1.28 | 1.13 | 0.57 |
| 78I1, 72A | 0.56 | 1.27 | 1.66 | 1.11 | 0.93 | 0.52 |
| 78M1, 72A | 0.33 | 1.39 | 1.50 | 1.44 | 1.44 | 0.92 |
| 78T1, 72A | 0.40 | 1.07 | 1.20 | 1.25 | 1.08 | 0.54 |
| 78W1, 72A | 0.32 | 0.49 | 0.53 | 0.57 | 0.53 | 0.29 |
| 82A, 106A, 72A | 0.29 | 0.11 | 0.13 | 0.18 | 0.13 | 0.05 |
| 82A, 72A | 0.41 | 1.55 | 1.56 | 1.67 | 1.53 | 0.84 |
| 82A1, 72A | 0.31 | 0.73 | 0.66 | 0.78 | 0.80 | 0.26 |
| 82F1, 72A | 0.27 | 0.68 | 0.76 | 1.08 | 0.78 | 0.41 |
| 82I3, 72A | 0.24 | 0.67 | 0.45 | 0.52 | 0.54 | 0.36 |
| 82M1, 72A | 0.27 | 0.97 | 0.75 | 0.94 | 0.92 | 0.54 |
| 82V1, 72A | 0.33 | 0.86 | 0.76 | 0.74 | 0.65 | 0.48 |
| 82Y2, 72A | 0.33 | 0.65 | 1.57 | 1.53 | 1.53 | 0.88 |
| 91A, 72A | 0.21 | 0.86 | 0.91 | 0.83 | 0.85 | 0.80 |
| 93L, 72A | 0.41 | 0.36 | 0.81 | 1.03 | 1.05 | 0.62 |
| 93M, 72A | 0.33 | 0.93 | 1.19 | 1.28 | 1.24 | 0.75 |

TABLE 4

| Mutations | Ro | DR/DR AA | DR/DR LNA | DR/DR LA | DR/DR OA | DR/DR PA | DR/DR POA | DR/DR SA | |
|---|---|---|---|---|---|---|---|---|---|
| 21W 72A | 0.616 | 3.829 | 2.550 | 2.551 | 2.808 | 1.637 | 2.120 | 1.946 | Large Response, Favors AA |
| 21W 78I 72A | 0.664 | 6.322 | 4.024 | 4.381 | 4.703 | 2.759 | 3.284 | 3.396 | |
| 21W 78F 72A | 0.604 | 4.264 | 1.694 | 1.597 | 1.843 | 0.851 | 1.217 | 1.161 | |
| 21W 78A 102V 72A | 0.388 | 4.923 | 1.628 | 2.749 | 3.261 | 1.721 | 1.585 | 3.092 | |
| 21F 78I 102F 72A | 0.400 | 4.836 | 3.006 | 2.872 | 3.312 | 2.383 | 2.788 | 2.367 | |
| 21F 78V 102V 72A | 0.288 | 4.511 | 3.775 | 4.204 | 4.223 | 2.756 | 3.365 | 3.120 | |
| 21Y 78I 102I 72A | 0.291 | 3.536 | 2.454 | 2.879 | 3.424 | 1.870 | 2.089 | 2.774 | |
| 21Y, 72A | 0.432 | 2.378 | 1.881 | 2.015 | 1.982 | 1.094 | | | |
| 38Y 62W 117A 72A | 0.554 | 2.353 | 1.237 | 1.848 | 1.896 | 0.316 | 0.272 | 0.854 | Favors AA |
| 72S 73Q 74A | 0.295 | 2.290 | 2.077 | 2.140 | 1.875 | 1.896 | 2.293 | 1.311 | |
| 38Y 117A 72A | 0.350 | 2.216 | 1.547 | 1.869 | 1.976 | 0.933 | 0.839 | 1.201 | |
| 38Y, 72A | 0.213 | 2.081 | 1.884 | 1.818 | 1.717 | 1.518 | | | |
| 14M 18L 31W 73I 117G 72A | 0.580 | 2.032 | 1.869 | 2.034 | 1.712 | 0.998 | 1.569 | 0.487 | |
| 38H 62W 106V 117A 72A | 0.284 | 2.007 | 1.796 | 1.337 | 1.239 | 1.002 | 1.145 | 0.947 | |
| 14L 31W 117V 72A | 0.259 | 1.972 | 1.894 | 2.027 | 1.580 | 1.304 | 1.768 | 0.742 | |
| 38M, 72A | 0.261 | 1.850 | 1.697 | 1.805 | 1.630 | 1.131 | | | |
| 18G 31F 73L 72A | 0.225 | 1.785 | 1.235 | 1.520 | 1.365 | 1.025 | 1.235 | 1.690 | |
| 38M 104S 115A 74F 72A | 0.325 | 1.690 | 1.615 | 1.778 | 1.155 | 0.498 | 1.172 | 0.356 | |
| 38Q 62I 106I 117A 72A | 0.215 | 1.656 | 0.930 | 1.288 | 1.167 | 0.550 | 0.473 | 0.663 | |
| 62Y, 72A | 0.238 | 1.598 | 1.395 | 1.545 | 1.439 | 1.037 | | | |
| 38Y 72G 117M | 0.204 | 1.541 | 1.228 | 1.233 | 1.137 | 0.574 | | | |
| 38A 106V 117A 72A | 0.418 | 1.492 | 0.541 | 0.229 | 0.368 | 0.033 | 0.121 | 0.065 | |
| 115W, 72A | 0.367 | 1.483 | 1.396 | 1.486 | 1.352 | 0.805 | | | |
| 72A 117A | 0.273 | 1.480 | 0.689 | 1.193 | 1.080 | 0.433 | | | |
| 117S, 72A | 0.357 | 1.467 | 1.133 | 1.533 | 1.258 | 0.593 | | | |
| 117A, 72A | 0.270 | 1.332 | 0.631 | 1.045 | 0.947 | 0.331 | | | |
| 14L 18I 31L 73F 117A 72A | 0.255 | 1.297 | 0.639 | 0.707 | 0.300 | 0.121 | 0.235 | 0.077 | |
| 38M 72G 117F | 0.241 | 1.280 | 0.733 | 0.748 | 0.686 | 0.438 | | | |
| 62N 106F 117A 72A | 0.224 | 1.265 | 0.756 | 0.985 | 0.864 | 0.430 | 0.341 | 0.490 | |
| 49N, 72A | 0.345 | 1.255 | 1.181 | 1.099 | 1.108 | 0.740 | | | |
| 14L 18T 31E 73G 117G 72A | 0.395 | 1.236 | 1.133 | 1.107 | 1.096 | 0.712 | 1.072 | 0.413 | |
| 14L 18L 31L 73G 117V 72A | 0.440 | 1.180 | 1.139 | 1.170 | 0.031 | 0.377 | 0.180 | 0.170 | |
| 23L, 72A | 0.229 | 1.174 | 1.025 | 1.041 | 1.057 | 0.928 | | | |
| 78Y, 72A | 0.314 | 1.172 | 0.871 | 0.908 | 0.845 | 0.520 | | | |
| 78I, 72A | 0.176 | 1.138 | 0.958 | 0.874 | 0.923 | 0.748 | | | |

TABLE 4-continued

| Mutations | Ro | DR/DR AA | DR/DR LNA | DR/DR LA | DR/DR OA | DR/DR PA | DR/DR POA | DR/DR SA | |
|---|---|---|---|---|---|---|---|---|---|
| 106W, 72A | 0.241 | 1.106 | 1.030 | 1.042 | 0.991 | 0.407 | | | |
| 78V, 72A | 0.255 | 1.093 | 0.798 | 0.865 | 0.864 | 0.615 | | | |
| 55I, 72A | 0.181 | 1.079 | 0.885 | 0.834 | 0.901 | 0.774 | | | |
| 38Q 106W 117A 72A | 0.301 | 1.078 | 0.795 | 0.860 | 0.899 | 0.444 | 0.970 | 0.281 | |
| 104R, 72A | 0.436 | 1.075 | 0.904 | 0.962 | 0.957 | 0.791 | | | |
| 119C, 72A | 0.679 | 1.063 | 1.001 | 1.022 | 0.971 | 0.355 | | | |
| 82F, 72A | 0.139 | 1.029 | 0.334 | 0.422 | 0.403 | 0.223 | | | |
| 104N, 72A | 0.396 | 1.018 | 0.391 | 0.385 | 0.408 | 0.406 | | | |
| 38H, 72A | 0.204 | 0.998 | 0.864 | 0.905 | 0.955 | 0.624 | | | |
| 73V, 72A | 0.300 | 0.976 | 0.496 | 0.396 | 0.603 | 0.475 | | | |
| 38I 72G | 0.290 | 0.964 | 0.701 | 0.772 | 0.861 | 0.419 | | | |
| 14L 18S 31L 73V 117A 72A | 0.486 | 0.951 | 0.673 | 0.534 | 0.020 | 0.028 | −0.003 | 0.007 | |
| 21V, 72A | 0.269 | 0.939 | 0.889 | 0.871 | 0.739 | 0.462 | | | |
| 11V, 72A | 0.363 | 0.932 | 0.763 | 0.825 | 0.552 | 0.732 | | | |
| 14I 72G 117V | 0.312 | 0.928 | 0.547 | 0.622 | 0.337 | 0.085 | | | |
| 14V 18L 73V 117A 72A | 0.110 | 0.926 | 0.624 | 0.557 | 0.307 | 0.249 | 0.597 | 0.105 | |
| 115N, 72A | 0.164 | 0.918 | 0.726 | 0.777 | 0.711 | 0.558 | | | |
| 14L 18L 73L 117A 72A | 0.372 | 0.905 | 0.641 | 0.657 | 0.355 | 0.071 | 0.410 | 0.031 | |
| 115H, 72A | 0.155 | 0.891 | 0.697 | 0.741 | 0.675 | 0.514 | | | |
| 14Q 18S 73I 117W 72A | 0.487 | 0.878 | 0.894 | 0.784 | 0.809 | 0.559 | 0.834 | −0.044 | |
| 14L 72G 117V | 0.280 | 0.873 | 0.513 | 0.548 | 0.297 | 0.055 | | | |
| 14L 72G | 0.377 | 0.873 | 0.886 | 0.817 | 0.730 | 0.334 | | | |
| 73T, 72A | 0.157 | 0.872 | 0.765 | 0.768 | 0.778 | 0.621 | | | |
| 72G | 0.307 | 0.871 | 0.590 | 0.544 | 0.628 | 0.307 | | | |
| 104G, 72A | 0.162 | 0.866 | 0.687 | 0.665 | 0.691 | 0.650 | | | |
| 55L, 72A | 0.155 | 0.863 | 0.719 | 0.706 | 0.822 | 0.631 | | | |
| 102F, 72A | 0.218 | 0.858 | 0.588 | 0.657 | 0.554 | 0.369 | | | |
| 14L 72A | 0.241 | 0.838 | 0.867 | 0.766 | 0.446 | 0.534 | | | |
| 119S, 72A | 0.313 | 0.781 | 0.734 | 0.457 | 0.714 | 0.373 | | | |
| 82V, 72A | 0.263 | 0.757 | 0.456 | 0.519 | 0.461 | 0.345 | | | |
| 73L, 72A | 0.294 | 0.733 | 0.338 | 0.325 | 0.380 | 0.251 | | | |
| 11M, 72A | 0.325 | 0.697 | 0.651 | 0.576 | 0.463 | 0.543 | | | |
| 104F, 72A | 0.344 | 0.686 | 0.436 | 0.486 | 0.462 | 0.263 | | | |
| 68L, 72A | 0.207 | 0.658 | 0.520 | 0.530 | 0.547 | 0.524 | | | |
| 17I, 72A | 0.258 | 0.640 | 0.541 | 0.499 | 0.624 | 0.283 | | | |
| 17V, 72A | 0.305 | 0.639 | 0.586 | 0.549 | 0.558 | 0.308 | | | |
| 34E, 72A | 0.317 | 0.618 | 0.571 | 0.604 | 0.486 | 0.482 | | | |
| 18L 73V 72A | 0.364 | 0.615 | 0.126 | 0.069 | 0.142 | 0.083 | 0.107 | 0.359 | |
| 55Q, 72A | 0.225 | 0.600 | 0.492 | 0.474 | 0.536 | 0.428 | | | |
| 17M, 72A | 0.296 | 0.590 | 0.532 | 0.489 | 0.490 | 0.281 | | | |
| 55V, 72A | 0.169 | 0.581 | 0.477 | 0.432 | 0.468 | 0.374 | | | |
| 106M, 72A | 0.231 | 0.554 | 0.490 | 0.485 | 0.510 | 0.183 | | | |
| 117W, 72A | 0.294 | 0.551 | 0.461 | 0.446 | 0.388 | 0.339 | | | |
| 119A, 72A | 0.304 | 0.540 | 0.520 | 0.450 | 0.490 | 0.200 | | | |
| 21I, 72A | 0.241 | 0.531 | 0.412 | 0.365 | 0.310 | 0.162 | | | |
| 17L, 72A | 0.251 | 0.525 | 0.447 | 0.420 | 0.459 | 0.279 | | | |
| 11Y, 72A | 0.309 | 0.516 | 0.311 | 0.330 | 0.156 | 0.296 | | | |
| 23Y, 72A | 0.265 | 0.492 | 0.443 | 0.442 | 0.412 | 0.281 | | | |
| 55Y, 72A | 0.124 | 0.471 | 0.335 | 0.324 | 0.329 | 0.249 | | | |
| 78A, 72A | 0.239 | 0.433 | 0.429 | 0.372 | 0.350 | 0.190 | | | |
| 11W, 72A | 0.262 | 0.430 | 0.357 | 0.344 | 0.227 | 0.199 | | | |
| 104Y, 72A | 0.878 | 0.364 | 0.278 | 0.265 | 0.236 | 0.140 | | | |
| 38Y 18L 73V 72A | 0.386 | 1.172 | 0.133 | 0.034 | 0.235 | 0.067 | 0.023 | 0.824 | AA and SA specific |
| 18L 73V 72A | 0.455 | 0.475 | −0.028 | −0.092 | 0.030 | 0.010 | −0.027 | 0.427 | |
| 18L 55L 73I 72A | 0.474 | 0.443 | −0.044 | −0.129 | 0.021 | 0.007 | −0.030 | 0.423 | |
| 18L 73L 72A | 0.283 | 0.441 | 0.090 | 0.019 | 0.021 | −0.004 | 0.092 | 0.254 | |
| 73I 72A | 0.276 | 0.408 | 0.099 | 0.039 | 0.045 | 0.015 | 0.117 | 0.242 | |
| 18G 31F 73L 72A | 0.225 | 1.785 | 1.235 | 1.520 | 1.365 | 1.025 | 1.235 | 1.690 | |
| 72F | 0.520 | 0.401 | 0.592 | 0.612 | 0.571 | 0.456 | | | AA lowest |
| 72Y | 0.386 | 0.346 | 0.594 | 0.637 | 0.557 | 0.415 | | | |
| 74F, 72A | 0.28 | 0.44 | 1.04 | 0.67 | 0.51 | 0.93 | | | |
| 72T 73W 74G | 0.205 | 0.687 | 1.702 | 1.348 | 0.822 | 1.817 | 2.770 | 0.305 | SA and AA lowest |
| 38Y 74F 72A | 0.191 | 0.605 | 1.166 | 0.926 | 0.646 | 1.397 | 1.514 | 0.362 | |
| 73W 74I | 0.335 | 0.757 | 1.325 | 1.130 | 0.912 | 1.884 | 2.697 | 0.423 | |
| 73W 74T | 0.368 | 1.456 | 3.286 | 2.480 | 1.902 | 3.883 | 5.818 | 0.726 | |
| 60T 104T 115W 74F 72A | 0.136 | 0.873 | 2.017 | 1.609 | 1.149 | 1.920 | 2.511 | 0.633 | |
| 72V 73L 74W | 0.248 | 0.500 | 1.209 | 1.225 | 0.648 | 1.276 | 1.710 | 0.348 | |
| 72H 73P 74L | 0.933 | 4.597 | 6.352 | 5.429 | 3.919 | 5.260 | 7.165 | 1.474 | Large Response, Favors POA, LNA |
| 72G 73W 74E | 0.576 | 4.229 | 5.501 | 5.045 | 2.755 | 3.944 | 6.069 | 0.955 | |
| 72A 73W 74E | 0.503 | 4.093 | 5.422 | 4.686 | 3.277 | 4.937 | 6.615 | 1.289 | |
| 72T 73W 74S | 0.574 | 4.129 | 4.826 | 4.612 | 4.177 | 4.155 | 5.826 | 1.620 | |
| 72S 73W 74E | 0.520 | 3.751 | 4.799 | 4.079 | 3.212 | 4.210 | 6.109 | 1.285 | |
| 72A 73W 74S | 0.353 | 3.211 | 4.401 | 3.806 | 3.155 | 4.039 | 4.864 | 1.095 | |
| 72S 73W 74N | 0.639 | 3.770 | 4.220 | 3.977 | 3.490 | 3.333 | 4.867 | 1.255 | |
| 72S 73W 74S | 0.597 | 3.545 | 4.147 | 3.787 | 2.863 | 3.536 | 4.656 | 1.106 | |

TABLE 4-continued

| Mutations | Ro | DR/DR AA | DR/DR LNA | DR/DR LA | DR/DR OA | DR/DR PA | DR/DR POA | DR/DR SA | |
|---|---|---|---|---|---|---|---|---|---|
| 73W 72A 74F | 0.567 | 3.378 | 3.875 | 3.718 | 3.255 | 3.264 | 5.256 | 1.485 | |
| 72T 73W 74E | 0.312 | 2.442 | 3.818 | 3.254 | 2.200 | 3.842 | 5.353 | 0.877 | |
| 72T 74V | 0.249 | 2.680 | 3.680 | 3.630 | 2.957 | 3.149 | 4.074 | 1.781 | |
| 72G 73W | 0.602 | 2.260 | 3.637 | 2.698 | 1.106 | 2.968 | 4.082 | 0.294 | |
| 72T 73V 74V | 0.215 | 3.237 | 3.618 | 3.502 | 3.166 | 2.987 | 4.015 | 1.918 | |
| 72T 73V 74L | 0.386 | 2.774 | 3.508 | 3.165 | 2.832 | 2.674 | 3.642 | 1.411 | |
| 72W 73T 74G | 0.500 | 2.808 | 3.394 | 3.099 | 2.514 | 2.934 | 4.105 | 1.040 | |
| 72S 73L 74A | 0.347 | 3.336 | 3.322 | 3.455 | 3.495 | 3.293 | 3.923 | 2.574 | |
| 72T 74I | 0.269 | 2.502 | 3.169 | 3.156 | 2.660 | 2.476 | 3.410 | 1.806 | |
| 72S 73V 74V | 0.356 | 2.712 | 3.088 | 3.085 | 2.556 | 2.091 | 3.322 | 1.058 | |
| 72T 73W 74L | 0.292 | 2.721 | 3.009 | 2.819 | 2.340 | 2.727 | 3.574 | 1.217 | |
| 72T 73Q 74A | 0.257 | 2.392 | 2.850 | 3.163 | 3.136 | 3.473 | 3.632 | 2.318 | |
| 72T 73V 74S | 0.241 | 2.540 | 2.579 | 2.611 | 2.670 | 2.629 | 2.909 | 2.195 | |
| 72S 73M 74A | 0.358 | 2.759 | 2.567 | 2.470 | 2.443 | 2.524 | 2.854 | 1.776 | |
| 72T 73V 74N | 0.280 | 2.484 | 2.362 | 2.407 | 2.491 | 2.250 | 2.816 | 1.942 | |
| 72S 73P 74I | 0.324 | 2.154 | 3.091 | 2.792 | 2.162 | 2.210 | 3.155 | 1.337 | Favors POA and LNA |
| 72A 73P 74V | 0.377 | 2.354 | 2.845 | 2.735 | 2.187 | 2.406 | 3.613 | 1.178 | |
| 18V 31A 73W 72A | 0.352 | 1.761 | 2.770 | 2.540 | 1.738 | 2.218 | 3.184 | 0.722 | |
| 72A 73W 74V | 0.393 | 1.768 | 2.752 | 2.338 | 1.574 | 2.525 | 3.856 | 0.602 | |
| 72T 73V 74A | 0.242 | 2.180 | 2.597 | 2.435 | 1.950 | 2.362 | 3.011 | 1.146 | |
| 72G 73F 74E | 0.381 | 0.910 | 2.415 | 1.467 | 0.585 | 0.981 | 2.519 | 0.239 | |
| 18I 31I 55M 73V 72A | 0.362 | 1.710 | 2.408 | 1.981 | 1.188 | 1.883 | 2.478 | 0.502 | |
| 72V 73W 74N | 0.207 | 1.191 | 2.384 | 1.726 | 1.146 | 2.229 | 3.507 | 0.468 | |
| 18I 31A 73F 72A | 0.330 | 1.314 | 2.318 | 1.732 | 0.950 | 1.515 | 2.730 | 0.404 | |
| 18I 31A 73F 72A | 0.330 | 1.296 | 2.203 | 1.652 | 0.995 | 1.372 | 2.522 | 0.406 | |
| 18I 31Y 73V 72A | 0.365 | 1.801 | 2.176 | 2.242 | 1.818 | 1.615 | 2.088 | 1.047 | |
| 72A 73W 74A | 0.268 | 0.892 | 2.093 | 1.466 | 0.933 | 1.942 | 3.016 | 0.330 | |
| 72V 73W 74S | 0.270 | 1.424 | 2.044 | 1.819 | 1.477 | 1.789 | 2.662 | 0.574 | |
| 18V 31A 73F 72A | 0.308 | 1.142 | 2.036 | 1.527 | 0.828 | 1.510 | 2.677 | 0.375 | |
| 60T 104T 115W 74F 72A | 0.136 | 0.873 | 2.017 | 1.609 | 1.149 | 1.920 | 2.511 | 0.633 | |
| 14Q 18L 31A 73W 117V 72A | 0.334 | 1.558 | 1.958 | 1.942 | 1.478 | 1.084 | 2.008 | 0.384 | |
| 18I 31V 73G 72A | 0.360 | 1.348 | 1.946 | 1.715 | 0.968 | 1.630 | 2.122 | 0.543 | |
| 18V 31A 55W 73W 72A | 0.344 | 1.130 | 1.887 | 1.555 | 0.913 | 1.505 | 2.042 | 0.392 | |
| 18I 31I 55M 73I 72A | 0.391 | 1.354 | 1.803 | 1.516 | 0.822 | 1.546 | 1.903 | 0.382 | |
| 72I 73W 74N | 0.229 | 0.791 | 1.794 | 1.194 | 0.779 | 2.091 | 3.236 | 0.329 | |
| 73F 72A | 0.299 | 1.051 | 1.775 | 1.171 | 0.630 | 1.118 | 2.381 | 0.399 | |
| 18I 31L 55L 72A | 0.318 | 1.285 | 1.736 | 1.442 | 0.759 | 1.523 | 2.011 | 0.310 | |
| 72S 73W 74G | 0.321 | 1.012 | 1.706 | 1.375 | 0.970 | 1.653 | 2.422 | 0.411 | |
| 73T 72A 74F | 0.300 | 0.939 | 1.661 | 1.389 | 1.161 | 1.632 | 2.450 | 0.519 | |
| 74T 72A 73F | 0.181 | 0.852 | 1.635 | 1.185 | 0.634 | 1.150 | 2.309 | 0.273 | |
| 55V 73F 72A | 0.328 | 0.864 | 1.566 | 1.223 | 0.661 | 1.082 | 2.264 | 0.285 | |
| 74E 72A 73F | 0.259 | 0.703 | 1.558 | 1.093 | 0.575 | 1.026 | 2.395 | 0.251 | |
| 73P 72A 74F | 0.265 | 1.078 | 1.518 | 0.838 | 0.868 | 1.278 | 1.776 | 0.494 | |
| 18V 31F 73M 72A | 0.314 | 1.014 | 1.511 | 1.296 | 0.794 | 1.395 | 1.538 | 0.383 | |
| 74S 72A 73F | 0.230 | 0.893 | 1.433 | 1.035 | 0.630 | 1.158 | 2.413 | 0.337 | |
| 38I 74F 72A | 0.276 | 0.787 | 1.395 | 1.162 | 0.764 | 1.343 | 2.112 | 0.503 | |
| 72G 73F 74N | 0.513 | 0.617 | 1.367 | 0.454 | −0.032 | 0.456 | 1.499 | −0.043 | |
| 73W 74I | 0.335 | 0.757 | 1.325 | 1.130 | 0.912 | 1.884 | 2.697 | 0.423 | |
| 72V 73L 74W | 0.248 | 0.500 | 1.209 | 1.225 | 0.648 | 1.276 | 1.710 | 0.348 | |
| 18V 31F 55L 72A | 0.303 | 0.921 | 1.180 | 0.996 | 0.649 | 1.035 | 1.353 | 0.358 | |
| 18I 31V 55V 73V 72A | 0.362 | 0.632 | 1.179 | 0.853 | 0.448 | 0.974 | 1.236 | 0.233 | |
| 74Q 72A 73F | 0.251 | 0.465 | 1.025 | 0.711 | 0.390 | 0.649 | 1.479 | 0.177 | |
| 72E 73V 74A | 0.296 | 0.478 | 0.784 | 0.735 | 0.524 | 0.736 | 1.093 | 0.234 | |
| 72G 73F 74E | 0.381 | 0.910 | 2.415 | 1.467 | 0.585 | 0.981 | 2.519 | 0.239 | |
| 18I 31A 73F 72A | 0.330 | 1.296 | 2.203 | 1.652 | 0.995 | 1.372 | 2.522 | 0.406 | |
| 18I 31L 55L 72A | 0.318 | 1.285 | 1.736 | 1.442 | 0.759 | 1.523 | 2.011 | 0.310 | |
| 72A 73P 74E | 0.199 | 1.975 | 1.863 | 1.741 | 1.802 | 1.732 | 2.087 | 1.512 | |
| 18I 31V 55V 73V 72A | 0.362 | 0.632 | 1.179 | 0.853 | 0.448 | 0.974 | 1.236 | 0.233 | |
| 60T 104T 115W 74F 72A | 0.136 | 0.873 | 2.017 | 1.609 | 1.149 | 1.920 | 2.511 | 0.633 | |
| 18V 31A 55W 73W 72A | 0.344 | 1.130 | 1.887 | 1.555 | 0.913 | 1.505 | 2.042 | 0.392 | |
| 18I 31I 55M 73I 72A | 0.391 | 1.354 | 1.803 | 1.516 | 0.822 | 1.546 | 1.903 | 0.382 | |
| 18I 31I 55M 73V 72A | 0.362 | 1.710 | 2.408 | 1.981 | 1.188 | 1.883 | 2.478 | 0.502 | |
| 73P 72A 74F | 0.265 | 1.078 | 1.518 | 0.838 | 0.868 | 1.278 | 1.776 | 0.494 | |
| 18V 31A 73W 72A | 0.352 | 1.761 | 2.770 | 2.540 | 1.738 | 2.218 | 3.184 | 0.722 | |
| 14Q 18L 31A 73W 117V 72A | 0.334 | 1.558 | 1.958 | 1.942 | 1.478 | 1.084 | 2.008 | 0.384 | |
| 18I 31M 55M 72A | 0.352 | 1.010 | 1.358 | 1.134 | 0.601 | 1.099 | 1.353 | 0.296 | |
| 18I 31V 73G 72A | 0.360 | 1.348 | 1.946 | 1.715 | 0.968 | 1.630 | 2.122 | 0.543 | |
| 18V 31F 55L 72A | 0.303 | 0.921 | 1.180 | 0.996 | 0.649 | 1.035 | 1.353 | 0.358 | |
| 18V 31F 73M 72A | 0.314 | 1.014 | 1.511 | 1.296 | 0.794 | 1.395 | 1.538 | 0.383 | |
| 18V 31A 55I 72A | 0.345 | 0.989 | 1.580 | 1.334 | 0.791 | 1.280 | 1.563 | 0.420 | |
| 72T 73V 74A | 0.242 | 2.180 | 2.597 | 2.435 | 1.950 | 2.362 | 3.011 | 1.146 | |
| 72S 73P 74I | 0.324 | 2.154 | 3.091 | 2.792 | 2.162 | 2.210 | 3.155 | 1.337 | |
| 72T 73I 74A | 0.293 | 2.148 | 1.944 | 1.795 | 1.721 | 1.687 | 2.320 | 1.359 | |
| 72S 74A | 0.208 | 1.648 | 2.002 | 2.037 | 1.575 | 1.615 | 2.034 | 1.114 | |
| 72S 73V 74A | 0.340 | 2.127 | 2.330 | 2.397 | 2.295 | 2.601 | 2.727 | 1.572 | |
| 72T 73G 74I | 0.311 | 2.226 | 2.317 | 2.577 | 2.414 | 2.177 | 2.771 | 1.755 | |
| 72S 73Q 74A | 0.295 | 2.290 | 2.077 | 2.140 | 1.875 | 1.896 | 2.293 | 1.311 | |

TABLE 4-continued

| Mutations | Ro | DR/DR AA | DR/DR LNA | DR/DR LA | DR/DR OA | DR/DR PA | DR/DR POA | DR/DR SA | |
|---|---|---|---|---|---|---|---|---|---|
| 18I 31F 72A | 0.314 | 2.043 | 3.027 | 2.707 | 1.761 | 2.037 | 2.659 | 0.950 | Favors LNA |
| 18I 31Y 72A | 0.345 | 2.205 | 2.813 | 2.790 | 2.096 | 1.762 | 2.639 | 0.994 | |
| 18I 31Y 73G 72A | 0.298 | 1.796 | 2.706 | 2.559 | 1.632 | 1.886 | 2.637 | 0.860 | |
| 72T 74S | 0.251 | 2.035 | 2.621 | 2.469 | 2.252 | 2.209 | 2.471 | 1.779 | |
| 14R 18L 31S 73F 117E 72A | 0.524 | 1.241 | 2.296 | 1.947 | 1.146 | 0.693 | 1.290 | 0.378 | |
| 14R 18L 73L 117D 72A | 0.647 | 1.029 | 1.790 | 1.766 | 0.847 | 0.294 | 0.801 | 0.213 | |
| 72A 74N | 0.162 | 1.614 | 1.701 | 1.681 | 1.629 | 1.308 | 1.536 | 1.299 | |
| 14L 18L 31S 73W 117V 72A | 0.264 | 1.458 | 1.631 | 1.569 | 1.208 | 0.692 | 1.356 | 0.329 | |
| 18V 31A 55I 72A | 0.345 | 0.989 | 1.580 | 1.334 | 0.791 | 1.280 | 1.563 | 0.420 | |
| 18V 31V 73I 72A | 0.329 | 0.863 | 1.531 | 1.151 | 0.670 | 1.302 | 1.334 | 0.311 | |
| 18I 31L 73G 72A | 0.367 | 0.981 | 1.525 | 1.146 | 0.595 | 1.137 | 1.377 | 0.267 | |
| 14L 18L 73W 117S 72A | 0.562 | 1.010 | 1.499 | 1.385 | 0.374 | 0.259 | 0.750 | −0.005 | |
| 38W 106H 117A 72A | 0.414 | 1.326 | 1.397 | 1.248 | 0.831 | 0.426 | 1.098 | 0.071 | |
| 18I 31L 72A | 0.310 | 1.054 | 1.384 | 1.198 | 0.719 | 1.182 | 1.187 | 0.305 | |
| 18I 31M 55M 72A | 0.352 | 1.010 | 1.358 | 1.134 | 0.601 | 1.099 | 1.353 | 0.296 | |
| 18I 55G 73M 72A | 0.303 | 0.895 | 1.284 | 1.127 | 0.574 | 1.137 | 1.201 | 0.360 | |
| 18V 31Y 55I 73G 72A | 0.383 | 1.007 | 1.228 | 1.220 | 0.994 | 0.780 | 1.106 | −0.094 | |
| 14Q 18S 73I 117W 72A | 0.487 | 0.878 | 0.894 | 0.784 | 0.809 | 0.559 | 0.834 | −0.044 | |
| 119M, 72A | 0.343 | 1.087 | 2.280 | 1.184 | 1.191 | 0.722 | | | Favors LNA |
| 78F, 72A | 0.219 | 2.001 | 2.033 | 1.955 | 1.912 | 1.416 | | | |
| 14M 72M 117A | 0.305 | 1.649 | 2.031 | 1.956 | 1.054 | 0.870 | | | |
| 38Q, 72A | 0.204 | 1.976 | 1.986 | 1.936 | 1.842 | 1.551 | | | |
| 73F, 72A | 0.330 | 1.208 | 1.861 | 1.234 | 0.728 | 1.128 | | | |
| 38T, 72A | 0.297 | 1.598 | 1.639 | 1.577 | 1.547 | 1.022 | | | |
| 17W, 72A | 0.175 | 1.421 | 1.611 | 1.416 | 1.241 | 1.067 | | | |
| 62P, 72A | 0.216 | 1.548 | 1.581 | 1.572 | 1.448 | 1.247 | | | |
| 31Q, 72A | 0.376 | 1.024 | 1.494 | 1.465 | 1.313 | 1.039 | | | |
| 38S, 72A | 0.311 | 1.175 | 1.295 | 1.286 | 1.235 | 0.724 | | | |
| 14W 72M 117A | 0.322 | 0.945 | 1.286 | 1.009 | 0.706 | 0.515 | | | |
| 36V, 72A | 0.330 | 1.026 | 1.082 | 1.062 | 0.869 | 0.713 | | | |
| 74F, 72A | 0.28 | 0.44 | 1.04 | 0.67 | 0.51 | 0.93 | | | |
| 36I, 72A | 0.250 | 0.812 | 1.004 | 0.884 | 0.773 | 0.815 | | | |
| 23W, 72A | 0.449 | 0.618 | 0.956 | 0.794 | 0.448 | 0.492 | | | |
| 17Y, 72A | 0.647 | 0.729 | 0.806 | 0.712 | 0.732 | 0.500 | | | |
| 31V, 72A | 0.613 | 0.395 | 0.776 | 0.384 | 0.081 | 0.206 | | | |
| 14M, 72A | 0.326 | 0.619 | 0.684 | 0.685 | 0.412 | 0.452 | | | |
| 117D, 72A | 0.389 | 0.352 | 0.407 | 0.380 | 0.294 | 0.142 | | | |
| 31I, 72A | 0.680 | 0.303 | 0.413 | 0.168 | −0.213 | 0.091 | | | Favors LNA largest OA neg |
| 104N, 72A | 0.396 | 1.018 | 0.391 | 0.385 | 0.408 | 0.406 | | | LNA lowest |
| 14L 18L 31Y 73L 117A 72A | 0.581 | 2.987 | 2.818 | 2.948 | 1.908 | 1.444 | 2.317 | 0.762 | Favors PUFA, POA |
| 18I 31F 73V 72A | 0.355 | 2.649 | 2.738 | 3.096 | 2.257 | 1.893 | 2.665 | 1.294 | |
| 104T 115A 74F 72A | 0.287 | 2.635 | 2.206 | 2.231 | 1.621 | 0.720 | 1.661 | 0.877 | |
| 18I 31Y 73I 72A | 0.340 | 2.487 | 2.865 | 3.031 | 2.322 | 1.825 | 2.620 | 1.310 | |
| 18L 73F 117G 72A | 0.400 | 2.445 | 1.913 | 2.283 | 1.908 | 1.039 | 1.731 | 0.663 | |
| 18V 31Y 73V 72A | 0.343 | 2.400 | 2.605 | 2.780 | 2.349 | 1.534 | 2.376 | 1.330 | |
| 18V 31I 55L 73V 72A | 0.316 | 2.273 | 2.433 | 2.680 | 2.254 | 1.253 | 2.285 | 1.233 | |
| 14A 18Y 31W 73G 117V 72A | 0.261 | 0.365 | 0.940 | 1.018 | 0.518 | 0.421 | 0.883 | 0.158 | Favors LNA, LA |
| 31R, 72A | 0.182 | 0.250 | 0.437 | 0.405 | 0.227 | 0.342 | | | |
| 31E, 72A | 0.308 | 0.238 | 0.522 | 0.430 | 0.211 | 0.223 | | | |
| 74L, 72A | 0.172 | 0.222 | 0.404 | 0.305 | 0.188 | 0.361 | | | |
| 31T, 72A | 0.389 | 0.143 | 0.510 | 0.215 | −0.024 | 0.145 | | | |
| 18V 31Y 73I 72A | 0.359 | 1.946 | 2.537 | 2.619 | 2.007 | 1.784 | 2.528 | 1.139 | Favors LA, some LNA about same |
| 78F 102I 72A | 0.297 | 2.093 | 2.322 | 2.493 | 2.506 | 1.434 | 2.022 | 1.877 | |
| 38W, 72A | 0.231 | 1.350 | 1.336 | 2.413 | 1.583 | 1.552 | | | |
| 62W, 72A | 0.211 | 2.206 | 2.120 | 2.339 | 2.155 | 1.450 | | | |
| 18I 31Y 73V 72A | 0.365 | 1.801 | 2.176 | 2.242 | 1.818 | 1.615 | 2.088 | 1.047 | |
| 14I 18L 31W 73V 117G 72A | 0.470 | 2.037 | 1.960 | 2.047 | 1.756 | 1.236 | 1.770 | 0.606 | |
| 72S 74A | 0.208 | 1.648 | 2.002 | 2.037 | 1.575 | 1.615 | 2.034 | 1.114 | |
| 14M 18L 31W 73I 117G 72A | 0.580 | 2.032 | 1.869 | 2.034 | 1.712 | 0.998 | 1.569 | 0.487 | |
| 14L 31W 117V 72A | 0.259 | 1.972 | 1.894 | 2.027 | 1.580 | 1.304 | 1.768 | 0.742 | |
| 14Q 18L 31A 73W 117V 72A | 0.334 | 1.558 | 1.958 | 1.942 | 1.478 | 1.084 | 2.008 | 0.384 | |
| 49I, 72A | 0.362 | 1.796 | 1.820 | 1.839 | 1.804 | 1.162 | | | |
| 70Q, 72A | 0.307 | 1.546 | 1.622 | 1.819 | 1.604 | 0.868 | | | |
| 14L 18L 31W 73W 117L 72A | 0.201 | 1.772 | 1.640 | 1.782 | 1.085 | 0.970 | 2.059 | 0.294 | |
| 38M 104S 115A 74F 72A | 0.325 | 1.690 | 1.615 | 1.778 | 1.155 | 0.498 | 1.172 | 0.356 | |
| 14R 18L 73L 117D 72A | 0.647 | 1.029 | 1.790 | 1.766 | 0.847 | 0.294 | 0.801 | 0.213 | |
| 31F, 72A | 0.492 | 1.210 | 1.647 | 1.759 | 1.331 | 1.438 | | | |
| 23V, 72A | 0.167 | 1.464 | 1.351 | 1.731 | 1.561 | 1.475 | | | |
| 60I, 72A | 0.202 | 1.539 | 1.632 | 1.730 | 1.723 | 1.520 | | | |
| 11Q, 72A | 0.262 | 1.525 | 1.582 | 1.715 | 1.716 | 1.450 | | | |
| 104S, 72A | 0.242 | 1.638 | 1.538 | 1.715 | 1.663 | 1.570 | | | |
| 73Y, 72A | 0.282 | 1.529 | 1.603 | 1.711 | 1.537 | 0.982 | | | |
| 72A 74N | 0.162 | 1.614 | 1.701 | 1.681 | 1.629 | 1.308 | 1.536 | 1.299 | |
| 14I 18V 31W 73I 117V 72A | 0.287 | 1.553 | 1.495 | 1.668 | 0.887 | 0.652 | 1.411 | 0.283 | |

TABLE 4-continued

| Mutations | Ro | DR/DR AA | DR/DR LNA | DR/DR LA | DR/DR OA | DR/DR PA | DR/DR POA | DR/DR SA | |
|---|---|---|---|---|---|---|---|---|---|
| 62D, 72A | 0.230 | 1.485 | 1.576 | 1.598 | 1.574 | 1.385 | | | |
| 18L, 72A | 0.265 | 1.490 | 1.544 | 1.596 | 1.551 | 1.090 | | | |
| 14L 18L 31S 73W 117V 72A | 0.264 | 1.458 | 1.631 | 1.569 | 1.208 | 0.692 | 1.356 | 0.329 | |
| 21D, 72A | 0.359 | 1.301 | 1.478 | 1.562 | 1.345 | 0.707 | | | |
| 117S, 72A | 0.357 | 1.467 | 1.133 | 1.533 | 1.258 | 0.593 | | | |
| 31Q, 72A | 0.376 | 1.024 | 1.494 | 1.465 | 1.313 | 1.039 | | | |
| 14L 18L 73W 117S 72A | 0.562 | 1.010 | 1.499 | 1.385 | 0.374 | 0.259 | 0.750 | −0.005 | |
| 117Q, 72A | 0.368 | 1.214 | 1.236 | 1.374 | 1.134 | 0.631 | | | |
| 49M, 72A | 0.347 | 1.363 | 1.369 | 1.370 | 1.296 | 0.939 | | | |
| 38Q 62I 106I 117A 72A | 0.215 | 1.656 | 0.930 | 1.288 | 1.167 | 0.550 | 0.473 | 0.663 | |
| 60L, 72A | 0.236 | 1.075 | 1.260 | 1.285 | 1.272 | 1.095 | | | |
| 18V 31Y 55I 73G 72A | 0.383 | 1.007 | 1.228 | 1.220 | 0.994 | 0.780 | 1.106 | −0.094 | |
| 47M, 72A | 0.225 | 1.138 | 1.135 | 1.183 | 1.168 | 0.966 | | | |
| 31W, 72A | 0.462 | 0.993 | 1.031 | 1.147 | 0.868 | 0.618 | | | |
| 119L, 72A | 0.349 | 1.021 | 1.053 | 1.134 | 0.778 | 0.661 | | | |
| 74E 72A 73F | 0.259 | 0.703 | 1.558 | 1.093 | 0.575 | 1.026 | 2.395 | 0.251 | |
| 14L 38I 72A | 0.267 | 1.046 | 1.177 | 1.090 | 0.653 | 0.712 | | | |
| 40M, 72A | 0.195 | 0.993 | 1.021 | 1.086 | 0.990 | 0.691 | | | |
| 14W 18L 117S 72A | 0.228 | 0.976 | 0.835 | 1.063 | 0.904 | 0.377 | 0.811 | 0.297 | |
| 36V, 72A | 0.330 | 1.026 | 1.082 | 1.062 | 0.869 | 0.713 | | | |
| 40V, 72A | 0.164 | 1.013 | 1.059 | 1.057 | 1.002 | 0.867 | | | |
| 117H, 72A | 0.311 | 0.913 | 0.924 | 1.056 | 1.012 | 0.659 | | | |
| 117A, 72A | 0.270 | 1.332 | 0.631 | 1.045 | 0.947 | 0.331 | | | |
| 126K, 72A | 0.455 | 0.625 | 1.017 | 1.039 | 0.631 | 0.356 | | | |
| 38G, 72A | 0.301 | 0.996 | 0.992 | 1.003 | 0.945 | 0.447 | | | |
| 60A, 72A | 0.227 | 0.787 | 0.938 | 0.977 | 0.936 | 0.742 | | | |
| 18K, 72A | 0.359 | 0.800 | 0.925 | 0.967 | 0.803 | 0.544 | | | |
| 70H, 72A | 0.374 | 0.751 | 0.886 | 0.929 | 0.836 | 0.567 | | | |
| 36Q, 72A | 0.247 | 0.837 | 0.880 | 0.927 | 0.792 | 0.777 | | | |
| 117V, 72A | 0.153 | 0.805 | 0.767 | 0.924 | 0.774 | 0.498 | | | |
| 117T, 72A | 0.197 | 0.791 | 0.775 | 0.917 | 0.813 | 0.567 | | | |
| 60W, 72A | 0.185 | 0.670 | 0.739 | 0.837 | 0.763 | 0.595 | | | |
| 14V, 72A | 0.317 | 0.756 | 0.868 | 0.836 | 0.513 | 0.430 | | | |
| 106F, 72A | 0.294 | 0.754 | 0.706 | 0.812 | 0.815 | 0.369 | | | |
| 70S, 72A | 0.422 | 0.625 | 0.703 | 0.794 | 0.727 | 0.416 | | | |
| 14I, 72A | 0.391 | 0.572 | 0.899 | 0.792 | 0.572 | 0.586 | | | |
| 117I, 72A | 0.133 | 0.674 | 0.666 | 0.789 | 0.676 | 0.408 | | | |
| 117E, 72A | 0.196 | 0.656 | 0.638 | 0.753 | 0.659 | 0.402 | | | |
| 70W, 72A | 0.388 | 0.349 | 0.385 | 0.451 | 0.381 | 0.212 | | | |
| 18L 73V 72A | 0.364 | 0.615 | 0.126 | 0.069 | 0.142 | 0.083 | 0.107 | 0.359 | LA low |
| 73V, 72A | 0.300 | 0.976 | 0.496 | 0.396 | 0.603 | 0.475 | | | |
| 119S, 72A | 0.313 | 0.781 | 0.734 | 0.457 | 0.714 | 0.373 | | | LA & PA low |
| 72V 73L 74W | 0.248 | 0.500 | 1.209 | 1.225 | 0.648 | 1.276 | 1.710 | 0.348 | LA, POA high |
| 14L 18L 31L 73G 117V 72A | 0.440 | 1.180 | 1.139 | 1.170 | 0.031 | 0.377 | 0.180 | 0.170 | PUFA high |
| 78F 102I 72A | 0.297 | 2.093 | 2.322 | 2.493 | 2.506 | 1.434 | 2.022 | 1.877 | Favors OA |
| 102I, 72A | 0.217 | 1.461 | 1.763 | 1.902 | 1.929 | 1.169 | | | |
| 60F, 72A | 0.247 | 1.792 | 1.762 | 1.684 | 1.896 | 1.526 | | | |
| 91Y, 72A | 0.307 | 1.273 | 1.626 | 1.415 | 1.706 | 0.870 | | | |
| 38V 62V 117A 72A | 0.325 | 0.984 | 1.153 | 1.002 | 1.668 | 0.478 | 0.668 | 0.495 | |
| 91C, 72A | 0.334 | 1.201 | 1.420 | 1.371 | 1.470 | 0.794 | | | |
| 102L, 72A | 0.154 | 1.103 | 1.284 | 1.267 | 1.366 | 1.012 | | | |
| 34W, 72A | 0.187 | 1.060 | 1.130 | 1.110 | 1.210 | 0.920 | | | |
| 119I, 72A | 0.303 | 0.920 | 0.940 | 0.960 | 1.050 | 0.720 | | | |
| 117H, 72A | 0.311 | 0.913 | 0.924 | 1.056 | 1.012 | 0.659 | | | |
| 38H, 72A | 0.204 | 0.998 | 0.864 | 0.905 | 0.955 | 0.624 | | | |
| 18G 31W 73V 72A | 0.232 | 0.774 | 0.705 | 0.855 | 0.942 | 0.463 | 0.770 | 0.489 | |
| 102Y, 72A | 0.719 | 0.718 | 0.732 | 0.818 | 0.860 | 0.387 | | | |
| 72N | 0.310 | 0.652 | 0.702 | 0.770 | 0.831 | 0.441 | | | |
| 55L, 72A | 0.155 | 0.863 | 0.719 | 0.706 | 0.822 | 0.631 | | | |
| 106F, 72A | 0.294 | 0.754 | 0.706 | 0.812 | 0.815 | 0.369 | | | |
| 119V, 72A | 0.344 | 0.750 | 0.710 | 0.720 | 0.780 | 0.480 | | | |
| 93L, 72A | 0.312 | 0.680 | 0.680 | 0.670 | 0.770 | 0.560 | | | |
| 106H, 72A | 0.279 | 0.636 | 0.633 | 0.669 | 0.732 | 0.258 | | | |
| 106I, 72A | 0.291 | 0.481 | 0.624 | 0.563 | 0.661 | 0.223 | | | |
| 106V, 72A | 0.261 | 0.398 | 0.592 | 0.574 | 0.657 | 0.191 | | | |
| 60K, 72A | 0.465 | 0.461 | 0.582 | 0.619 | 0.626 | 0.310 | | | |
| 17I, 72A | 0.258 | 0.640 | 0.541 | 0.499 | 0.624 | 0.283 | | | |
| 106A, 72A | 0.249 | 0.389 | 0.518 | 0.515 | 0.596 | 0.164 | | | |
| 106N, 72A | 0.238 | 0.384 | 0.445 | 0.451 | 0.496 | 0.152 | | | |
| 106S, 72A | 0.258 | 0.321 | 0.403 | 0.355 | 0.478 | 0.149 | | | |
| 106T, 72A | 0.228 | 0.250 | 0.367 | 0.246 | 0.434 | 0.118 | | | |
| 106L, 72A | 0.299 | 0.383 | 0.364 | 0.382 | 0.427 | 0.183 | | | |
| 38A 106V 117A 72A | 0.418 | 1.492 | 0.541 | 0.229 | 0.368 | 0.033 | 0.121 | 0.065 | OA>>PA |
| 14L 18L 73L 117A 72A | 0.372 | 0.905 | 0.641 | 0.657 | 0.355 | 0.071 | 0.410 | 0.031 | |
| 38Y 62W 117A 72A | 0.554 | 2.353 | 1.237 | 1.848 | 1.896 | 0.316 | 0.272 | 0.854 | |
| 38W 106H 117A 72A | 0.414 | 1.326 | 1.397 | 1.248 | 0.831 | 0.426 | 1.098 | 0.071 | |
| 72G 73F 74N | 0.513 | 0.617 | 1.367 | 0.454 | −0.032 | 0.456 | 1.499 | −0.043 | Miscellaneous phenotypes |

TABLE 4-continued

| Mutations | Ro | DR/DR AA | DR/DR LNA | DR/DR LA | DR/DR OA | DR/DR PA | DR/DR POA | DR/DR SA | |
|---|---|---|---|---|---|---|---|---|---|
| 14L 18L 31L 73G 117V 72A | 0.440 | 1.180 | 1.139 | 1.170 | 0.031 | 0.377 | 0.180 | 0.170 | |
| 31V, 72A | 0.613 | 0.395 | 0.776 | 0.384 | 0.081 | 0.206 | | | |
| 11Y, 72A | 0.309 | 0.516 | 0.311 | 0.330 | 0.156 | 0.296 | | | |
| 14I 38I 72V | 0.205 | 0.715 | 0.926 | 0.862 | 0.398 | 0.844 | | | |
| 14I 72A | 0.345 | 0.825 | 0.997 | 0.944 | 0.478 | 0.762 | | | |
| 73F, 72A | 0.330 | 1.208 | 1.861 | 1.234 | 0.728 | 1.128 | | | |
| 11I, 72A | 0.382 | 0.584 | 0.507 | 0.546 | 0.387 | 1.186 | | | |
| 14L 72A | 0.241 | 0.838 | 0.867 | 0.766 | 0.446 | 0.534 | | | |
| 14L 38M 72A 117F | 0.213 | 0.861 | 0.921 | 0.830 | 0.458 | 0.472 | | | |
| 73F 72A | 0.299 | 1.051 | 1.775 | 1.171 | 0.630 | 1.118 | 2.381 | 0.399 | |
| 72H 73Y 74G | 0.205 | 0.600 | 0.591 | 0.472 | 0.140 | 0.486 | 0.986 | 0.052 | |
| 31I, 72A | 0.680 | 0.303 | 0.413 | 0.168 | −0.213 | 0.091 | | | OA neg |
| 18V 31Y 55I 73G 72A | 0.383 | 1.007 | 1.228 | 1.220 | 0.994 | 0.780 | 1.106 | −0.094 | SA very low to zero |
| 14Q 18S 73I 117W 72A | 0.487 | 0.878 | 0.894 | 0.784 | 0.809 | 0.559 | 0.834 | −0.044 | |
| 14L 18L 73W 117S 72A | 0.562 | 1.010 | 1.499 | 1.385 | 0.374 | 0.259 | 0.750 | −0.005 | |
| 38W 106H 117A 72A | 0.414 | 1.326 | 1.397 | 1.248 | 0.831 | 0.426 | 1.098 | 0.071 | low SA somewhat low PA |
| 18V 31Y 55I 73G 72A | 0.383 | 1.007 | 1.228 | 1.220 | 0.994 | 0.780 | 1.106 | −0.094 | |
| 72H 73Y 74G | 0.205 | 0.600 | 0.591 | 0.472 | 0.140 | 0.486 | 0.986 | 0.052 | |
| 72G 73F 74N | 0.513 | 0.617 | 1.367 | 0.454 | −0.032 | 0.456 | 1.499 | −0.043 | low OA and SA, AA and POA high |
| 73W 74T | 0.368 | 1.456 | 3.286 | 2.480 | 1.902 | 3.883 | 5.818 | 0.726 | Favors POA and PA |
| 72T 73Q 74S | 0.283 | 2.166 | 2.419 | 2.713 | 2.676 | 2.646 | 3.110 | 1.792 | |
| 72S 73V 74A | 0.340 | 2.127 | 2.330 | 2.397 | 2.295 | 2.601 | 2.727 | 1.572 | |
| 72G 74F | 0.467 | 1.669 | 1.970 | 2.116 | 1.490 | 2.304 | 2.996 | 0.669 | |
| 72I 73W 74N | 0.229 | 0.791 | 1.794 | 1.194 | 0.779 | 2.091 | 3.236 | 0.329 | |
| 73W 74I | 0.335 | 0.757 | 1.325 | 1.130 | 0.912 | 1.884 | 2.697 | 0.423 | |
| 72T 73W 74G | 0.205 | 0.687 | 1.702 | 1.348 | 0.822 | 1.817 | 2.770 | 0.305 | |
| 73N 72A 74F | 0.448 | 0.870 | 1.299 | 0.976 | 0.775 | 1.468 | 2.256 | 0.271 | |
| 38Y 74F 72A | 0.191 | 0.605 | 1.166 | 0.926 | 0.646 | 1.397 | 1.514 | 0.362 | |
| 72V 73L 74W | 0.248 | 0.500 | 1.209 | 1.225 | 0.648 | 1.276 | 1.710 | 0.348 | |
| 11I, 72A | 0.382 | 0.584 | 0.507 | 0.546 | 0.387 | 1.186 | | | |
| 18I 31L 73L 72A | 0.380 | 0.626 | 0.857 | 0.682 | 0.549 | 1.075 | 0.781 | 0.390 | |
| 72Q | 0.665 | 0.770 | 0.735 | 0.762 | 0.777 | 0.989 | | | |
| 14L 18L 73L 117A 72A | 0.372 | 0.905 | 0.641 | 0.657 | 0.355 | 0.071 | 0.410 | 0.031 | PA & SA very low |
| 38A 106V 117A 72A | 0.418 | 1.492 | 0.541 | 0.229 | 0.368 | 0.033 | 0.121 | 0.065 | AA highest |
| 14I 72G 117V | 0.312 | 0.928 | 0.547 | 0.622 | 0.337 | 0.085 | | | AA highest |
| 14L 72G 117V | 0.280 | 0.873 | 0.513 | 0.548 | 0.297 | 0.055 | | | AA highest |
| 14L 18S 31L 73V 117A 72A | 0.486 | 0.951 | 0.673 | 0.534 | 0.020 | 0.028 | −0.003 | 0.007 | AA highest |
| 106D, 72A | 0.240 | 0.502 | 0.591 | 0.584 | 0.423 | 0.147 | | | |
| 31I, 72A | 0.680 | 0.303 | 0.413 | 0.168 | −0.213 | 0.091 | | | |
| 55Y, 72A | 0.124 | 0.471 | 0.335 | 0.324 | 0.329 | 0.249 | | | PA & SA low |
| 14L 72G 117I | 0.246 | 0.787 | 0.812 | 0.764 | 0.395 | 0.231 | | | |
| 82F, 72A | 0.139 | 1.029 | 0.334 | 0.422 | 0.403 | 0.223 | | | |
| 106I, 72A | 0.291 | 0.481 | 0.624 | 0.563 | 0.661 | 0.223 | | | |
| 70W, 72A | 0.388 | 0.349 | 0.385 | 0.451 | 0.381 | 0.212 | | | |
| 119A, 72A | 0.304 | 0.540 | 0.520 | 0.450 | 0.490 | 0.200 | | | |
| 11W, 72A | 0.262 | 0.430 | 0.357 | 0.344 | 0.227 | 0.199 | | | |
| 106V, 72A | 0.261 | 0.398 | 0.592 | 0.574 | 0.657 | 0.191 | | | |
| 78A, 72A | 0.239 | 0.433 | 0.429 | 0.372 | 0.350 | 0.190 | | | |
| 106M, 72A | 0.231 | 0.554 | 0.490 | 0.485 | 0.510 | 0.183 | | | |
| 106L, 72A | 0.299 | 0.383 | 0.364 | 0.382 | 0.431 | 0.183 | | | |
| 106A, 72A | 0.249 | 0.389 | 0.518 | 0.515 | 0.596 | 0.164 | | | |
| 21I, 72A | 0.241 | 0.531 | 0.412 | 0.365 | 0.310 | 0.162 | | | |
| 49D, 72A | 0.231 | 0.308 | 0.296 | 0.324 | 0.316 | 0.161 | | | |
| 106N, 72A | 0.238 | 0.384 | 0.445 | 0.451 | 0.496 | 0.152 | | | |
| 106S, 72A | 0.258 | 0.321 | 0.403 | 0.355 | 0.478 | 0.149 | | | |
| 117D, 72A | 0.389 | 0.352 | 0.407 | 0.380 | 0.294 | 0.142 | | | |
| 104Y, 72A | 0.878 | 0.364 | 0.278 | 0.265 | 0.236 | 0.140 | | | |
| 14L 18I 31L 73F 117A 72A | 0.255 | 1.297 | 0.639 | 0.707 | 0.300 | 0.121 | 0.235 | 0.077 | |
| 106T, 72A | 0.228 | 0.250 | 0.367 | 0.246 | 0.434 | 0.118 | | | |
| 18L 73V 72A | 0.364 | 0.615 | 0.126 | 0.069 | 0.142 | 0.083 | 0.107 | 0.359 | |
| 73W 74T | 0.368 | 1.456 | 3.286 | 2.480 | 1.902 | 3.883 | 5.818 | 0.726 | Favors POA |
| 72A 73W 74V | 0.393 | 1.768 | 2.752 | 2.338 | 1.574 | 2.525 | 3.856 | 0.602 | |
| 72A 73P 74V | 0.377 | 2.354 | 2.845 | 2.735 | 2.187 | 2.406 | 3.613 | 1.178 | |
| 72V 73W 74N | 0.207 | 1.191 | 2.384 | 1.726 | 1.146 | 2.229 | 3.507 | 0.468 | |
| 72I 73W 74N | 0.229 | 0.791 | 1.794 | 1.194 | 0.779 | 2.091 | 3.236 | 0.329 | |
| 72T 73Q 74S | 0.283 | 2.166 | 2.419 | 2.713 | 2.676 | 2.646 | 3.110 | 1.792 | |
| 72A 73W 74A | 0.268 | 0.892 | 2.093 | 1.466 | 0.933 | 1.942 | 3.016 | 0.330 | |
| 72G 74F | 0.467 | 1.669 | 1.970 | 2.116 | 1.490 | 2.304 | 2.996 | 0.669 | |
| 72T 73W 74G | 0.205 | 0.687 | 1.702 | 1.348 | 0.822 | 1.817 | 2.770 | 0.305 | |
| 18I 31A 73F 72A | 0.330 | 1.314 | 2.318 | 1.732 | 0.950 | 1.515 | 2.730 | 0.404 | |
| 73W 74I | 0.335 | 0.757 | 1.325 | 1.130 | 0.912 | 1.884 | 2.697 | 0.423 | |
| 18V 31A 73F 72A | 0.308 | 1.142 | 2.036 | 1.527 | 0.828 | 1.510 | 2.677 | 0.375 | |
| 72V 73W 74S | 0.270 | 1.424 | 2.044 | 1.819 | 1.477 | 1.789 | 2.662 | 0.574 | |
| 73T 72A 74F | 0.300 | 0.939 | 1.661 | 1.389 | 1.161 | 1.632 | 2.450 | 0.519 | |
| 72S 73W 74G | 0.321 | 1.012 | 1.706 | 1.375 | 0.970 | 1.653 | 2.422 | 0.411 | |

TABLE 4-continued

| Mutations | Ro | DR/DR AA | DR/DR LNA | DR/DR LA | DR/DR OA | DR/DR PA | DR/DR POA | DR/DR SA | |
|---|---|---|---|---|---|---|---|---|---|
| 74S 72A 73F | 0.230 | 0.893 | 1.433 | 1.035 | 0.630 | 1.158 | 2.413 | 0.337 | |
| 74E 72A 73F | 0.259 | 0.703 | 1.558 | 1.093 | 0.575 | 1.026 | 2.395 | 0.251 | |
| 73F 72A | 0.299 | 1.051 | 1.775 | 1.171 | 0.630 | 1.118 | 2.381 | 0.399 | |
| 74T 72A 73F | 0.181 | 0.852 | 1.635 | 1.185 | 0.634 | 1.150 | 2.309 | 0.273 | |
| 55V 73F 72A | 0.328 | 0.864 | 1.566 | 1.223 | 0.661 | 1.082 | 2.264 | 0.285 | |
| 73N 72A 74F | 0.448 | 0.870 | 1.299 | 0.976 | 0.775 | 1.468 | 2.256 | 0.271 | |
| 38I 74F 72A | 0.276 | 0.787 | 1.395 | 1.162 | 0.764 | 1.343 | 2.112 | 0.503 | |
| 14L 18L 31W 73W 117L 72A | 0.201 | 1.772 | 1.640 | 1.782 | 1.085 | 0.970 | 2.059 | 0.294 | |
| 72V 73L 74W | 0.248 | 0.500 | 1.209 | 1.225 | 0.648 | 1.276 | 1.710 | 0.348 | |
| 38Y 74F 72A | 0.191 | 0.605 | 1.166 | 0.926 | 0.646 | 1.397 | 1.514 | 0.362 | |
| 74Q 72A 73F | 0.251 | 0.465 | 1.025 | 0.711 | 0.390 | 0.649 | 1.479 | 0.177 | |
| 72E 73V 74A | 0.296 | 0.478 | 0.784 | 0.735 | 0.524 | 0.736 | 1.093 | 0.234 | |
| 72H 73Y 74G | 0.205 | 0.600 | 0.591 | 0.472 | 0.140 | 0.486 | 0.986 | 0.052 | |
| 72G 73F 74N | 0.513 | 0.617 | 1.367 | 0.454 | −0.032 | 0.456 | 1.499 | −0.043 | PA & SA lowest, POA and LNA highest |
| 14L 18L 73W 117S 72A | 0.562 | 1.010 | 1.499 | 1.385 | 0.374 | 0.259 | 0.750 | −0.005 | SA ~zero, LNA, LA specific |
| 14Q 18S 73I 117W 72A | 0.487 | 0.878 | 0.894 | 0.784 | 0.809 | 0.559 | 0.834 | −0.044 | SA ~zero |
| 14L 18L 31L 73G 117V 72A | 0.440 | 1.180 | 1.139 | 1.170 | 0.031 | 0.377 | 0.180 | 0.170 | OA lowest, PUFA highest |
| 38A 106V 117A 72A | 0.418 | 1.492 | 0.541 | 0.229 | 0.368 | 0.033 | 0.121 | 0.065 | PA lowest, AA highest by 3 fold |
| 14L 18S 31L 73V 117A 72A | 0.486 | 0.951 | 0.673 | 0.534 | 0.020 | 0.028 | −0.003 | 0.007 | POA lowest |
| 38Y 117A 72A | 0.350 | 2.216 | 1.547 | 1.869 | 1.976 | 0.933 | 0.839 | 1.201 | |
| 62N 106F 117A 72A | 0.224 | 1.265 | 0.756 | 0.985 | 0.864 | 0.430 | 0.341 | 0.490 | |
| 38Y 62W 117A 72A | 0.554 | 2.353 | 1.237 | 1.848 | 1.896 | 0.316 | 0.272 | 0.854 | |
| 38Q 62I 106I 117A 72A | 0.215 | 1.656 | 0.930 | 1.288 | 1.167 | 0.550 | 0.473 | 0.663 | |

TABLE 5

| | | DR/DRAD2 | | | | |
|---|---|---|---|---|---|---|
| Clone | Ro | AA | LNA | LA | OA | PA |
| L72A | 0.17 | 1.12 | 1.16 | 1.14 | 1.15 | 1.02 |
| L72G | 0.28 | 0.62 | 0.48 | 0.48 | 0.52 | 0.26 |
| L72M | 0.38 | 1.31 | 1.35 | 1.46 | 1.49 | 1.32 |
| A73F, L72A | 0.33 | 1.21 | 1.86 | 1.23 | 0.73 | 1.13 |
| A73I, L72A | 0.27 | 0.38 | 0.03 | −0.04 | −0.04 | −0.04 |
| D74F, L72A | 0.25 | 0.44 | 1.04 | 0.67 | 0.51 | 0.93 |
| L78F, L72A | 0.35 | 2.04 | 2.05 | 2 | 1.83 | 0.91 |
| W82F, L72A | 0.27 | 0.68 | 0.76 | 1.08 | 0.78 | 0.41 |
| R106W, L72A | 0.24 | 1.11 | 1.03 | 1.04 | 0.99 | 0.41 |
| Y117A, L72A | 0.28 | 1.27 | 0.62 | 1.01 | 0.93 | 0.32 |
| Y117S, L72A | 0.36 | 1.35 | 1.07 | 1.42 | 1.19 | 0.55 |

TABLE 6

| | | ΔR/DRAΔ2 | | | | | Mutations | | | |
|---|---|---|---|---|---|---|---|---|---|---|
| ID | Ro | AA | LNA | LA | OA | PA | Y14 | L38 | L72 | Y117 |
| L1P8 H2 | 0.69 | −1.3 | −1.3 | −1.5 | −1.7 | −0.6 | M | M | W | wt |
| L1P7 H4 | 0.62 | −1.0 | −1.1 | −1.3 | −1.4 | −0.6 | I | M | W | wt |
| L1P1 C3 | 0.60 | −0.9 | −1.0 | −1.1 | −1.3 | −0.4 | M | wt | W | wt |
| L1P17 A1 | 0.56 | −0.8 | −0.9 | −1.0 | −1.2 | −0.4 | I | wt | W | wt |
| L1P12 E11 | 0.59 | −0.5 | −0.7 | −0.7 | −1.0 | −0.1 | L | wt | W | wt |
| L1P12 F12 | 0.28 | 0.9 | 0.5 | 0.5 | 0.3 | 0.1 | L | wt | G | V |
| L1P2 F7 | 0.32 | 0.9 | 0.5 | 0.6 | 0.3 | 0.1 | I | wt | G | V |
| L1P7 B11 | 0.21 | 0.7 | 0.9 | 0.9 | 0.4 | 0.8 | I | I | V | wt |
| L1P12 G10 | 0.35 | 0.8 | 1.0 | 0.9 | 0.5 | 0.8 | I | wt | wt | wt |
| L1P3 D6 | 0.24 | 0.9 | 0.9 | 0.8 | 0.5 | 0.5 | L | wt | wt | wt |
| L1P1 F7 | 0.22 | 0.9 | 1.0 | 0.9 | 0.5 | 0.5 | L | M | wt | F |
| L1P14 A9 | 0.25 | 0.8 | 0.8 | 0.8 | 0.4 | 0.2 | L | wt | G | I |
| L1P11 F12 | 0.27 | 1.0 | 1.2 | 1.1 | 0.7 | 0.7 | I | wt | wt | wt |
| L1P17 A8 | 0.24 | 1.3 | 0.7 | 0.8 | 0.7 | 0.4 | wt | M | G | F |
| L1P9 G10 | 0.29 | 1.0 | 0.7 | 0.8 | 0.9 | 0.4 | wt | I | G | wt |
| L1P16 G10 | 0.34 | 0.9 | 1.3 | 1.1 | 0.7 | 0.8 | W | wt | M | A |
| L1P5 A10 | 0.28 | 1.5 | 0.7 | 1.2 | 1.1 | 0.4 | wt | wt | wt | A |
| L1P8 D4 | 0.31 | 1.6 | 2.0 | 2.0 | 1.1 | 0.9 | M | wt | M | A |

TABLE 7

| ID | Ro | ΔR/DRAΔ2 | | | | | | | Sequence | | | |
| --- | --- | --- | --- | --- | --- | --- | --- | --- | --- | --- | --- | --- |
| | | AA | LNA | LA | OA | PA | POA | SA | M18 | G31 | F55 | A73 |
| L2P17H10 | 0.23 | 1.8 | 1.2 | 1.5 | 1.4 | 1.0 | 1.2 | 1.7 | G | F | WT | L |
| L2P22G6 | 0.30 | 1.8 | 2.7 | 2.6 | 1.6 | 1.9 | 2.6 | 0.9 | I | Y | WT | G |
| L2P11B4 | 0.35 | 1.8 | 2.8 | 2.6 | 1.9 | 2.2 | 3.1 | 0.7 | V | A | WT | W |
| L2P2E11 | 0.31 | 1.9 | 2.8 | 2.5 | 1.6 | 2.0 | 2.6 | 0.8 | I | F | WT | WT |
| L2P4C5 | 0.35 | 2.2 | 2.8 | 2.8 | 2.1 | 1.8 | 2.6 | 1.0 | I | Y | WT | WT |
| L2P1E6 | 0.34 | 0.4 | 0.1 | 0.1 | 0.1 | 0.0 | 0.1 | 0.2 | L | WT | WT | L |
| L2P8F11 | 0.28 | 0.4 | 0.1 | 0.0 | 0.0 | 0.0 | 0.1 | 0.3 | WT | WT | WT | I |
| L2P12G9 | 0.46 | 0.5 | 0.0 | −0.1 | 0.0 | 0.0 | 0.0 | 0.4 | L | WT | WT | V |
| L2P9E12 | 0.38 | 0.6 | 0.9 | 0.7 | 0.6 | 1.1 | 0.8 | 0.4 | L | WT | L | I |
| L2P22H10 | 0.30 | 0.9 | 1.3 | 1.1 | 0.6 | 1.1 | 1.2 | 0.4 | I | WT | G | M |
| L2P8B8 | 0.31 | 1.1 | 1.8 | 1.2 | 0.6 | 1.1 | 2.4 | 0.4 | WT | WT | WT | F |
| L2P16A3 | 0.37 | 1.0 | 1.5 | 1.1 | 0.6 | 1.1 | 1.4 | 0.3 | I | L | WT | G |
| L2P7F4 | 0.32 | 0.8 | 1.5 | 1.1 | 0.6 | 1.3 | 1.3 | 0.3 | V | V | WT | I |
| L2P21G3 | 0.36 | 1.0 | 1.4 | 1.1 | 0.6 | 1.1 | 1.4 | 0.3 | I | M | M | WT |
| L2P23G7 | 0.30 | 0.9 | 1.2 | 1.0 | 0.6 | 1.0 | 1.4 | 0.4 | V | F | L | WT |
| L2P22E6 | 0.35 | 1.0 | 1.6 | 1.3 | 0.8 | 1.3 | 1.6 | 0.4 | V | A | I | W |
| L2P18H12 | 0.36 | 1.3 | 1.9 | 1.7 | 1.0 | 1.6 | 2.1 | 0.5 | I | V | WT | G |
| L2P8A5 | 0.35 | 1.1 | 1.9 | 1.6 | 0.9 | 1.5 | 2.0 | 0.4 | V | A | W | W |
| L2P21C1 | 0.36 | 2.8 | 3.1 | 3.4 | 2.7 | 2.0 | 2.9 | 1.6 | I | Y | WT | V |
| L2P23A4 | 0.40 | 2.8 | 2.6 | 3.1 | 2.3 | 1.9 | 2.8 | 1.2 | V | I | L | V |
| L2P12C5 | 0.39 | 1.3 | 1.7 | 1.5 | 0.8 | 1.5 | 1.9 | 0.4 | I | I | M | I |
| L2P8A6 | 0.36 | 0.6 | 1.2 | 0.8 | 0.4 | 1.0 | 1.3 | 0.2 | I | V | V | V |

EXAMPLE 6

A probe for unbound unconjugated bilirubin (UCBu) was developed and used to measure concentrations of UCBu in plasma spiked with a defined quantity of unconjugated bilirubin (UCB). Using 384-well plates, 335 mutant probes that were insensitive to FFA were screened for their response to UCB:BSA complexes at UCB:BSA ratios of 1:1 and 1:2 in aqueous buffer. All probes were prepared from rI-FABP-L72A (SEQ ID NO: 4) with 1 to 5 mutations. Screening was conducted by comparing the fractional change in fluorescence intensity (ΔI/Io, where ΔI is the difference in probe intensity in the presence and absence of UCB and Io is the intensity in the absence of UCB) for the probes with that for ADIFAB2. This value was calculated for two emission wavelengths: 440 and 500 nm. Several probes were identified that had significantly improved responses to UCBu as compared to the template, ADIFAB2 (Table 8). The emitted fluorescence of these probes is quenched by binding of UCB.

non-linear fit to the data gives a Kd of 150 nM. Table 3 lists the Kd values and mutations for some example probes.

Figure 4:
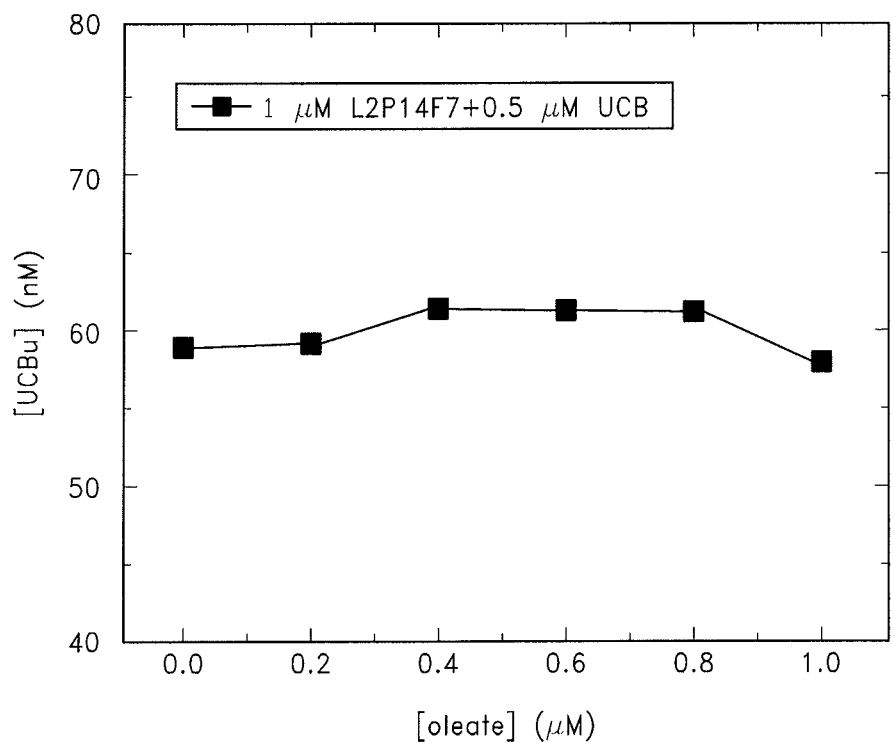
FIG. 4 shows a titration of a mixture of 0.5 µM unbound unconjugated bilirubin (UCB) and 1 µM of the probe L2P14F7 with sodium oleate.

Initial screening of the UCB-probes indicated that the probes do not respond to FFA. This property was confirmed by titration of a mixture of 0.5 µM UCB and 1 µM L2P14F7 with sodium oleate. The probe shows no change in response even after 1 µM total oleate has been added to the solution (FIG. 4). Oleic acid is the most abundant FFA in serum, and measurements of normal serum samples indicate that typical unbound concentrations of oleic acid are less than 1 nM. By using non-responsive probes from FFA screening to conduct a secondary screening with other unbound analytes, a UCB-sensitive probe that has a negligible response to the major FFA in blood has been generated from a rI-FABP-L72A mutant.

Figure 5:
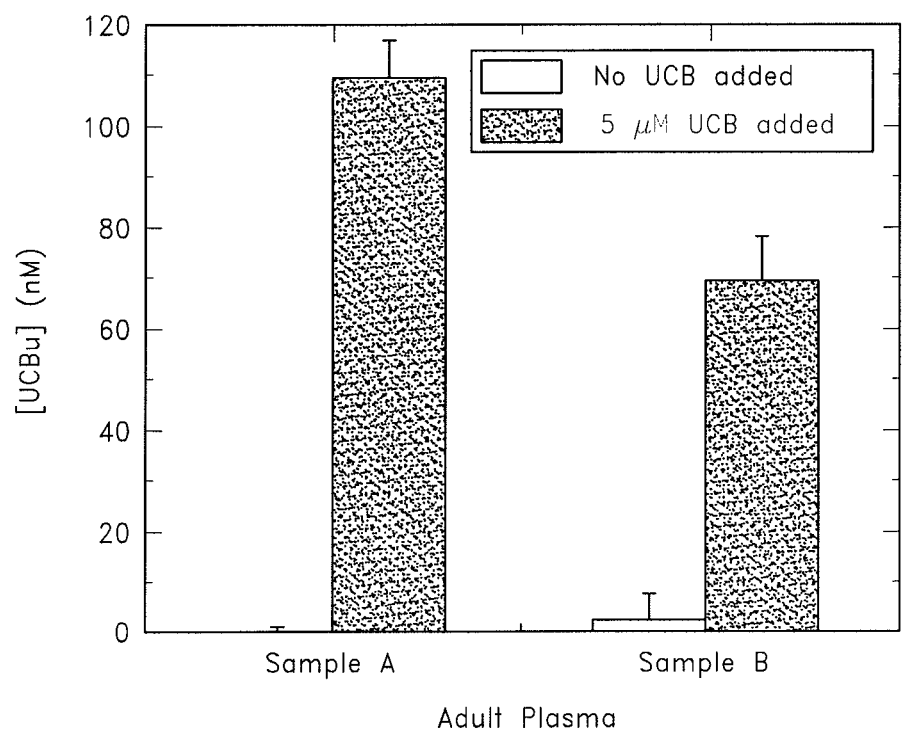
FIG. 5 shows the response of L2P14F7 to plasma samples of healthy adult donors in the presence (shaded) and absence (open) of 5 µM unbound unconjugated bilirubin (UCB).

The response of L2P14F7 to plasma samples from healthy adult donors, for which the UCBu concentration is expected to be about 1 nM or less, was measured (FIG. 5). Samples were diluted to 1% by volume in pH 7.4 HEPES buffer. Little

TABLE 8

| | ΔI/Io | | | | | |
| --- | --- | --- | --- | --- | --- | --- |
| | 1:2 UCB:BSA | | 1:1 UCB:BSA | | | |
| PROBE ID | 440 nm | 500 nm | 440 nm | 500 nm | Kd (nM) at 22° C. | Mutations |
| ADIFAB2 | −0.19 | −0.16 | −0.40 | −0.34 | — | — |
| L1P1 B4 | −0.36 | −0.35 | −0.66 | −0.64 | 590 | 14I 72W 117W |
| L1P1 C12 | −0.86 | −0.79 | −0.92 | −0.86 | 37 | 38I 72W 117W |
| L1P12 E8 | −0.45 | −0.39 | −0.79 | −0.70 | 112 | 14L 38A 72G 117F 114E |
| L1P14 D6 | −0.37 | −0.33 | −0.69 | −0.64 | 230 | 14M 72V 117W |
| L1P5 H9 | −0.34 | −0.34 | −0.58 | −0.63 | 490 | 14M 72I 117W |
| L2P22 B1 | −0.36 | −0.35 | −0.70 | −0.68 | 550 | 18Y 31V 55V 72A |
| L5P16 H4 | −0.37 | −0.31 | −0.69 | −0.64 | 390 | 126K 73F 72A |

Figure 3:
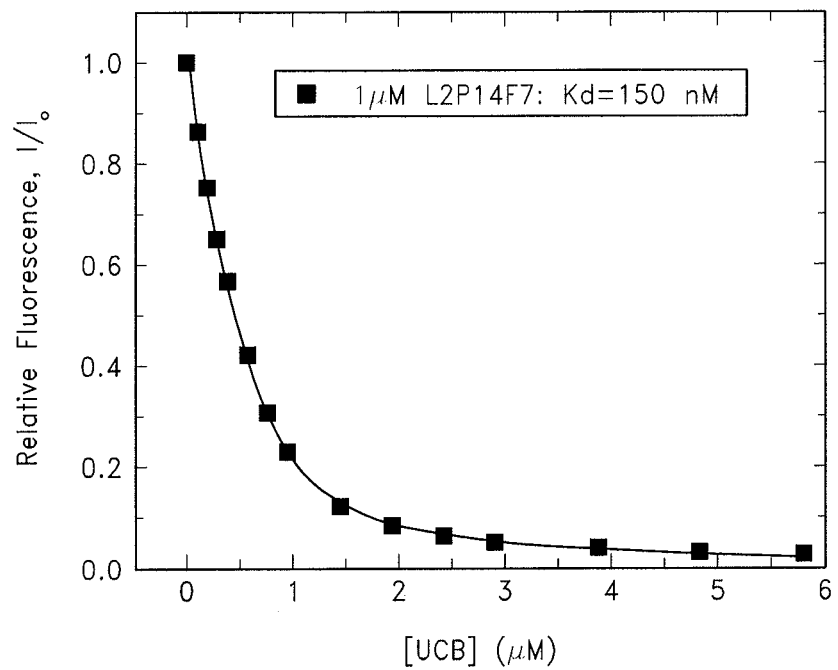
FIG. 3 shows a binding isotherm for the probe L2P14F7.

Larger preparations of select probes were prepared for quantitative determination of binding affinities. Binding isotherms were performed by measuring the fluorescence intensity for 1 µM of a given probe as the probe was titrated with known quantities of UCB. A binding isotherm for the probe L2P14F7 (mutations: 18G 31M 72A) is shown in FIG. 3. A to no response was observed for these samples, indicating that no components within the plasma samples bind to L2P14F7 and alter its fluorescence. To demonstrate that the probe was still active, the samples were spiked with 5 µM UCB, and the probe fluorescence was measured again. A substantial decrease in the fluorescence was observed for both samples A and B, corresponding to UCBu concentrations of 110 and 70 nM (FIG. 3). An albumin assay revealed that sample B had a significantly greater serum albumin concentration than sample A, which is consistent with the lower levels of UCBu detected in sample B. The results demonstrate that L2P14F7 is a UCB-specific probe with no appreciable affinity for other typical serum components and that this probe can be used to measure pathophysiologic levels of UCBu in plasma.

It will be understood by those of skill in the art that numerous and various modifications can be made without departing from the spirit of the present invention. Therefore, it should be clearly understood that the forms of the present invention are illustrative only and are not intended to limit the scope of the present invention.

---

What is claimed is:

1. A method to determine a concentration of unbound bilirubin in body fluids of a mammal which comprises:

providing an unbound bilirubin probe having a $\Delta R/\Delta R_{ADIFAB2}$ which is <0.1 for unbound fatty acids by selecting a fluorescently labeled FABP mutein which binds to unbound bilirubin, wherein the fluorescence intensity of the unbound bilirubin probe is quenched by the binding of unbound bilirubin, and wherein $\Delta I/I_0$ for the unbound bilirubin probe is >1.45 $\Delta I/I_0$ for ADIFAB2, wherein $\Delta I$ is the difference in fluorescence intensity of the probe in the presence (I) and absence ($I_0$) of unbound bilirubin by performing the following steps:

(i) providing a reference Fatty Acid Binding Protein (FABP) mutein comprising the amino acid sequence of SEQ ID NO: 2 having amino acid substitutions selected from the group consisting of 18G31M72A, 14I72W117W, 14M72I117W, 126K73F72A, 38I72W117W, 14L38A72G117F114E, 18Y31V55V72A and 14M72V117W, (ii) generating polynucleotides encoding a FABP library comprising an assortment of FABP muteins of the reference FABP mutein from a polynucleotide template to generate a library of FABP muteins, (iii) expressing the FABP muteins, (iv) muteins by binding to a solid matrix, (v) labeling the matrix bound FABP muteins with a single fluorophore at a specific site on each FABP mutein to produce multiple probes with altered specificity for unbound bilirubin relative to the reference labeled FABP mutein from the solid matrix, (vi) retrieving the probes with altered specificity for unbound bilirubin relative to the reference FABP mutein, (vii) screening the probes by fluorescence in the presence and absence of unbound bilirubin to determine Kd for unbound bilirubin, withdrawing a body fluid from the mammal;

contacting the body fluid with the unbound bilirubin probe;

measuring the fluorescence intensity of the unbound bilirubin probe in the body fluid to determine I, measuring the fluorescence intensity of the unbound bilirubin probe in a fluid without bilirubin present to determine $I_0$, and calculating the unbound bilirubin concentration using I, $I_0$ and Kd according to the equation: unbound bilirubin concentration=$Kd(I/I_0-1)$.

2. The method of claim 1, wherein the body fluid is selected from the group consisting of whole blood, blood plasma, blood serum, urine, CSF, saliva, gastric juices, interstitial fluid, synovial fluid and lymph.

3. The method of claim 1, wherein the bilirubin binding FABP mutein comprises a substitution at position 117.

4. The method of claim 1, wherein the bilirubin binding FABP mutein comprises a substitution at position 31.

5. The method of claim 1, wherein the bilirubin binding FABP mutein comprises a substitution at position 18.

6. The method of claim 1, wherein the bilirubin binding FABP mutein comprises 1-5 additional substitutions.

* * * * *

UNITED STATES PATENT AND TRADEMARK OFFICE
CERTIFICATE OF CORRECTION

PATENT NO. : 8,466,090 B2
APPLICATION NO. : 12/535617
DATED : June 18, 2013
INVENTOR(S) : Kleinfeld et al.

It is certified that error appears in the above-identified patent and that said Letters Patent is hereby corrected as shown below:

Title Page

In column 1 (page 2 item 56) at line 18, Under Other Publications, change "Joumal" to --Journal--.

In column 1 (page 2 item 56) at line 29, Under Other Publications, change "Add" to --Acid--.

In column 1 (page 2 item 56) at line 51, Under Other Publications, change "171-182," to --171-183,--.

In column 1 (page 2 item 56) at line 56, Under Other Publications, change "Docosahexanoic" to --Docosahexaenoic--.

In column 1 (page 2 item 56) at line 61, Under Other Publications, change "lschemia,"" to --Ischemia,"--.

In column 1 (page 2 item 56) at line 68, Under Other Publications, change "lschemia,"" to --Ischemia,"--.

In column 2 (page 2 item 56) at line 49, Under Other Publications, change "Biliruibin" to --Bilirubin--.

In column 2 (page 2 item 56) at line 50, Under Other Publications, change "ot" to --of--.

In column 2 (page 3 item 56) at line 14, Under Other Publications, change "Kernicturus." to --Kernicterus.--.

In the Specifications

In column 2 at line 10, Change "eiconsanoids," to --eicosanoids,--.

In column 2 at line 29, Change "Bemlohr et al" to --Bernlohr et al--.

In column 4 at line 5, Change "formula" to --formula:--.

In column 8 at line 37, Change "construction" to --construction.--.

Signed and Sealed this
Twenty-eighth Day of January, 2014

Michelle K. Lee
*Deputy Director of the United States Patent and Trademark Office*

CERTIFICATE OF CORRECTION (continued)
U.S. Pat. No. 8,466,090 B2

In column 9 at line 20, Change "NH2-" to --$NH_2$- --.

In column 12 at line 3, Change "procaryotic or eukarotic." to --prokaryotic or eukaryotic.--.

In column 15 at line 30, Change "gaps)" to --gaps).--.

In column 19 at line 34, Change "determined" to --determine--.

In column 19 at lines 55-57 (approx., including equations), Change

" $FFA_{AA}\left(\dfrac{R_{m2PA} - R_2}{Q_{2PA} Kd_{2PA}}\right) = R_2 - R_{02}$ " to -- $FFA_{PA}\left(\dfrac{R_{m2PA} - R_2}{Q_{2PA} Kd_{2PA}}\right) = R_2 - R_{02}$ --.

In the Claims

In column 47 at line 36, In Claim 1, change "38I72W117W," to --38I72W117W,--.

In column 47 at line 43, In Claim 1, before "muteins" insert --purifying the FABP--.

SEQUENCE LISTING

<160> NUMBER OF SEQ ID NOS: 4

<210> SEQ ID NO 1
<211> LENGTH: 399
<212> TYPE: DNA
<213> ORGANISM: Rattus norvegicus
<220> FEATURE:
<221> NAME/KEY: CDS
<222> LOCATION: (1)...(399)
<223> OTHER INFORMATION: wild-type rat intestinal fatty acid binding
      protein cDNA sequence

<400> SEQUENCE: 1

```
atg gca ttt gat ggc act tgg aaa gta tac cgg aat gag aac tat gaa      48
Met Ala Phe Asp Gly Thr Trp Lys Val Tyr Arg Asn Glu Asn Tyr Glu
 1               5                  10                  15 aag ttc atg gag aaa atg ggc att aac gtg gtg aag agg aag ctt gga      96
Lys Phe Met Glu Lys Met Gly Ile Asn Val Val Lys Arg Lys Leu Gly
             20                  25                  30 gct cat gac aac ttg aaa ctg acg atc aca cag gaa gga aat aaa ttc     144
Ala His Asp Asn Leu Lys Leu Thr Ile Thr Gln Glu Gly Asn Lys Phe
         35                  40                  45 aca gtc aaa gaa tca agc aac ttc cga aac att gat gtt gtg ttt gaa     192
Thr Val Lys Glu Ser Ser Asn Phe Arg Asn Ile Asp Val Val Phe Glu
     50                  55                  60 ctc ggc gtc gac ttt gcc tat agt cta gca gat gga aca gaa ctc act     240
Leu Gly Val Asp Phe Ala Tyr Ser Leu Ala Asp Gly Thr Glu Leu Thr
 65                  70                  75                  80 ggg acc ttg acc atg gag gga aat aaa ctt gtt gga aaa ttc aaa cgt     288
Gly Thr Leu Thr Met Glu Gly Asn Lys Leu Val Gly Lys Phe Lys Arg
                 85                  90                  95 gta gac aat gga aag gag ctg att gct gtc cga gag att tct ggt aac     336
Val Asp Asn Gly Lys Glu Leu Ile Ala Val Arg Glu Ile Ser Gly Asn
            100                 105                 110 gaa cta atc caa acc tac aca tat gaa gga gtg gag gcc aag cgc atc     384
Glu Leu Ile Gln Thr Tyr Thr Tyr Glu Gly Val Glu Ala Lys Arg Ile
        115                 120                 125 ttt aag aag gaa tag                                                  399
Phe Lys Lys Glu *
    130
```

<210> SEQ ID NO 2
<211> LENGTH: 131
<212> TYPE: PRT
<213> ORGANISM: Rattus norvegicus
<220> FEATURE:
<221> NAME/KEY: PEPTIDE
<222> LOCATION: (1)...(131)
<223> OTHER INFORMATION: wild-type rat intestinal fatty acid binding
      protein
<220> FEATURE:
<221> NAME/KEY: ACETYLATION
<222> LOCATION: (1)...(1)

<400> SEQUENCE: 2

```
Ala Phe Asp Gly Thr Trp Lys Val Asp Arg Asn Glu Asn Tyr Glu Lys
 1               5                  10                  15
```

```
Phe Met Glu Lys Met Gly Ile Asn Val Val Lys Arg Lys Leu Gly Ala
            20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
    50                  55                  60

Gly Val Asp Phe Ala Tyr Ser Leu Ala Asp Gly Thr Glu Leu Thr Gly
65                  70                  75                  80

Thr Trp Thr Met Glu Gly Asn Lys Leu Val Gly Lys Phe Lys Arg Val
                85                  90                  95

Asp Asn Gly Lys Glu Leu Ile Ala Val Arg Glu Ile Ser Gly Asn Glu
            100                 105                 110

Leu Ile Gln Thr Tyr Thr Tyr Glu Gly Val Glu Ala Lys Arg Ile Phe
        115                 120                 125

Lys Lys Glu
    130
```

<210> SEQ ID NO 3
<211> LENGTH: 426
<212> TYPE: DNA
<213> ORGANISM: Rattus norvegicus
<220> FEATURE:
<221> NAME/KEY: mutation
<222> LOCATION: (1)...(426)
<223> OTHER INFORMATION: rat intestinal fatty acid binding protein DNA
      sequence coding for substitution of alanine for
      leucine at position 72
<223> OTHER INFORMATION: 3' terminus codes for a 6his tag

<400> SEQUENCE: 3

```
atggcatttg atggcacttg gaaagtagac cggaatgaga actatgaaaa gttcatggag    60
aaaatgggca ttaacgtggt gaagaggaag cttggagctc atgacaactt gaaactgacg   120
atcacacagg aaggaaataa attcacagtc aaagaatcaa gcaacttccg aaacattgat   180
gttgtgtttg aactcggcgt cgactttgcc tatagtgctg cagatggaac agaactcacc   240
ggtacctgga caatggaggg aaataaactt gttggaaagt ttaaacgtgt agacaatgga   300
aaggagctga ttgctgtccg agagatttct ggtaacgaac taatccagac ctacacatat   360
gaaggagtgg aggccaagcg gatctttaag aaggaccgcg gtcatcatca ccatcatcac   420
tagtaa                                                              426
```

<210> SEQ ID NO 4
<211> LENGTH: 139
<212> TYPE: PRT
<213> ORGANISM: Rattus norvegicus
<220> FEATURE:
<221> NAME/KEY: MUTAGEN
<222> LOCATION: (72)...(72)
<223> OTHER INFORMATION: rat intestinal fatty acid binding protein with
      alanine substitution for leucine at position 72
<223> OTHER INFORMATION: 6His tag at N terminus

<400> SEQUENCE: 4

```
Ala Phe Asp Gly Thr Trp Lys Val Asp Arg Asn Glu Asn Tyr Glu Lys
1               5                   10                  15

Phe Met Glu Lys Met Gly Ile Asn Val Val Lys Arg Lys Leu Gly Ala
            20                  25                  30

His Asp Asn Leu Lys Leu Thr Ile Thr Gln Glu Gly Asn Lys Phe Thr
        35                  40                  45

Val Lys Glu Ser Ser Asn Phe Arg Asn Ile Asp Val Val Phe Glu Leu
    50                  55                  60
```

```
            50                  55                  60
Gly Val Asp Phe Ala Tyr Ser Ala Ala Asp Gly Thr Glu Leu Thr Gly
 65              70              75              80

Thr Trp Thr Met Glu Gly Asn Lys Leu Val Gly Lys Phe Lys Arg Val
             85              90              95

Asp Asn Gly Lys Glu Leu Ile Ala Val Arg Glu Ile Ser Gly Asn Glu
            100             105             110

Leu Ile Gln Thr Tyr Thr Tyr Glu Gly Val Glu Ala Lys Arg Ile Phe
            115             120             125

Lys Lys Asp Arg Gly His His His His His
        130             135
```